US012173065B2

(12) United States Patent
Leung

(10) Patent No.: US 12,173,065 B2
(45) Date of Patent: Dec. 24, 2024

(54) FUSION PROTEINS COMPRISING EXTRACELLULAR DOMAIN OF HUMAN CD22

(71) Applicant: SinoMab BioScience Limited, Pak Shek Kok (HK)

(72) Inventor: Shui-On Leung, New Territories (HK)

(73) Assignee: SINOMAB BIOSCIENCE LIMITED, Hong Kong (HK)

(*) Notice: Subject to any disclaimer, the term of this patent is extended or adjusted under 35 U.S.C. 154(b) by 733 days.

(21) Appl. No.: 17/283,693

(22) PCT Filed: Oct. 18, 2019

(86) PCT No.: PCT/CN2019/111886
§ 371 (c)(1),
(2) Date: Apr. 8, 2021

(87) PCT Pub. No.: WO2020/078454
PCT Pub. Date: Apr. 23, 2020

(65) Prior Publication Data
US 2021/0363246 A1 Nov. 25, 2021

Related U.S. Application Data

(60) Provisional application No. 62/775,631, filed on Dec. 5, 2018, provisional application No. 62/747,581, filed on Oct. 18, 2018.

(51) Int. Cl.
C07K 16/28 (2006.01)
A61K 9/00 (2006.01)
A61K 39/395 (2006.01)
A61K 45/06 (2006.01)
A61P 19/02 (2006.01)
A61P 35/00 (2006.01)
A61P 37/06 (2006.01)
C07K 14/705 (2006.01)
G01N 33/68 (2006.01)
A61K 39/00 (2006.01)

(52) U.S. Cl.
CPC ........ *C07K 16/2803* (2013.01); *A61K 9/0019* (2013.01); *A61K 39/3955* (2013.01); *A61K 45/06* (2013.01); *A61P 19/02* (2018.01); *A61P 35/00* (2018.01); *A61P 37/06* (2018.01); *C07K 14/70503* (2013.01); *G01N 33/68* (2013.01); *A61K 2039/505* (2013.01); *A61K 2039/545* (2013.01); *C07K 2317/34* (2013.01); *C07K 2317/56* (2013.01); *C07K 2317/76* (2013.01); *C07K 2317/77* (2013.01); *C07K 2317/92* (2013.01); *C07K 2319/00* (2013.01); *G01N 2333/70503* (2013.01); *G01N 2500/02* (2013.01); *G01N 2500/10* (2013.01)

(58) Field of Classification Search
CPC .......... C07K 2319/00; C07K 14/70503; C07K 16/2803; C07K 14/705; C12N 5/10; C12P 21/08
See application file for complete search history.

(56) References Cited

U.S. PATENT DOCUMENTS

2015/0239974 A1  8/2015  Chang et al.
2016/0363597 A1  12/2016  Leung

FOREIGN PATENT DOCUMENTS

| CN | 1429843 A | 7/2003 |
| CN | 1542019 A | 11/2004 |
| CN | 103588882 A | 2/2014 |
| WO | 2013188864 A2 | 12/2013 |

OTHER PUBLICATIONS

Collins, B.E. et al. "Masking of CD22 by cis ligands does not prevent redistribution of CD22 to sites of cell contact." PNAS, vol. 101, No. 16, Apr. 20, 2004 (Apr. 20, 2004), pp. 6104-6109.
Collins, B.E.et al. "High-Affinity Ligand Probes of CD22 Overcome the Threshold Set by cis Ligands to Allow for Binding, Endocytosis, and Killing of B Cells." The Journal of Immunology, vol. 177, Dec. 31, 2006 (Dec. 31, 2006), pp. 2994-3003.
Danzer, C.P.et al. "Transitional and marginal zone B cells have a high proportion of unmasked CD22: implications for BCR signaling"; International Immunology, vol. 15, No. 10, Dec. 31, 2003 (Dec. 31, 2003), pp. 1137-1147.
Floyd, H.et al. "A novel subset of murine B cells that expresses unmasked forms of CD22 is enriched in the bone marrow: implications for B-cell homing to the bone marrow" Immunology, vol. 101, Dec. 31, 2000 (Dec. 31, 2000), pp. 342-347.

(Continued)

Primary Examiner — Elly-Gerald Stoica
(74) Attorney, Agent, or Firm — Juniv LLP

(57) ABSTRACT

A method for restoring immune control over autoimmunity in a subject in need thereof is described. The method comprises the step of administering to the subject a therapeutically effective amount of an antibody that disrupts Siglec-binding in cis. A method of screening for an antibody that is disruptive of Siglec binding in cis, a method of making an antibody for restoring immune control over autoimmunity to a subject in need, a method of modulating autoimmunity in an immune cell and a method of releasing sialic acid binding site of human CD22 from cis-binding configuration to trans-ligand formation in treating autoimmunity in a subject in need thereof are also described. Kits containing a pharmaceutical composition and instructions for dosing, and preloaded syringes containing pharmaceutical compositions are also disclosed herein.

12 Claims, 14 Drawing Sheets

Specification includes a Sequence Listing.

(56) References Cited

OTHER PUBLICATIONS

Leung, S.O. et al. "Surrogate target cells expressing surface anti-idiotype antibody for the clinical evaluation of an internalizing CD22-specific antibody." MAbs, vol. 7, Jan./Feb. 2015, pp. 66-76.
Nitschke, L. et al. "Identification of CD22 ligands on bone marrow sinusoidal endothelium implicated in CD22-dependent homing of recirculating B cells." Journal of Experimental Medicine, vol. 189, No. 9, May 3, 1999 (May 3, 1999), pp. 1513-1518.

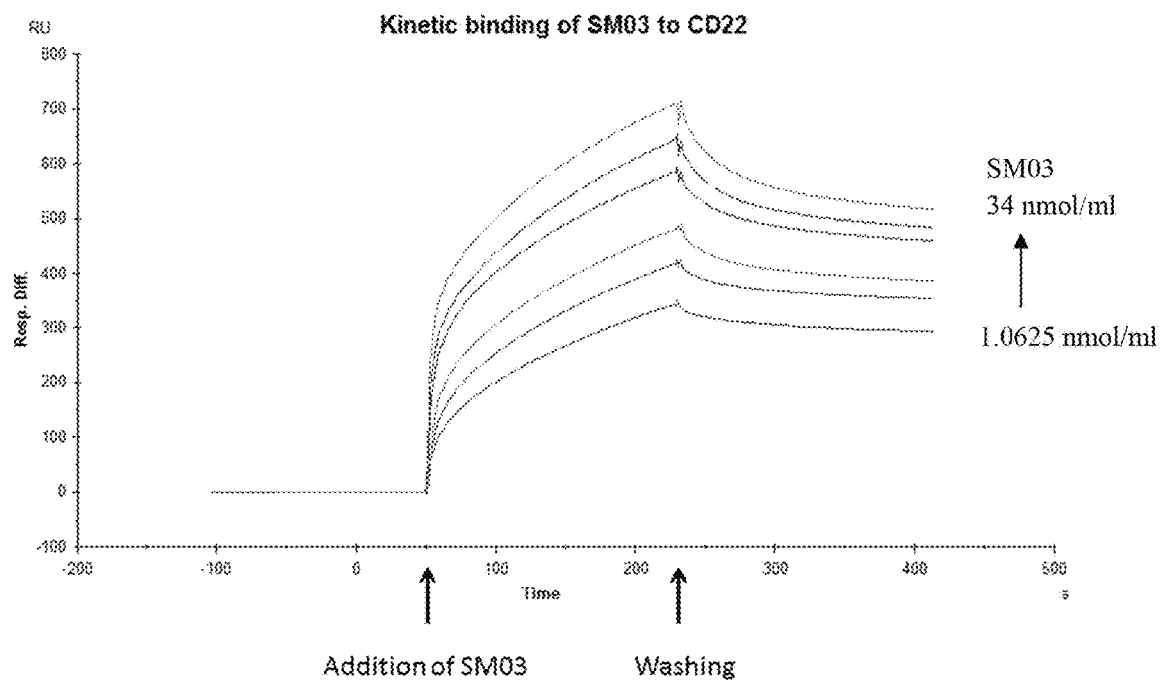
FIGURE 1
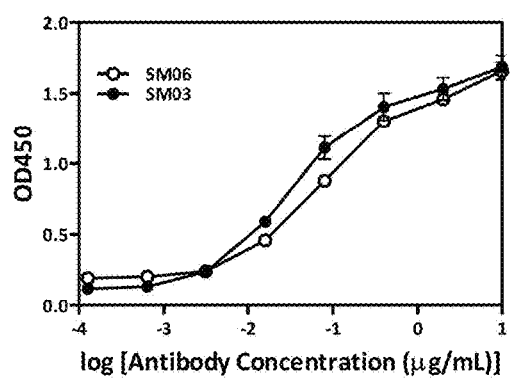 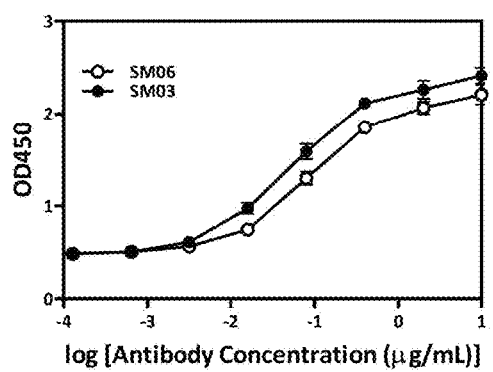
FIGURE 2(A)  FIGURE 2(B)

Percentage of ACR20 Responders following dosing with SM03 or Placebo

Percentage of ACR50 Responders following dosing with SM03 or Placebo

Percentage of ACR70 Responders following dosing with SM03 or Placebo

```
                               SEQUENCE LISTING

<160> NUMBER OF SEQ ID NOS: 17

<210> SEQ ID NO 1
<211> LENGTH: 108
<212> TYPE: PRT
<213> ORGANISM: Artificial Sequence
<220> FEATURE:
<221> NAME/KEY: MISC_FEATURE
<222> LOCATION: (1)..(108)
<223> OTHER INFORMATION: SM03 LCVR

<400> SEQUENCE: 1

Asp Ile Gln Leu Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 2
<211> LENGTH: 11
<212> TYPE: PRT
<213> ORGANISM: Artificial Sequence
<220> FEATURE:
<221> NAME/KEY: MISC_FEATURE
<222> LOCATION: (1)..(11)
<223> OTHER INFORMATION: SM03 LCVR CDR1

<400> SEQUENCE: 2

Arg Ala Ser Gln Asp Ile Ser Asn Tyr Leu Asn
1               5                   10

<210> SEQ ID NO 3
<211> LENGTH: 7
<212> TYPE: PRT
<213> ORGANISM: Artificial Sequence
<220> FEATURE:
<221> NAME/KEY: MISC_FEATURE
<222> LOCATION: (1)..(7)
<223> OTHER INFORMATION: SM03 LCVR CDR2

<400> SEQUENCE: 3

Tyr Thr Ser Ile Leu His Ser
1               5

<210> SEQ ID NO 4
<211> LENGTH: 9
<212> TYPE: PRT
<213> ORGANISM: Artificial Sequence
<220> FEATURE:
<221> NAME/KEY: MISC_FEATURE
<222> LOCATION: (1)..(9)
```

<223> OTHER INFORMATION: SM03 LCVR CDR3

<400> SEQUENCE: 4

Gln Gln Gly Asn Thr Leu Pro Trp Thr
1               5

<210> SEQ ID NO 5
<211> LENGTH: 123
<212> TYPE: PRT
<213> ORGANISM: Artificial Sequence
<220> FEATURE:
<221> NAME/KEY: MISC_FEATURE
<222> LOCATION: (1)..(123)
<223> OTHER INFORMATION: SM03 HCVR

<400> SEQUENCE: 5

Gln Val Gln Leu Gln Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
        115                 120

<210> SEQ ID NO 6
<211> LENGTH: 5
<212> TYPE: PRT
<213> ORGANISM: Artificial Sequence
<220> FEATURE:
<221> NAME/KEY: MISC_FEATURE
<222> LOCATION: (1)..(5)
<223> OTHER INFORMATION: SM03 HCVR CDR1

<400> SEQUENCE: 6

Ile Tyr Asp Met Ser
1               5

<210> SEQ ID NO 7
<211> LENGTH: 17
<212> TYPE: PRT
<213> ORGANISM: Artificial Sequence
<220> FEATURE:
<221> NAME/KEY: MISC_FEATURE
<222> LOCATION: (1)..(17)
<223> OTHER INFORMATION: SM HCVR CDR2

<400> SEQUENCE: 7

Tyr Ile Ser Ser Gly Gly Gly Thr Thr Tyr Tyr Pro Asp Thr Val Lys
1               5                   10                  15

Gly

<210> SEQ ID NO 8
<211> LENGTH: 14
<212> TYPE: PRT

```
<213> ORGANISM: Artificial Sequence
<220> FEATURE:
<221> NAME/KEY: MISC_FEATURE
<222> LOCATION: (1)..(14)
<223> OTHER INFORMATION: SM03 VH CDR3

<400> SEQUENCE: 8

His Ser Gly Tyr Gly Ser Ser Tyr Gly Val Leu Phe Ala Tyr
1               5                   10

<210> SEQ ID NO 9
<211> LENGTH: 108
<212> TYPE: PRT
<213> ORGANISM: Artificial Sequence
<220> FEATURE:
<221> NAME/KEY: MISC_FEATURE
<222> LOCATION: (1)..(108)
<223> OTHER INFORMATION: SM06 LCVR

<400> SEQUENCE: 9

Asp Ile Gln Leu Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Val Glu Ile Lys Arg
            100                 105

<210> SEQ ID NO 10
<211> LENGTH: 123
<212> TYPE: PRT
<213> ORGANISM: Artificial Sequence
<220> FEATURE:
<221> NAME/KEY: MISC_FEATURE
<222> LOCATION: (1)..(123)
<223> OTHER INFORMATION: SM06 HCVR

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ile Tyr
            20                  25                  30

Asp Met Ser Trp Val Arg Gln Ala Pro Gly Lys Gly Leu Glu Trp Val
        35                  40                  45

Ala Tyr Ile Ser Ser Gly Gly Gly Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
        115                 120
```

<210> SEQ ID NO 11
<211> LENGTH: 279
<212> TYPE: PRT
<213> ORGANISM: Artificial Sequence
<220> FEATURE:
<221> NAME/KEY: MISC_FEATURE
<222> LOCATION: (1)..(279)
<223> OTHER INFORMATION: Sequence encompassing domains 2-4 of human CD22
      sequence

<400> SEQUENCE: 11

```
Arg Pro Phe Pro Pro His Ile Gln Leu Pro Glu Ile Gln Glu Ser
1               5                   10                  15

Gln Glu Val Thr Leu Thr Cys Leu Leu Asn Phe Ser Cys Tyr Gly Tyr
            20                  25                  30

Pro Ile Gln Leu Gln Trp Leu Leu Glu Gly Val Pro Met Arg Gln Ala
            35                  40                  45

Ala Val Thr Ser Thr Ser Leu Thr Ile Lys Ser Val Phe Thr Arg Ser
        50                  55                  60

Glu Leu Lys Phe Ser Pro Gln Trp Ser His His Gly Lys Ile Val Thr
65              70                  75                  80

Cys Gln Leu Gln Asp Ala Asp Gly Lys Phe Leu Ser Asn Asp Thr Val
                85                  90                  95

Gln Leu Asn Val Lys His Thr Pro Lys Leu Glu Ile Lys Val Thr Pro
            100                 105                 110

Ser Asp Ala Ile Val Arg Glu Gly Asp Ser Val Thr Met Thr Cys Glu
            115                 120                 125

Val Ser Ser Ser Asn Pro Glu Tyr Thr Thr Val Ser Trp Leu Lys Asp
        130                 135                 140

Gly Thr Ser Leu Lys Lys Gln Asn Thr Phe Thr Leu Asn Leu Arg Glu
145             150                 155                 160

Val Thr Lys Asp Gln Ser Gly Lys Tyr Cys Cys Gln Val Ser Asn Asp
                165                 170                 175

Val Gly Pro Gly Arg Ser Glu Glu Val Phe Leu Gln Val Gln Tyr Ala
            180                 185                 190

Pro Glu Pro Ser Thr Val Gln Ile Leu His Ser Pro Ala Val Glu Gly
            195                 200                 205

Ser Gln Val Glu Phe Leu Cys Met Ser Leu Ala Asn Pro Leu Pro Thr
        210                 215                 220

Asn Tyr Thr Trp Tyr His Asn Gly Lys Glu Met Gln Gly Arg Thr Glu
225             230                 235                 240

Glu Lys Val His Ile Pro Lys Ile Leu Pro Trp His Ala Gly Thr Tyr
                245                 250                 255

Ser Cys Val Ala Glu Asn Ile Leu Gly Thr Gly Gln Arg Gly Pro Gly
            260                 265                 270

Ala Glu Leu Asp Val Gln Tyr
            275
```

<210> SEQ ID NO 12
<211> LENGTH: 112
<212> TYPE: PRT
<213> ORGANISM: Artificial Sequence
<220> FEATURE:
<221> NAME/KEY: MISC_FEATURE
<222> LOCATION: (1)..(112)
<223> OTHER INFORMATION: LRID LCVR

<400> SEQUENCE: 12

```
Asp Ile Val Leu Thr Gln Thr Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Gly Gly Thr Lys Leu Gly Ile Lys Arg
            100                 105                 110
```

<210> SEQ ID NO 13
<211> LENGTH: 117
<212> TYPE: PRT
<213> ORGANISM: Artificial Sequence
<220> FEATURE:
<221> NAME/KEY: MISC_FEATURE
<222> LOCATION: (1)..(117)
<223> OTHER INFORMATION: LRID HCVR

<400> SEQUENCE: 13

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Thr His Trp Val Lys Gln Lys Pro Gly Gln Gly Leu Glu Trp Ile
        35                  40                  45

Gly Tyr Ile Asn Pro Tyr Ser Asp Gly Ser Tyr Asn Glu Lys Phe
    50                  55                  60

Lys Gly Lys Ala Thr Leu Thr Ser Asp Glu Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Lys Thr Glu Trp Phe Pro Tyr Trp Gly Gln Gly Thr Thr
            100                 105                 110

Val Thr Val Ser Ser
        115
```

<210> SEQ ID NO 14
<211> LENGTH: 776
<212> TYPE: PRT
<213> ORGANISM: Artificial Sequence
<220> FEATURE:
<221> NAME/KEY: MISC_FEATURE
<222> LOCATION: (1)..(776)
<223> OTHER INFORMATION: CD22-Glyco

<400> SEQUENCE: 14

```
Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45
```

-continued

```
Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
        355                 360                 365

Asn Gly Lys Glu Met Gln Gly Arg Thr Glu Glu Lys Val His Ile Pro
370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
        435                 440                 445

Pro Ser Val Thr Arg Tyr Glu Trp Lys Pro His Gly Ala Trp Glu Glu
450                 455                 460

Pro Ser Leu Gly Val Leu Lys Ile Gln Asn Val Gly Trp Asp Asn Thr
```

```
            465                 470                 475                 480
        Thr Ile Ala Cys Ala Ala Cys Asn Ser Trp Cys Ser Trp Ala Ser Pro
                        485                 490                 495

Val Ala Leu Asn Val Gln Tyr Ala Pro Arg Asp Val Arg Val Arg Lys
                        500                 505                 510

Ile Lys Pro Leu Ser Glu Ile His Ser Gly Asn Ser Val Ser Leu Gln
                        515                 520                 525

Cys Asp Phe Ser Ser Ser His Pro Lys Glu Val Gln Phe Phe Trp Glu
        530                 535                 540

Lys Asn Gly Arg Leu Leu Gly Lys Glu Ser Gln Leu Asn Phe Asp Ser
        545                 550                 555                 560

Ile Ser Pro Glu Asp Ala Gly Ser Tyr Ser Cys Trp Val Asn Asn Ser
                        565                 570                 575

Ile Gly Gln Thr Ala Ser Lys Ala Trp Thr Leu Glu Val Leu Tyr Ala
                        580                 585                 590

Pro Arg Arg Leu Arg Val Ser Met Ser Pro Gly Asp Gln Val Met Glu
                        595                 600                 605

Gly Lys Ser Ala Thr Leu Thr Cys Glu Ser Asp Ala Asn Pro Pro Val
        610                 615                 620

Ser His Tyr Thr Trp Phe Asp Trp Asn Asn Gln Ser Leu Pro Tyr His
        625                 630                 635                 640

Ser Gln Lys Leu Arg Leu Glu Pro Val Lys Val Gln His Ser Gly Ala
                        645                 650                 655

Tyr Trp Cys Gln Gly Thr Asn Ser Val Gly Lys Gly Arg Ser Pro Leu
                        660                 665                 670

Ser Thr Leu Thr Val Tyr Tyr Ser Pro Glu Thr Ile Gly Arg Arg Ala
                        675                 680                 685

Glu Pro Lys Ser Cys Asp Lys Thr His Thr Cys Pro Pro Cys Pro Gly
        690                 695                 700

Glu Arg Val Gln Leu Ala His His Phe Ser Glu Pro Glu Ile Thr Leu
        705                 710                 715                 720

Ile Ile Phe Gly Val Met Ala Gly Val Ile Gly Thr Ile Leu Leu Ile
                        725                 730                 735

Ser Tyr Gly Ile Arg Arg Leu Ile Lys Lys Ser Pro Ser Asp Val Lys
                        740                 745                 750

Pro Leu Pro Ser Pro Asp Thr Asp Val Pro Leu Ser Ser Val Glu Ile
                        755                 760                 765

Glu Asn Pro Glu Thr Ser Asp Gln
        770                 775

<210> SEQ ID NO 15
<211> LENGTH: 724
<212> TYPE: PRT
<213> ORGANISM: Artificial Sequence
<220> FEATURE:
<221> NAME/KEY: MISC_FEATURE
<222> LOCATION: (1)..(724)
<223> OTHER INFORMATION: CD22-GPI

<400> SEQUENCE: 15

Met His Leu Leu Gly Pro Trp Leu Leu Leu Leu Val Leu Glu Tyr Leu
1               5                   10                  15

Ala Phe Ser Asp Ser Ser Lys Trp Val Phe Glu His Pro Glu Thr Leu
                20                  25                  30

Tyr Ala Trp Glu Gly Ala Cys Val Trp Ile Pro Cys Thr Tyr Arg Ala
            35                  40                  45
```

```
Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
    290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
        355                 360                 365

Asn Gly Lys Glu Met Gln Gly Arg Thr Glu Glu Lys Val His Ile Pro
    370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
        435                 440                 445

Pro Ser Val Thr Arg Tyr Glu Trp Lys Pro His Gly Ala Trp Glu Glu
    450                 455                 460
```

```
Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
            515                 520                 525

Cys Asp Phe Ser Ser Ser His Pro Lys Glu Val Gln Phe Phe Trp Glu
530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
            580                 585                 590

Pro Arg Arg Leu Arg Val Ser Met Ser Pro Gly Asp Gln Val Met Glu
            595                 600                 605

Gly Lys Ser Ala Thr Leu Thr Cys Glu Ser Asp Ala Asn Pro Pro Val
610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
            660                 665                 670

Ser Thr Leu Thr Ala Glu Pro Lys Ser Cys Asp Lys Thr His Thr Cys
            675                 680                 685

Pro Pro Cys Pro Leu Thr Thr Ser Gly Ile Val Thr Met Ser His Gln
690                 695                 700

Ala Leu Gly Phe Thr Leu Thr Gly Leu Leu Gly Thr Leu Val Thr Met
705                 710                 715                 720

Gly Leu Leu Thr

<210> SEQ ID NO 16
<211> LENGTH: 13
<212> TYPE: PRT
<213> ORGANISM: Artificial Sequence
<220> FEATURE:
<221> NAME/KEY: MISC_FEATURE
<222> LOCATION: (1)..(13)
<223> OTHER INFORMATION: epitope of domain 2 of CD22

<400> SEQUENCE: 16

Cys Leu Leu Asn Phe Ser Cys Tyr Gly Tyr Pro Ile Gln
1               5                   10

<210> SEQ ID NO 17
<211> LENGTH: 22
<212> TYPE: PRT
<213> ORGANISM: Artificial Sequence
<220> FEATURE:
```

```
<221> NAME/KEY: MISC_FEATURE
<222> LOCATION: (1)..(22)
<223> OTHER INFORMATION: epitope of domain 2 of CD22

<400> SEQUENCE: 17

Val Phe Thr Arg Ser Glu Leu Lys Phe Ser Pro Gln Trp Ser His His
1               5                   10                  15

Gly Lys Ile Val Thr Cys
            20
```

FUSION PROTEINS COMPRISING EXTRACELLULAR DOMAIN OF HUMAN CD22

CROSS-REFERENCE TO RELATED APPLICATIONS

This application is a National Stage of International Application No. PCT/CN2019/111886, filed Oct. 18, 2019, which claims the benefit of U.S. Provisional Patent Application No. 62/747,581, filed Oct. 18, 2018 and U.S. Provisional Patent Application No. 62/775,631, filed Dec. 5, 2018. The entire contents of these preceding applications and publications are hereby incorporated by reference herein.

BACKGROUND OF THE PRESENT INVENTION

Autoimmune diseases are a result of abnormal immune responses to normal body parts. The causes leading to the conditions are generally unknown. Currently, treatments on a variety of autoimmune diseases are directed towards pro-inflammatory factors (e.g. anti-TNFα antibodies), or the control of the release of these cytokines (e.g. JAK inhibitors).

Although the introduction of anti-TNF and anti-IL1 combination therapy with traditional disease-modifying drugs (DMARDs) have improved treatments to autoimmune diseases, there remains substantial number of patients that either fail to respond to the treatment options or eventually become refractory to the treatment.

Accordingly, there is a great need for new treatments for auto-immune diseases. Furthermore, there is a need for new methods for identifying new treatments that more specifically target the root causes of the auto-immune diseases, thereby more specifically targeting the symptoms without impacting the immune system in general.

SUMMARY OF THE PRESENT INVENTION

The present invention also provides methods for biweekly multiple times in multiple cycles each spanning 12 weeks dosing regimens in two cycles for the treatment of autoimmune disorders by interfering with B cells via B-cell specific anti-CD22 antibodies. Biweekly dosing has many advantages over weekly dosing including, but not limited to, a lower number of total injections, increased patient compliances (i.e., due to less frequent injections), and less cost to the patient as well as the health care provider.

The present invention also provides methods of treating autoimmune diseases arising from loss of regulatory and/or inhibitory functions of B cells, including different B cell subtypes such as regulatory B cells (Breg), due to insufficient conversion of CD22 and/or other Siglecs binding to their ligands from cis- to trans-configuration or unavailability of free ligand binding sites on human CD22 and/or other Siglecs due to these sites being "masked" by cis-ligand binding. Preferably, the anti-Siglecs antibodies are anti-CD22 antibodies that target epitopes residing in preferably the domain 2 of human CD22 with high affinity, and their binding on to human CD22 will result in the disruption of the homomultimeric structure of human CD22 while sterically hinder the re-engagement of human CD22 ligand binding in cis; the availability of ligand-binding sites on human CD22 for trans-binding is further improved when human CD22 is induced to internalize upon binding to the anti-CD22 antibodies. Internalization will bring the cis-binding CD22 into the endosome/lysosome where the low pH environment will free up all ligand engagement; resurfaced CD22 (via recycling) will be bound by the anti-CD22 antibody (for those already bound by the anti-CD22 antibody during the process or internalization, the recycled CD22 will remain bound by the anti-CD22 antibody upon resurfacing), preventing further cis-ligand binding and making more CD22 available for trans-ligand binding. Trans-binding of CD22 to the ligands on other hematopoietic cells is important for the induction and maintenance of tolerance for autoantigens.

This invention also provides methods for identifying antibodies specific for human CD22 or other Siglec that work to restore the immune inhibitory functions of B cells for self-tissues and methods for using these antibodies to restore immune tolerance to self-tissue by allowing CD22 engagement with ligands on other hematopoietic cells. The antibodies identified are used for treating disorders in which over-reactive immune system against its own tissues is detrimental. The methods include administering biweekly, intravenous injection of antibodies to a subject. The antibodies preferably are recombinant antibodies (chimeric or framework-patched/humanized) that specifically bind to human Siglecs, preferably human CD22, and more preferably, to domain 2 of human CD22, and most preferably to a conformational discontinuous epitope located in domain 2 of human CD22.

This invention further provides methods for treating disorders in which over reactive immune activities against self-tissues is detrimental. These methods include utilizing a combination therapy wherein human antibodies are administered to a subject with another therapeutic agent, such as one or more additional antibodies that bind other targets (e.g., antibodies that bind other cytokines, including IL1β, IL6, IL12, IL13, IL17A, IL20, IL22, IL23, TNFα, and other cell surface receptors such as IL6 receptor, CD4, CD5, CD20, CD28, CD147, CD154 (CD40L), GMCSF-receptor), one or more cytokines, soluble TNFα receptor and/or one or more chemical agents that inhibit production and activities of the aforementioned cytokines and/or surface receptors, for example and preferably, methotrexate, and/or JAK (JAK1, 2, 3 and tyrosine kinase 2) inhibitors. The antibodies are preferably recombinant chimeric or framework-patched (humanized) antibodies that specifically bind to human CD22. The antibodies of the invention are characterized by binding to human CD22 with high affinity at a specific epitope residing in the domain 2 of human CD22 and by inhibiting B cell activities through CD22-induced cellular inactivation and possibly mild cytotoxicity.

The antibodies can be full-length (e.g., an IgG1 or IgG4 antibody) or can comprise only an antigen-binding portion (e.g., a Fab, Fab', F(ab)'$_2$, scFv fragment or single domain).

In another embodiment, the recombinant antibody is SM03 (chimeric) or SM06 (humanized version by Framework patching), and has a light chain CDR3 domain comprising the amino acid sequence of SEQ ID NO: 004 and a heavy chain CDR3 domain comprising the amino acid sequence of SEQ ID NO: 008 (set forth in Appendix 01). In some embodiments, the SM03 antibody has a light chain variable region (LCVR) comprising the amino acid sequence of SEQ ID NO: 001 and a heavy chain variable region (HCVR) comprising the amino acid sequence of SEQ ID NO: 005; whereas the SM06 antibody has a light chain variable region (LCVR) comprising the amino acid sequence of SEQ ID NO: 009 and a heavy chain variable region (HCVR) comprising the amino acid sequence of SEQ ID NO: 010. These antibodies are described in Chinese Pat. No. ZL 031 23054.7 & ZL 011 44894.6 and U.S. Pat. Nos. 7,321,026 B2 & 7,338,659 B2, incorporated in its entirety herein by reference.

In one embodiment, the invention provides methods for identifying and evaluating antibodies that can efficiently disrupt cis-binding human CD22 for trans-ligand binding for the induction of immune tolerance or inhibitory activity for self-antigens. The methods include the generation of cell lines expressing extracellular human CD22 that do not have a2-6-linked sialic acid (2,6Sia) residues for cis-ligation (only trans-ligation to other cells or exogenous multimeric ligands are possible), and cell lines that express extracellular CD22 in cis-configuration, and the use of these cell lines and an exogenous multimeric ligands such as FITC- or biotin-conjugated polyacrylamide substituted with a2-6-sialyllactose (6'PAA-FITC and 6'PAA-B) for evaluating antibodies against human CD22 that will disrupt cis-ligand binding and encourage binding to the exogenous synthetic multimeric ligands in trans. Those skilled in the art can apply the same approach for the identification and evaluation of other antibodies that can efficiently disrupt cis-ligation of other Siglec antigens.

In another embodiment, the invention provides methods of treating disorders in which over active or uncontrolled immune (or autoimmune) activity is detrimental. In another embodiment, the invention provides methods of employing Siglec specific antibodies, specifically antibodies targeting human CD22 at epitopes that disrupt cis-ligand binding, to treat disorders in which over active or uncontrolled immune (or autoimmune) activity is detrimental. These methods include inhibiting or modifying B cell activity by intravenous, subcutaneous, intraperitoneal or oral administration of anti-Siglec, specifically anti-CD22 antibodies in multiple times in multiple cycles such that the disorder is treated. The disorder can be, for example, an autoimmune disease (e.g., rheumatoid arthritis, lupus erythematosus, spondylitis, sjögren's syndrome, allergy, multiple sclerosis, autoimmune diabetes, autoimmune uveitis and nephrotic syndrome), a malignancy, transplant rejection or graft-versus-host disease, and intestinal disorder. In some embodiments, the disorder can be autoimmunity disease such as rheumatoid arthritis (RA), rheumatoid spondylitis, systemic lupus erythematosus (SLE), multiple sclerosis (MS), autoimmune diabetes, Sjogren's syndrome or disease, psoriasis, inflammatory bowel disease, Graves' disease, diabetes mellitus type 1, celiac diseases, osteoarthritis and gouty arthritis, allergy, autoimmune uveitis, nephrotic syndrome, pemphigus vulgaris, Alzheimer's disease, Behcet diseases (BD) and/or B cell malignancy. In some embodiments, the administration is biweekly and the cycles each span 12 weeks.

In another embodiment, the invention provides methods of treating disorders in which over active or uncontrolled immune system (or autoimmune) activity is detrimental. These methods include inhibiting or modifying the activity and/or number of circulating CD22+ cells by intravenous, subcutaneous, intraperitoneal or oral administration of antibodies specific for the epitope of Siglecs, such as human CD22 antigen, that will disrupt the cis-ligand binding of the Siglecs such as human CD22 and methotrexate such that the disorder is treated. In one aspect, the antibody is an anti-CD22 antibody. In another aspect, the antibody is administered together with an anti-Siglec or anti-CD22 antibody. In another aspect, methotrexate is administered prior to the administration of an anti-Siglec or anti-CD22 antibody. In still another aspect, methotrexate is administered subsequent to the administration of an anti-Siglec or anti-CD22 antibody.

In another embodiment, the anti-Siglec or anti-CD22 antibody used to treat disorders in which over active immune or uncontrolled immune system (or autoimmune) activity is detrimental is a chimeric and/or framework-patched (humanized) anti-CD22 antibody. Preferably, treatment occurs by the biweekly, intravenous administration of an isolated chimeric and/or framework-patched (humanized) antibody, or an antigen-binding portion thereof, in multiple times in multiple cycles each spanning 12 weeks; more preferably, treatment occurs by the biweekly, intravenous administration of an isolated chimeric and/or framework-patched (humanized) antibody, or an antigen-binding portion thereof, in two times in two cycles each spanning 12 week; even more preferably, treatment occurs by the biweekly, intravenous administration of an isolated chimeric and/or framework-patched (humanized) antibody, or an antigen-binding portion thereof, in three times in two cycles each spanning 12 weeks. Thereafter and in all treatment regimens, maintenance of treatment response occurs by single intravenous administration of an isolated chimeric and/or framework-patched (humanized) antibody every other 6 weeks. The antibody or antigen-binding portion thereof preferably binds to the second N-terminal domain (domain 2) of the CD22 antigen, and the binding will disrupt the cis-ligand binding homomultimeric CD22 configuration and free up more ligand binding sites for trans-ligation with ligands from other immune cells or self-tissue expressing the terminal sequence N-acetylneuraminic acid a(2-6) galactose (NeuAc-a(2-6)Gal) such that the B cells will exert inhibitory or regulatory control on BCR targeting the autoantigen on the self-tissues; more preferably, interacts with the domain 2 sequence $_{161}$CLLNFSCYGYPIQ$_{171}$, even more preferably, interacts with the discontinuous conformational epitope in the same domain containing the sequences $_{161}$CLLNFSCYGYPIQ$_{173}$ & $_{198}$VFTRSELKFSPQWSHHGKIVTC$_{219}$; and further more preferably dissociates from human CD22 with a Kd of $1.22 \times 10^{-8}$ M or less and a kd of 0.137 s$^{-1}$ or less, and even further more preferably, dissociates from human CD22 with a Kd of $1.22 \times 10^{-9}$ M or less and a kd of 0.0137 RU s$^{-1}$ or less, both determined by surface plasmon resonance. Moreover, the antibody or antigen-binding portion thereof binds specifically to an anti-idiotype antibody against the antigen binding site (ABS) of the anti-CD22 antibody, preferably against the ABS of SM03 and SM06 (the anti-idiotype antibody against SM03/SM06 is called LRID) (Zhao et al. (2014) *PLOS ONE* 9(5): e96697; Leung et al. (2015) MAbs 7(1):66-76), with an EC$_{50}$ in the range of 0.799 μg/ml or less, in some embodiments, in the range of 0.0799 μg/ml or less. In some embodiments, the antibody or antigen-binding portion thereof induces complement dependent cell cytotoxicity (CMC) activity against a recombinant engineered surrogate target cell line expressing surface-bound anti-idiotype binding moiety against the anti-CD22 antibody with an EC$_{50}$ in the range of 1.658 μg/ml or less, or in some embodiments, in the range of 0.1658 μg/m/or less.

In another embodiment, the invention provides methods of treating disorders in which over active immune system (or autoimmune) activity is detrimental by the administration to the subject a chimeric or framework-patched (humanized) antibody, or antigen-binding portion thereof, in multiple times in multiple cycles. The antibody or antigen-binding portion thereof comprises one or more of the following characteristics:

a) Binds to the second N-terminal domain (domain 2) of the human CD22 antigen, preferably, interacts with the domain 2 sequence $_{161}$CLLNFSCYGYPIQ$_{171}$. In some embodiments, interacts with the discontinuous conformational epitope in the same domain containing the sequences $_{161}$CLLNFSCYGYPIQ$_{173}$ & $_{198}$VFTRSELKFSPQWSHHGKIVTC$_{219}$. In some embodiments, the binding will disrupt the cis-ligand binding homomultimeric CD22 configuration and free up more ligand binding sites for trans-ligation with ligands from other immune cells or self-tissue expressing the terminal sequence N-acetylneuraminic acid a(2-6) galactose (NeuAc-a(2-6)Gal) such that the B cells will exert inhibitory or regulatory control on B cell receptor (BCR) targeting the autoantigen on the self-tissues;

b) Induces CD22-antibody complex internalization upon binding via a recycling pathway, resulting in the disruption of cis-ligand binding under the acidic environment of the endosome/lysozyme, including human CD22 molecules that are not bound to the antibody but get internalized alongside with other cis-bound CD22-antibody complexes, and the resurfacing of ligand-free CD22 for ligand-binding in trans;

c) Binds to the idiotype of LRID antibody, which is a murine antibody specific for the antigen binding site (ABS) of SM03 and SM06 with an $EC_{50}$ in the range of 79.9 ng/ml or less d) Induces complement-mediated cell cytotoxicity (CMC) activity against a recombinant engineered surrogate target cell line expressing surface-bound anti-idiotype binding fragment (Fab fusion) with an $EC_{50}$ in the range of 0.1509 μg/ml or less e) Dissociates from human CD22 a kd of 0.0137 RU $s^{-1}$ or less, as determined by surface plasmon resonance f) Has a light chain CDR3 domain comprising the amino acid sequence of SEQ ID 004, or modified from SEQ ID NO: 004 via conservative amino acid substitution at positions, or by replacing the SEQ ID No: 004 with known human LCVR CDR3 sequence from available human antibody database (e.g. Kabat's Database) using methods of CDR humanization as described in Chinese Pat. No. ZL200880024788.2, g) Has a heavy chain CDR3 domain comprising the amion acid sequence of SEQ ID NO: 008, or modified from SEQ ID NO: 008 via conservative amino acid substitution at corresponding positions, or by replacing the SEQ ID No: 008 with known human HCVR CDR3 sequence from available human antibody database (e.g. Kabat's Database) using methods of CDR humanization as described in Chinese Pat. No. ZL200880024788.2, which is incorporated by reference herein.

More preferably, the antibody, or antigen-binding portion thereof, binds to human CD22 at the domain 2 discontinuous conformational epitope with a Kd of $1.22\times10^{-8}$ M or less, even more preferably, with a Kd of $1.22\times10^{-9}$ M or less. Still more preferably, the antibody, or antigen-binding portion thereof, dissociates from human CD22 at the domain 2 discontinuous conformational epitope with a kd of 0.137 RU $s^{-1}$ or less, and still even more preferably, dissociates from human CD22 at the domain 2 discontinuous conformational epitope with a kd of 0.0137 RU $s^{-1}$ or less.

In yet another embodiment, the invention provides methods of treating disorders in which over active immune system (or autoimmune) activity is detrimental. These methods include a biweekly, intravenous administration to the subject a chimeric or framework-patched (humanized) antibody, or an antigen-binding portion thereof, in multiple times in multiple cycles each spanning 12 weeks. The antibody or antigen-binding portion thereof preferably contains an LCVR having CDR3 domain comprising the amino acid sequence of SEQ ID NO: 004, or modified from SEQ ID NO: 004 by conservative substitution at corresponding positions, or replaced with known human LCVR CDR3 sequence from available human antibody database (e.g. Kabat's database) using methods of CDR humanization, the method of which was described in Chinese Pat. No. ZL200880024788.2, which is incorporated by reference herein; and with an HCVR having a CDR3 domain comprising the amino acid sequence of SEQ ID NO: 008, or modified from SEQ ID NO: 008 by conservative substitution at corresponding positions, or replaced with known human HCVR CDR3 sequence from available human antibody database (e.g., Kabat's database) using methods of CDR humanization. More preferably, the LCVR further has a CDR2 domain comprising the amino acid sequence of SEQ ID NO: 003 and the HCVR further has a CDR2 domain comprising the amino acid sequence of SEQ ID NO: 007. Still more preferably, the LCVR further has CDR1 domain comprising the amino acid sequence of SEQ ID NO: 002 and the HCVR has a CDR1 domain comprising the amino acid sequence of SEQ ID NO: 006.

In still another embodiment, the invention provides methods of treating disorders in which over active immune system (or autoimmune) activity is detrimental by intravenously administering to the subject, biweekly, an isolated chimeric or framework-patched (humanized) antibody, or an antigen binding portion thereof, in multiple times in multiple cycles each spanning 12 weeks. The antibody or antigen-binding portion thereof preferably contains an LCVR comprising the amino acid sequence of SEQ ID NO: 001 or SEQ ID NO: 009, and an HCVR comprising the amino acid sequence of SEQ ID NO: 005 or SEQ ID NO: 010. In certain embodiments, the antibody has an IgG1 heavy chain constant region or an IgG4 heavy chain constant region. In yet other embodiments, the antibody is a Fab fragment, an Fab' fragment, an F(ab')s fragment or a single chain Fv fragment.

Still another aspect of the invention pertains to kits containing a formulation comprising a pharmaceutical composition. The kits comprise an anti-CD22 antibody and a pharmaceutically acceptable carrier. The kits contain instructions for biweekly intravenous dosing of the pharmaceutical composition for the treatment of a disorder in which the administration of an anti-CD22 antibody is beneficial. In another aspect, the invention pertains to kits containing a formulation comprising a pharmaceutical composition, further comprising an anti-CD22 antibody, methotrexate, and a pharmaceutically acceptable carrier. The kits contain instructions for intravenous dosing of the pharmaceutical composition for the treatment of a disorder in which the administration of an anti-CD22 antibody is beneficial.

Another embodiment provides a method of employing techniques of full discontinuous epitope mapping to provide the specific epitope against which SM03 (and SM06) binds. Yet another embodiment provides a method of restoring the immune regulatory function of human CD22 in the attenuation of immune response or inhibition of autoimmunity against autoantigens, comprising the step of binding or contacting SM03 or SM06 to human CD22 in a disruptive manner to release the sialic acid binding site of human CD22 from the cis-binding configuration to the trans-ligand formation. In some embodiments, SM03 or SM06 interacts with the antigen with high affinity.

In another aspect, provided is a method for treating rheumatoid arthritis in a human subject, comprising administering intravenously (or subcutaneously) to a human subject having rheumatoid arthritis anti-CD22 antibodies in two cycles in which the first cycle begins at week 0 and the second cycle begins at week 12; whereas each cycle encompasses the administration of either two infusions or three infusions in which each infusion contains a total body dose of 600 mg and each infusion is two weeks apart, wherein the anti-CD22 antibody comprises an IgG1 heavy chain constant region and binds to a discontinuous conformational epitope containing the sequence $_{161}$CLLNFSCYGYPIQ$_{173}$ & $_{198}$VFTRSELKFSPQWSHHGKIVTC$_{219}$ within the domain 2 of the human CD22 antigen.

In another aspect, provided is a method for treating rheumatoid arthritis in a human subject, comprising administering intravenously (or subcutaneously) to a human subject having rheumatoid arthritis anti-CD22 antibodies in two cycles in which the first cycle begins at week 0 and the second cycle begins at week 12; whereas each cycle encompasses the administration of either two infusions or three infusions in which each infusion contains a total body dose of 600 mg and each infusion is two weeks apart, wherein the anti-CD22 antibody comprises an IgG1 heavy chain constant region and binds to a discontinuous conformational epitope containing the sequence $_{161}$CLLNFSCYGYPIQ$_{173}$ & $_{198}$VFTRSELKFSPQWSHHGKIVTC$_{219}$ within the domain 2 of the human CD22 antigen; wherein the anti-CD22 antibody binds to the idiotope of an anti-idiotype antibody (LRID) with a variable light ("VL") chain region having the amino acid sequence of SEQ ID NO: 012, and a variable heavy ("VH") chain region having the amino acid sequence of SEQ ID NO: 013.

In another aspect, provided is a method for treating rheumatoid arthritis in a human subject, comprising administering intravenously (or subcutaneously) to a human subject having rheumatoid arthritis anti-CD22 antibodies in two cycles in which the first cycle begins at week 0 and the second cycle begins at week 12; whereas each cycle encompasses the administration of either two infusions or three infusions in which each infusion contains a total body dose of 600 mg and each infusion is two weeks apart, wherein the anti-CD22 antibody comprises an IgG1 heavy chain constant region and binds to a discontinuous conformational epitope containing the sequence $_{161}$CLLNFSCYGYPIQ$_{173}$ & $_{198}$VFTRSELKFSPQWSHHGKIVTC$_{219}$ within the domain 2 of the human CD22 antigen; wherein the anti-CD22 antibody binds to the idiotope of an anti-idiotype antibody (LRID) with a variable light ("VL") chain region having the amino acid sequence of SEQ ID NO: 012, and a variable heavy ("VH") chain region having the amino acid sequence of SEQ ID NO: 013; and wherein the anti-CD22 antibody can induce complement mediated cell cytotoxicity (CMC) and antibody-dependent cell cytotoxicity (ADCC) against a surrogate target cell that expresses surface bound anti-idiotype antibody Fabs having a VL of SEQ ID NO: 012 and a VH of SEQ ID NO: 013.

In another aspect, provided is a method for treating rheumatoid arthritis in a human subject, comprising administering intravenously (or subcutaneously) to a human subject having rheumatoid arthritis anti-CD22 antibodies in two cycles in which the first cycle begins at week 0 and the second cycle begins at week 12; whereas each cycle encompasses the administration of either two infusions or three infusions in which each infusion contains a total body dose of 600 mg and each infusion is two weeks apart, wherein the anti-CD22 antibody comprises an IgG1 heavy chain constant region and binds to a discontinuous conformational epitope containing the sequence $_{161}$CLLNFSCYGYPIQ$_{173}$ & $_{198}$VFTRSELKFSPQWSHHGKIVTC$_{219}$ within the domain 2 of the human CD22 antigen; wherein the anti-CD22 antibody binds to the idiotope of an anti-idiotype antibody (LRID) with a variable light ("VL") chain region having the amino acid sequence of SEQ ID NO: 012, and a variable heavy ("VH") chain region having the amino acid sequence of SEQ ID NO: 013; and wherein the anti-CD22 antibody can induce complement mediated cell cytotoxicity (CMC) and antibody-dependent cell cytotoxicity (ADCC) against a surrogate target cell that expresses surface bound anti-idiotype antibody Fab having a VL of SEQ ID NO: 012 and a VH of SEQ ID NO: 013, wherein the anti-CD22 antibody comprises an IgG1 heavy chain constant region; a variable light ("VL") chain region comprising a CDR1 having the amino acid sequence of SEQ ID NO: 002, a CDR2 having the amino acid sequence of SEQ ID NO: 003, and a CDR3 having the amino acid sequence of SEQ ID NO: 004; and a variable heavy ("VH") chain region comprising a CDR1 having the amino acid sequence of SEQ ID NO: 006, a CDR2 having the amino acid sequence of SEQ ID NO: 007 and a CDR3 having the amino acid sequence of SEQ ID NO: 008.

In another embodiment, the VL chain region of the anti-CD22 antibody has the amino acid sequence of SEQ ID NO: 001 (SM03) and the VH chain region of the anti-CD22 antibody has the amino acid sequence of SEQ ID NO: 005.

In another embodiment, the VL chain region of the anti-CD22 antibody has the amino acid sequence of SEQ ID NO: 009 (SM06) and the VH chain region of the anti-CD22 antibody has the amino acid sequence of SEQ ID NO: 010.

In another embodiment, the anti-CD22 antibody is administered for a period of at least 24 weeks.

In another aspect, provided is a method for treating rheumatoid arthritis in a human subject, consisting of administering intravenously to a human subject having rheumatoid arthritis a composition comprising 600 mg of a human anti-CD22 antibody once every two weeks for a time period sufficient to treat the rheumatoid arthritis, wherein the anti-CD22 antibody comprises an IgG1 heavy chain constant region and binds to a discontinuous conformational epitope containing the sequence $_{161}$CLLNFSCYGYPIQ$_{173}$ & $_{198}$VFTRSELKFSPQWSHHGKIVTC$_{219}$ within the domain 2 of the human CD22 antigen; wherein the anti-CD22 antibody binds to the idiotope of an anti-idiotype antibody (LRID) with a variable light ("VL") chain region having the amino acid sequence of SEQ ID NO: 012, and a variable heavy ("VH") chain region having the amino acid sequence of SEQ ID NO: 013; and wherein the anti-CD22 antibody can induce complement mediated cell cytotoxicity (CMC) and antibody-dependent cell cytotoxicity (ADCC) against a surrogate target cell that expresses surface bound anti-idiotype antibody Fab having a VL of SEQ ID NO: 012 and a VH of SEQ ID NO: 013, wherein the anti-CD22 antibody comprises an IgG1 heavy chain constant region; a variable light ("VL") chain region comprising a CDR1 having the amino acid sequence of SEQ ID NO: 002, a CDR2 having the amino acid sequence of SEQ ID NO: 003, and a CDR3 having the amino acid sequence of SEQ ID NO: 004; and a variable heavy ("VH") chain region comprising a CDR1 having the amino acid sequence of SEQ ID NO: 006, a CDR2 having the amino acid sequence of SEQ ID NO: 007 and a CDR3 having the amino acid sequence of SEQ ID NO: 008 and wherein the human anti-CD22 antibody is administered in the form of a pharmaceutically acceptable composition.

In another aspect, provided is a method of treating rheumatoid arthritis in a subject in need thereof, comprising administering to the subject a therapeutically effective amount of an anti-CD22 antibody, wherein
  (a) the anti-CD22 antibody is administered in at least two cycles;
  (b) each cycle comprises two or more doses; and
  (c) each dose is administered biweekly.

In another embodiment, each cycle is 6-12 weeks long and comprises two or three doses.

In another embodiment, each cycle is 12 weeks long.

In another embodiment, the first dose of each cycle is administered on day 0 of the cycle.

In another embodiment, each dose is about 500 mg-750 mg. In another embodiment, each dose is 600 mg.

In another embodiment, each cycle comprises at least two doses of 600 mg each, totaling 1200 mg administered over 4 weeks.

In another embodiment, each cycle comprises at least three doses of 600 mg each, totaling 1,800 mg administered over 6 weeks.

In another embodiment, the anti-CD22 antibody is administered intravenously or subcutaneously.

In another embodiment, biweekly is every 9-19 days, 11-17 days, 13-15 days, or 14 days.

In another embodiment, biweekly is every 14 days.

In another embodiment, each cycle is the same length of time and has the same amount of anti-CD22 antibody administered per cycle.

In another embodiment, the anti-CD22 antibody is administered in two cycles, wherein each cycle is 12 weeks long and the amount of anti-CD22 antibody administered per cycle is 1200 mg or 1800 mg.

In another embodiment, the amount of anti-CD22 antibody administered per cycle is two or three doses.

In another embodiment, the first cycle begins at week 0 and the second cycle begins at week 12.

In another embodiment, the anti-CD22 antibody binds to two discontinuous sequences of an epitope of CD22 antigen located in domain 2 of the CD22 antigen.

In another embodiment, the two discontinuous sequences comprise CLLNFSCYGYPIQ and VFTRSELKFSPQWSHHGKIVTC. In another embodiment, the two discontinuous sequences are at least 95, 97, 98 or 99% homologous to CLLNFSCYGYPIQ and VFTRSELKFSPQWSHHGKIVTC, respectively. In another embodiment, the two discontinuous sequences are CLLNFSCYGYPIQ and VFTRSELKFSPQWSHHGKIVTC, respectively.

In another embodiment, the anti-CD22 antibody comprises a constant region of IgG1 heavy chain and a constant region of kappa light chain.

In another embodiment, the anti-CD22 antibody binds to an idiotope of an anti-idiotype antibody with a variable light chain region comprising an amino acid sequence of SEQ ID NO: 012, and a variable heavy chain region comprising an amino acid sequence of SEQ ID NO: 013. In another embodiment, the anti-CD22 antibody binds to an idiotope of an anti-idiotype antibody with a variable light chain region comprising an amino acid sequence being at least 95, 96, 97, 98 or 99% homologous to SEQ ID NO: 012, and a variable heavy chain region comprising an amino acid sequence being at least 95, 96, 97, 98 or 99% homologous to SEQ ID NO: 013.

In another embodiment, the anti-CD22 antibody comprises a variable light chain region which comprises an amino acid sequence of SEQ ID NO: 002, an amino acid sequence of SEQ ID NO: 003, and an amino acid sequence of SEQ ID NO: 004; and wherein the anti-CD22 antibody comprises a variable heavy chain region which comprises an amino acid sequence of SEQ ID NO: 006, an amino acid sequence of SEQ ID NO: 007, and an amino acid sequence of SEQ ID NO: 008. In another embodiment, the anti-CD22 antibody comprises a variable light chain region which comprises an amino acid sequence being at least 95, 96, 97, 98 or 99% homologous to SEQ ID NO: 002, an amino acid sequence being at least 95, 96, 97, 98 or 99% homologous to SEQ ID NO: 003, and an amino acid sequence being at least 95, 96, 97, 98 or 99% homologous to SEQ ID NO: 004; and wherein the anti-CD22 antibody comprises a variable heavy chain region which comprises an amino acid sequence being at least 95, 96, 97, 98 or 99% homologous to SEQ ID NO: 006, an amino acid sequence being at least 95, 96, 97, 98 or 99% homologous to SEQ ID NO: 007, and an amino acid sequence being at least 95, 96, 97, 98 or 99% homologous to SEQ ID NO: 008.

In another embodiment, the anti-CD22 antibody comprises a variable light chain region which comprises an amino acid sequence of SEQ ID NO: 001, and the anti-CD22 antibody comprises a variable heavy chain region which comprises an amino acid sequence of SEQ ID NO: 005. In another embodiment, the anti-CD22 antibody comprises a variable light chain region which comprises an amino acid sequence being at least 95, 96, 97, 98 or 99% homologous to SEQ ID NO: 001, and the anti-CD22 antibody comprises a variable heavy chain region which comprises an amino acid sequence being at least 95, 96, 97, 98 or 99% homologous to SEQ ID NO: 005.

In another embodiment, the anti-CD22 antibody comprises a variable light chain region which comprises an amino acid sequence of SEQ ID NO: 009, and the anti-CD22 antibody comprises a variable heavy chain region which comprises an amino acid sequence of SEQ ID NO: 010. In another embodiment, the anti-CD22 antibody comprises a variable light chain region which comprises an amino acid sequence being at least 95, 96, 97, 98 or 99% homologous to SEQ ID NO: 009, and the anti-CD22 antibody comprises a variable heavy chain region which comprises an amino acid sequence being at least 95, 96, 97, 98 or 99% homologous to SEQ ID NO: 010.

In another embodiment, the subject is human.

In another embodiment, the anti-CD22 antibody is selected from a group consisting of SM03, SM06 and a combination thereof.

In another embodiment, the subject has rheumatoid arthritis but has insufficient response or tolerability to methotrexate.

In another embodiment, the method further comprising administering an additional therapeutic agent for treating rheumatoid arthritis.

In another aspect, provided is a method of treating rheumatoid arthritis in a subject in need thereof, comprising administering an effective amount of an anti-CD22 antibody to the subject. In another embodiment, the effective amount is about 1,200 mg to 1,800 mg.

In another embodiment, the anti-CD22 antibody is administered to the subject intravenously or subcutaneously.

In another embodiment, the anti-CD22 antibody binds to two discontinuous sequences of an epitope of CD22 antigen located in domain 2 of the CD22 antigen.

In another embodiment, the two discontinuous sequences comprise CLLNFSCYGYPIQ and VFTRSELKFSPQWSHHGKIVTC. In another embodiment, the two discontinuous sequences are at least 95, 96, 97, 98 or 99% homologous to CLLNFSCYGYPIQ and VFTRSELKFSPQWSHHGKIVTC, respectively. In another embodiment, the two discontinuous sequences are CLLNFSCYGYPIQ and VFTRSELKFSPQWSHHG-KIVTC, respectively.

In another embodiment, the anti-CD22 antibody is selected from a group consisting of SM03, SM06 and a combination thereof.

In some embodiments, the methods described further comprising administering an additional therapeutic agent for treating rheumatoid arthritis.

In another embodiment, the additional therapeutic agent is selected from an immune system suppressant, an agent against immune cell antigens, an anti-inflammatory agent, a steroid or a kinase inhibitor.

In another embodiment, the immune system suppressant is selected from methotrexate; the anti-inflammatory agent is selected from an anti-TNF agent, anti-IL17 agent, anti-IL1, anti-IL12, anti-IL23, or anti-IL6 agent; and the kinase inhibitors is selected from an agent that inhibits JAK, BTK and the agent against immune cell antigens is an anti-CD20 antibody, anti-BLys antibody, anti-APRIL antibody, anti-CD40L(CD154), anti-GMCSF or an anti-GMCSF receptor.

In another embodiment, the disease is selected from a group consisting of rheumatoid arthritis (RA), rheumatoid spondylitis, systemic lupus erythematosus (SLE), multiple sclerosis (MS), autoimmune diabetes, Sjogren's syndrome or disease, psoriasis, inflammatory bowel disease, Graves' disease, diabetes mellitus type 1, celiac diseases, osteoarthritis and gouty arthritis, allergy, autoimmune uveitis, nephrotic syndrome, pemphigus vulgaris, Alzheimer's Disease, Behcet diseases (BD) and B cell malignancy.

In another aspect, provided is a kit for treating autoimmunity comprising therapeutically effective amounts of an anti-CD22 antibody and instructions stating
    (a) the anti-CD22 antibody is administered in at least two cycles;
    (b) each cycle comprises two or more doses; and
    (c) each dose is administered biweekly.

In another aspect, provided is a pre-loaded syringe comprising a therapeutically effective amount of an anti-CD22 antibody.

In another aspect, provided is a method for restoring immune control over autoimmunity in a subject in need thereof, comprising the step of administering to the subject a therapeutically effective amount of an antibody that disrupts Siglec-binding in cis. Restoring immune control over auto-immunity includes, but is not limited to, reducing an auto-immune response, treating an auto-immune disease, treating a disease selected from rheumatoid arthritis (RA), lymphoma, system lupus erythematosus (SLE), multiple sclerosis (MS), Sjogren's syndrome, psoriasis, inflammatory bowel disease, Graves' disease, diabetes mellitus type 1, celiac diseases, Alzheimer's Disease etc.

In another embodiment, the antibody disrupts Siglec-binding in cis by binding to one or more epitopes of the Siglec in such a way as to disrupt cis-ligation and sterically hinder cis-religation.

In another embodiment, the Siglec is human CD22 and the antibody is human anti-CD22 antibody.

In another embodiment, the antibody binds to the domain 2 of human CD22 at epitopes accessible for antibody binding that sterically disrupts CD22 cis-ligation; and has high enough affinity to human CD22 to prevent re-ligation of CD22 to its ligand in cis.

In another embodiment, the method further comprises the step of inducing human CD22 to internalize upon binding to the human anti-CD22 antibody.

In another embodiment, the anti-CD22 antibody is selected from the group consisting of SM03, SM06 and a combination thereof.

In another embodiment, the human anti-CD22 antibody binds to two discontinuous sequences of an epitope of CD22 antigen, and wherein the two discontinuous sequences comprise CLLNFSCYGYPIQ and VFTRSELKFSPQWSHHG-KIVTC, respectively. In another embodiment, the two discontinuous sequences are at least 95, 96, 97, 98 or 99% homologous to CLLNFSCYGYPIQ and VFTRSELKFSPQWSHHGKIVTC, respectively. In another embodiment, the two discontinuous sequences are CLLNFSCYGYPIQ and VFTRSELKFSPQWSHHG-KIVTC, respectively.

In another embodiment, the anti-CD22 antibody binds to the idiotope of an anti-idiotype antibody with a variable light chain region comprising the amino acid sequence of SEQ ID NO: 012, and a variable heavy chain region comprising the amino acid sequence of SEQ ID NO: 013. In another embodiment, the anti-CD22 antibody binds to the idiotope of an anti-idiotype antibody with a variable light chain region comprising the amino acid sequence being at least 95, 96, 97, 98 or 99% homologous to SEQ ID NO: 012, and a variable heavy chain region comprising the amino acid sequence being at least 95, 96, 97, 98 or 99% homologous to SEQ ID NO: 013.

In another embodiment, the autoimmunity is selected from the group consisting of rheumatoid arthritis (RA), rheumatoid spondylitis, systemic lupus erythematosus (SLE), multiple sclerosis (MS), autoimmune diabetes, Sjogren's syndrome or disease, psoriasis, inflammatory bowel disease, Graves' disease, diabetes mellitus type 1, celiac diseases, osteoarthritis and gouty arthritis, allergy, autoimmune uveitis, nephrotic syndrome, pemphigus vulgaris, Alzheimer's Disease, Behcet diseases (BD) and B cell malignancy.

In another aspect, provided is an engineered cell line expressing a fusion protein comprising non-internalizing, human CD22 domain 1 to 7, wherein the fusion protein has an amino acid sequence comprising at least 95% sequence identity to SEQ ID NO: 014. In another embodiment, the fusion protein has an amino acid sequence being at least 95, 96, 97, 98 or 99% homologous to SEQ ID NO: 014. In another embodiment, the fusion protein has an amino acid sequence of SEQ ID NO: 014.

In another aspect, provided is a method of screening for an antibody that is disruptive of Siglec binding in cis, comprising the steps of:
    a. providing an engineered cell line expressing a fusion protein comprising non-internalizing, human CD22 domain 1 to 7 and an endogenous ST6Gal I enzyme;
    b. comparing the binding of an exogenous probe containing multiple 2,6 Sia ligands to the engineered cell line in the presence and absence of an antibody of interest; and
    c. selecting the antibody that better restores the binding of the exogenous probe to the engineered cell line (as compared to the binding of the probe to the engineered cell line in the absence of the antibody).

In another embodiment, the engineered cell line is SP2/0.

In another embodiment, the exogenous probe is biotin-conjugated polyacrylamide substituted with α2-6-sialyllactose (6'PAA-B).

In another embodiment, the fusion protein comprises the extracellular domain of human CD22 fused to the transmembrane and cytoplasmic portion of glycophorin A.

In another embodiment, the fusion protein has an amino acid sequence comprising at least 95% sequence identity to SEQ ID NO: 014. In another embodiment, the fusion protein has an amino acid sequence being at least 95, 96, 97, 98 or 99% homologous to SEQ ID NO: 014. In another embodiment, the fusion protein has an amino acid sequence of SEQ ID NO: 014.

In another embodiment, the fusion protein comprises the extracellular domain of human CD22 fused to the glycophosphatidylinositol signal sequence isolated from decay accelerating factor (DAF) protein.

In another embodiment, the fusion protein has an amino acid sequence comprising at least 95% sequence identity to SEQ ID NO: 015. In another embodiment, the fusion protein has an amino acid sequence being at least 95, 96, 97, 98 or 99% homologous to SEQ ID NO: 015. In another embodiment, the fusion protein has an amino acid sequence of SEQ ID NO: 015.

In another aspect, provided is a method of making an antibody for restoring immune control over autoimmunity to a subject in need, comprising the steps of: (a) expressing a vector comprising a polynucleotide in a suitable host cell; wherein said polynucleotide encodes for a constant region comprising an IgG1 or IgG4 heavy chain; and a variable region specific to the regions of the Siglec that binding to the epitope is sufficient in disrupting cis-ligation and sterically hinder cis-religation; (b) recovering the antibody.

In another embodiment, the variable region is specific to human CD22.

In another embodiment, the variable region binds to a discontinuous conformational epitope comprising the sequence CLLNFSCYGYPIQ and VFTRSELKFSPQWSHHGKIVTC within the domain 2 of the human CD22 antigen. In another embodiment, the sequences are at least 95, 96, 97, 98 or 99% homologous to CLLNFSCYGYPIQ and VFTRSELKFSPQWSHHGKIVTC, respectively. In another embodiment, the sequences are CLLNFSCYGYPIQ and VFTRSELKFSPQWSHHGKIVTC, respectively.

In another embodiment, the variable region binds to the idiotope of an anti-idiotype antibody with a variable light chain region comprising the amino acid sequence of SEQ ID NO: 012, and a variable heavy chain region comprising the amino acid sequence of SEQ ID NO: 013. In another embodiment, the variable region binds to the idiotope of an anti-idiotype antibody with a variable light chain region comprising the amino acid sequence being at least 95, 96, 97, 98 or 99% homologous to SEQ ID NO: 012, and a variable heavy chain region comprising the amino acid sequence being at least 95, 96, 97, 98 or 99% homologous to SEQ ID NO: 013.

In another embodiment, the variable region comprises a variable light chain region which comprises an amino acid sequence of SEQ ID NO: 002, an amino acid sequence of SEQ ID NO: 003, and an amino acid sequence of SEQ ID NO: 004, and wherein the variable region comprises a variable heavy chain region which comprises an amino acid sequence of SEQ ID NO: 006, an amino acid sequence of SEQ ID NO: 007, and an amino acid sequence of SEQ ID NO: 008. In another embodiment, the variable region comprises a variable light chain region which comprises an amino acid sequence being at least 95, 96, 97, 98 or 99% homologous to SEQ ID NO: 002, an amino acid sequence being at least 95, 96, 97, 98 or 99% homologous to SEQ ID NO: 003, and an amino acid sequence being at least 95, 96, 97, 98 or 99% homologous to SEQ ID NO: 004, and wherein the variable region comprises a variable heavy chain region which comprises an amino acid sequence being at least 95, 96, 97, 98 or 99% homologous to SEQ ID NO: 006, an amino acid sequence being at least 95, 96, 97, 98 or 99% homologous to SEQ ID NO: 007, and an amino acid sequence being at least 95, 96, 97, 98 or 99% homologous to SEQ ID NO: 008.

In another aspect, provided is a method of modulating autoimmunity in an immune cell, comprising the step of contacting said immune cell with an effective amount of an antibody that disrupts Siglec-binding in cis.

In another embodiment, the antibody is an anti-CD22 antibody.

In another embodiment, the antibody is SM03, SM06, or combinations thereof.

In another aspect, provided is a method of releasing at least one sialic acid binding site of human CD22 from cis-binding configuration to trans-ligand formation in treating autoimmunity in a subject in need thereof, the method comprising the step of administering to the subject a therapeutically effective amount of an antibody, wherein the antibody binds to the domain 2 of human CD22 at epitopes accessible for antibody binding that sterically disrupts CD22 cis-ligation; and has high enough affinity to human CD22 to prevent re-ligation of CD22 to its ligand in cis.

In another embodiment, further comprising the step of inducing human CD22 to internalize upon binding to the antibody, wherein the antibody is a human anti-CD22 antibody.

In another embodiment, the human anti-CD22 antibody is selected from the group consisting of SM03, SM06 and a combination thereof.

In another embodiment, the human anti-CD22 antibody binds to two discontinuous sequences of an epitope of CD22 antigen, and wherein the two discontinuous sequences comprising CLLNFSCYGYPIQ and VFTRSELKFSPQWSHHGKIVTC respectively. In another embodiment, the sequences are at least 95, 96, 97, 98 or 99% homologous to CLLNFSCYGYPIQ and VFTRSELKFSPQWSHHGKIVTC, respectively. In another embodiment, the sequences are CLLNFSCYGYPIQ and VFTRSELKFSPQWSHHGKIVTC, respectively.

In another embodiment, the human anti-CD22 antibody binds to the idiotope of an anti-idiotype antibody with a variable light chain region comprising the amino acid sequence of SEQ ID NO: 012, and a variable heavy chain region comprising the amino acid sequence of SEQ ID NO: 013. In another embodiment, the human anti-CD22 antibody binds to the idiotope of an anti-idiotype antibody with a variable light chain region comprising the amino acid sequence being at least 95, 96, 97, 98 or 99% homologous to SEQ ID NO: 012, and a variable heavy chain region comprising the amino acid sequence being at least 95, 96, 97, 98 or 99% homologous to SEQ ID NO: 013.

In another embodiment, the autoimmunity is selected from the group consisting of rheumatoid arthritis (RA), rheumatoid spondylitis, systemic lupus erythematosus (SLE), multiple sclerosis (MS), autoimmune diabetes, Sjogren's syndrome or disease, psoriasis, inflammatory bowel disease, Graves' disease, diabetes mellitus type 1, celiac diseases, osteoarthritis and gouty arthritis, allergy, autoimmune uveitis, nephrotic syndrome, pemphigus vulgaris, Alzheimer's disease, Behcet diseases (BD) and B cell malignancy.

In another aspect, provided is a kit for treating autoimmunity comprising a pharmaceutical composition comprising a therapeutically effective amount of an antibody that disrupts Siglec-binding in cis and a plurality of instructions stating
(a) the antibody that disrupts Siglec-binding in cis is administered in at least two cycles;
(b) each cycle comprises two or more doses; and
(c) each dose is administered biweekly.

In another embodiment, the autoimmunity is selected from the group consisting of rheumatoid arthritis (RA), rheumatoid spondylitis, systemic lupus erythematosus (SLE), multiple sclerosis (MS), autoimmune diabetes, Sjogren's syndrome or disease, psoriasis, inflammatory bowel disease, Graves' disease, diabetes mellitus type 1, celiac diseases, osteoarthritis and gouty arthritis, allergy, autoimmune uveitis, nephrotic syndrome, pemphigus vulgaris, Alzheimer's disease, Behcet diseases (BD) and B cell malignancy.

In another aspect, provided is a pre-loaded syringe comprising a therapeutically effective amount of an antibody that disrupts Siglec-binding in cis.

In another aspect, provided is a method of treating autoimmunity while maintaining immunity against a cell or a pathogen that does not express 2,6 sialic acid ligand in a subject in need thereof, comprising administering to the subject an effective amount of an antibody that disrupts Siglec-binding in cis. In another embodiment, the cell does not express 2,6 sialic acid ligand. In another embodiment, the pathogen does not express 2,6 sialic acid ligand. In another embodiment, both the cell and the pathogen do not express 2,6 sialic acid ligand.

In another embodiment, the pathogen is bacteria.

In another embodiment, the cell is a virus-infected cell.

In another embodiment, the antibody disrupts cis-ligation in an immune cell and facilitates trans-ligation of the immune cell with an autologous cell.

In another aspect, provided is a use of an antibody in the manufacture of a medicament for treating autoimmunity in a subject in need thereof, therein the method comprises administering to the subject an effective amount of an antibody that disrupts Siglec-binding in cis.

BRIEF DESCRIPTION OF THE DRAWINGS

FIG. 1 is an overlay plot showing sensorgrams of 6 different concentrations of the anti-CD22 antibody (SM03) binding to the human CD22 antigen according to an example embodiment.

FIG. 2(A) is a dose response curves showing EC50 of SM03 and SM06 binding to CD22d2-4 according to an example embodiment. FIG. 2(B) is a dose response curves showing EC50 of SM03 and SM06 binding to LRID according to an example embodiment.

DETAILED DESCRIPTION OF THE INVENTION

Definitions

Figure 3A:
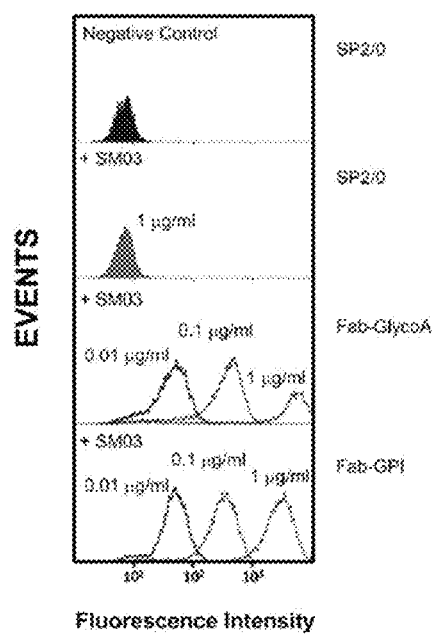
FIG. 3(A) shows flow cytometry studies of murine myeloma SP2/0 cells transfected with expression vector encoding the Fab fragment of the anti-idiotype antibody against SM03 (LRID Fab) fused either to the transmembrane portion of Glycophorin A (Fab-GlycoA) or the glycophosphatidylinosito (GPI) signal sequence from decay accelerating factor (DAF) protein demonstrated high level of surface expression of LRID Fab according to an example embodiment.

This invention pertains to methods of identifying anti-Siglecs antibodies, specifically anti-CD22 antibodies, that will bind to specific domains at specific epitopes, and with sufficiently high affinity to disrupt binding of the Siglec molecules to neighboring Siglecs or neighboring glycoprotein bearing the ligands in cis. The purpose of the disruptive binding is to free up Siglec-ligand binding site (e.g. CD22 binding to N-acetylneuraminic acid a(2-6) galactose (NeuAc-a(2-6)Gal)) so that the Siglec ligand binding sites (e.g. CD22) are made available for binding to their specific ligands on other immune cells in trans. Trans-binding of these regulatory Siglecs (e.g. CD22) results in increased association with the BCR and exertion of inhibitory functions on the immune system.

This invention further pertains to the employment of these cis-binding disrupting anti-Siglecs antibodies in restoring immune regulatory function of B cells by freeing up the Siglec binding site for binding to the glycans on other cells in trans, including methods of treating disorders in which the administration of an anti-Siglec (e.g. CD22) antibody is beneficial comprising the administration of isolated chimeric or framework-patched (humanized), or CDR-grafted, or human antibodies, or antigen-binding portions thereof, that bind to human Siglecs, specifically human CD22 with high affinity, and against specific domains and epitopes, in manners that disrupt formation of homomultimeric structure via cis-binding, making available disengaged ligand binding sites to interact with terminal sequence N-acetylneuraminic acid a(2-6) galactose (NeuAc-a(2-6)Gal) present on other hematopoietic cells or self-tissues in trans, such that the disorder is treated. Specifically, antibodies binding to human CD22 at specific discontinued conformational epitope resided in domain 2 containing the sequence $_{161}$CLLNFSCYGYPIQ$_{173}$ (SEQ ID NO: 016) and $_{198}$VFTRSELKFSPQWSHHGKIVTC$_{219}$ (SEQ ID NO: 017) and with a kd of 0.137 RU s$^{-1}$ or less, induces human CD22 internalization, and specific for an anti-idiotype antibody LRID against the anti-CD22 antibody with an EC$_{50}$ in the range of 79.9±27.6 ng/ml or less, and induce complement-mediated cell cytotoxicity (CMC) against a surrogate target cell line expressing surface LRID binding moiety with an EC$_{50}$ in the range of 0.1509±0.0207 mg/ml or less are sufficient to exert the above effects to restore the immune regulatory and/or inhibitory function of the Siglecs such that the disorder is treated. Various aspects of the invention relate to the identification, evaluation and testing of the appropriate antibodies and the use of such antibodies and antibody fragments for the treatment of the disorder, and pharmaceutical compositions thereof.

This invention also pertains to methods of treating disorders in which the administration of an anti-CD22 antibody is beneficial comprising the administration of isolated chimeric or framework-patched (humanized) antibodies, or antigen-binding portions thereof, that bind to human CD22 with high affinity, against a specific discontinued conformational epitope resided in domain 2, and specific for an anti-idiotype antibody LRID against the anti-CD22 antibody with an EC$_{50}$ in the range of 79.9±27.6 ng/ml or less, and induce complement-mediated cell cytotoxicity (CMC) against a surrogate target cell line expressing surface LRID binding moiety with an EC$_{50}$ in the range of 0.1509±0.0207 µg/ml or less such that the disorder is treated. Various aspects of the invention relate to treatment with antibodies and antibody fragments, and pharmaceutical compositions thereof. In order that the present invention may be more readily understood, certain terms are first defined.

As used herein and in the claims, "comprising" means including the following elements but not excluding others.

The term "auto-immune disease or disorder" refers to a disease or disorder characterized by an abnormal immune response to normal body cells, tissue, organ, or a whole body part. For instance, the immune system may produce antibodies that attack normal body tissue. In some embodiments, the auto-immune disease or disorder is caused by dysfunctional immune control. An auto-immune disease or disorder includes, but is not limited to, rheumatoid arthritis (RA), systemic lupus erythematosus (SLE), multiple sclerosis (MS), Sjogren's syndrome, psoriasis, inflammatory bowel disease, Graves' disease, diabetes mellitus type 1, celiac diseases, rheumatoid spondylitis, osteoarthritis and gouty arthritis, allergy, autoimmune uveitis, nephrotic syndrome, pemphigus vulgaris, Alzheimer's disease, Behcet diseases (BD), and B cell malignancy, etc.

The term "rheumatoid arthritis" or "RA" refers to a systemic inflammatory disease arising from uncontrolled autoimmune reaction leading to prolonged inflammatory response. Such inflammatory response primarily targets joints leading to hypertrophia and hyperplasia of the synovial tissue, destruction of articular structures and subchondral bone, malposition, ankylosis and, eventually to the restriction in joint function. Other pathological changes in various tissues, such as skin, blood vessels, heart, lung, muscles and several internal organs may also be possible. RA patients suffer from pain and reduction in quality of life, and are associated with increased morbidity, considerable co-morbidity and disability. Although the introduction of anti-TNFα and anti-IL1 combination therapy with traditional disease-modifying anti-rheumatic drugs (DMARDs) have significantly improved RA treatments, there remains substantial number of patients that either fail to respond to the treatment options or eventually become refractory to the treatment.

The term "CD22" refers to a B cell restricted antigen that belongs to the immunoglobulin (Ig) superfamily and is a type I transmembrane sialoglycoprotein also known as sialic-acid-binding immunoglobulin-type lectins (Siglecs) with a molecular size of 135-kD. In resting B cells, CD22 is a prominent cis ligand for itself, forming CD22 homo-oligomers.

The term "Siglecs", as used herein, refers to a sialic-acid-binding immunoglobulin-type lectins such as human CD22 and Siglec-10. Siglec-10 and CD22 are the only Siglecs expressed on B-cell surfaces. These molecules are constitutively expressed on B cells and act as inhibitory co-receptors of the B cell antigen receptor (BCR) in the maintenance of B-cell tolerance and prevention of autoimmune diseases.

The term "internalization", as used herein, refers to either the constitutive clathrin-mediated endocytosis of Siglecs such as CD22 or increased rate of endocytosis of Siglecs (e.g. CD22) by binding to an anti-Siglec antibody (such as SM03 and/or SM06); internalization of this type is a recycling process where the Siglec (with or without binding to an anti-Siglec antibody) is endocytosed into the endosomal compartments, and the low pH environment frees up Siglec binding to its specific ligands (e.g. CD22 binding in cis), and the free Siglec returns back to the cell surface for possible cis- or trans-ligand binding. When the Siglec is induced to internalize when bound to a disruptive anti-Siglec antibody (e.g. SM03 and/or SM06 against CD22), the antibody is recycled to the cell surface along with the Siglec (e.g. CD22), sterically hindering further cis-ligand binding to other surface CD22.

The term "ligand binding", as used herein, refers to binding of Siglecs (e.g. CD22) to their specific ligands on the glycans of endogenous glycoproteins that are distributed either on the same cell (cis), or on a different cell (trans); different Siglecs will bind to a different ligand structure. For example, human CD22 is specific to the structure: N-acetyl-neuraminic acid (2-6) galactose (NeuAc-(2-6)Gal) expressed on hematopoietic and liver cells.

The term "cis-binding", as used herein, refers to binding of Siglecs (e.g. CD22) to their specific ligands on the glycans of endogenous glycoproteins that are distributed on the same cell (e.g. B cell), usually forming homo-oligomers or homo-multimers. Cis-binding of Siglecs is between neighboring molecules where the glycan binding site of a Siglec molecule is ligated to the glycan molecule of another Siglec or glycoprotein on the same cell. Cis-binding of Siglecs such as CD22 is demonstrated to exert a masking effect on the molecule, preventing the Siglec forming cell to cell ligation (trans-binding) that is required for the elicitation of inhibitory immunological signals for the induction of tolerance.

The term "trans-binding", as used herein, refers to binding of Siglecs (e.g. CD22) located in one cell to their specific ligands on the glycans of endogenous glycoprotein on the other cell, resulting in the physical association of the Siglec (e.g. CD22) with the BCR to exert a maximal inhibitory response.

The term "disruptive binding", as used herein, refers to the binding of an anti-Siglec antibody on to the Siglec (e.g. CD22) molecule at a domain close to the ligand binding site of the Siglec and at an epitope that will efficiently tear apart cis-binding onto neighboring molecule due to steric hindrance; the high affinity of the anti-Siglec antibody (e.g. SM03 and/or SM06 with affinity of 1.22 nM) will favorably compete with cis-ligand binding (affinity ~30 mM) and will help maintain the binding throughout the internalization process, maintaining the steric hindrance that will prevent re-ligation of the Siglec in cis.

The term "dosing", as used herein, refers to the administration of a substance (e.g. an anti-CD22 antibody or antibody fragments) to achieve a therapeutic objective (e.g., the treatment of an immunological disorder or disease associated with abnormal B cell activities).

The terms "biweekly dosing regimen", "biweekly dosing", and "biweekly administration", as used herein, refer to the time course of administering a substance (e.g. an anti-CD22 antibody or antibody fragments) to a subject to achieve a therapeutic objective (e.g., the treatment of an immunological disorder or diseases associated with abnormal B cell activities). The biweekly dosing regimen is not intended to include a weekly dosing regimen. Preferably, the substance is administered every 9-19 days, more preferably, every 11-17 days, even more preferably, every 13-15 days, and most preferably, every 14 days.

The term "dosing cycle", as used herein, refer to the period in which a number of biweekly dosing regimen, biweekly dosing, or biweekly administration with a substance (e.g. an anti-CD22 antibody or antibody fragments) to a subject to achieve a therapeutic objective (e.g., the treatment of an immunological disorder or diseases associated with abnormal B cell activities). Preferably, the substance is administered under biweekly dosing regimen, biweekly dosing or biweekly administration either two times or three times within a treatment cycle; more preferably, the substance is administered under biweekly dosing regimen, biweekly dosing or biweekly administration within a period of 9-15 weeks, even more preferably, within a period of 10-14 weeks, even more preferably, within a period of 11-13 weeks, and most preferably, within a period of 12 weeks;

The term "treatment cycle", as used herein, refer to the number of dosing cycle adopted for the administration of a substance (e.g. an anti-CD22 antibody or antibody fragment) to a subject to achieve a therapeutic objective (e.g., the treatment of an immunological disorder or diseases associated with abnormal B cell activities). Preferably, the substance is administered 1-5 dosing cycles, more preferably, 1-4 dosing cycles, even more preferably, 1-3 dosing cycles, and most preferably, 2 dosing cycle in a treatment cycle.

The term "maintenance dosing", as used herein, refer to the dosing regimen for maintaining a therapeutic response after a treatment cycle in which a subject is administered with a substance (e.g., an anti-CD22 antibody or antibody fragment) to achieve a therapeutic objective (e.g., the treatment of an immunological disorder or diseases associated with abnormal B cell activities). Preferably, the substance is administered every 2-10 weeks, more preferably, every 3-8 weeks, even more preferably, every 4-7 week, and most preferably every 6 weeks after the subject has completed the treatment cycle.

The term "combination therapy", as used herein, refers to the administration of two or more therapeutic substances, e.g., an anti-CD22 antibody and the drug methotrexate. The methotrexate may be administered concomitant with, prior to, or following the administration of an anti-CD22 antibody.

The term "human CD22" or "hCD22" as used herein, is intended to refer to a human B cell-restricted surface antigen CD22 that exists as a type I transmembrane sialoglycoprotein with a molecular size of 135-kD. CD22 is another B cell restricted antigen; it belongs to the immunoglobulin (Ig) superfamily and is a type I transmembrane sialoglycoprotein with a molecular size of 135-kD. The term human CD22 is intended to include recombinant human CD22 (rhCD22), either in its full molecular form containing the extracellular, intracellular and transmembrane regions, or expressed as a soluble form containing only the extracellular regions, or portions of the extracellular portions containing the binding epitopes of the anti-CD22 antibodies, which can be prepared by standard recombinant expression methods or purchased commercially (e.g., Abcam, Catalog No. Ab50033, Cambridge, MA; Creative Biomart, Catalog No. CD22-3946H, Shirely, NY; Thermo Fisher Scientific, Catalog No. 11958H08H5, Waltham, MA)

The term "binding epitope of CD22" as used herein, refers to the specific region, sequence, or sequences of the human CD22 onto which the anti-CD22 antibodies bind to or interact with. The binding epitope of CD22 can be a linear sequence within a single domain, preferably, spanning multiple domains; more preferably, the binding epitope is composed of multiple discontinuous sequences, even more preferably, the binding epitope is composed of multiple discontinuous sequences in a specific conformational structure.

The term "discontinuous conformational epitope" as used herein, refers to the portion of the naturally folded structure of an antigen that interacts specifically with the antigen binding site (ABS) of the targeting antibody, and the portion of the naturally folded structure is constituted by at least two separate, discontinuous sequences forming a specific conformation.

The term "anti-idiotype antibody" as used herein, refers to antibodies or antibody fragments thereof that are specific for the anti-CD22 antibodies, preferably, the anti-idiotype antibody is specific for the ABS of the anti-CD22 antibodies of the Ab1y type (recognizing idiotopes close to the paratope of the anti-CD22 antibodies without mimicking the internal image of the binding epitope of CD22), more preferably, the anti-idiotype antibody is specific for the ABS of the anti-CD22 antibodies of the Ab2β type (mimicking the internal image of the binding epitope of CD22).

The term "surrogate target cell" as used herein; refers to cell lines engineered to recombinantly express on their surface with binding moieties that can interact with the anti-CD22 antibodies for the induction of complement dependent cytotoxicity (CMC) and/or antibody dependent cell cytotoxicity (ADCC) activities. The binding moieties can be portions of human CD22, preferably, sequences containing the binding epitope of CD22, more preferably, anti-idiotype antibody against the anti-CD22 antibodies, even more preferably, Fab fragments of the anti-idiotype antibody against the anti-CD22 antibodies (see e.g. Chinese Pat. No. ZL201210286457.4; U.S. Pat. No. 9,371,396 B2, which are incorporated by reference herein).

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3, and there is a short flexible hinge region connecting the CH1 and CH2 domains. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or simply "antibody portion"), as used herein, refers to one or more fragments of an antibody that retain the ability to specifically bind to an antigen (e.g., human CD22). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and SH1 domains without the hinge region; (ii) a Fab' fragment, a monovalent fragment consisting of the VL, VH, CL and CH1 domains attached with a hinge region; (iii) a F(ab')2 fragment, a bivalent fragment comprising two Fab fragments linked by a disulfide bridge at the hinge region; (iv) a Fd fragment consisting of the VH and CH1 domains; (v) a Fv fragment consisting of the VL and VH domains of a single arm of an antibody, (v) a dAb fragment (Ward et al., (1989) Nature 341:544-546), which consists of a VH domain; and (vii) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (know as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al (1993) *Proc. Natl. Acad. Sci.* USA 90:6444-6448; Poljak, R. J., et al. (1994) *Structure* 2:1121-1123).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrmeric scFv molecule (Kipriyanov, S. M., et al (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab, Fab' and F(ab')2 fragments, can be prepared from whole antibodies using conventional techniques, such as papain or pepsin digestion, respectively, of whole antibodies. Moreover, antibodies, antibody portions and immunoadhession molecules can be obtained using standard recombinant DNA techniques, as described herein.

The term "chimeric antibody", as used herein, is intended to include antibodies having variable and constant regions derived from murine or other non-human origin immunoglobulin sequences, whereas the constant CL and CH1-hinge-CH2-CH3 regions for both the light and heavy chains are derived from human immunoglobulin. The term "framework-patched (humanized) antibody", as used herein, is intended to include antibodies having the CDRs that are grafted onto segments of human frameworks, whereas these segments of frameworks (e.g., FR1, FR2, FR3 and FR4 of HCVH and LCVL) can be derived from the same human immunoglobulin sequence, or freely assorted from different human immunoglobulin sequences (framework-patching). CDRs embedded into these human frameworks are genetically fused to the constant CL and CH1-hing-CH2-CH3 regions of human immunoglobulin.

The term "recombinant human antibody", as used herein, is intended to include all chimeric and framework-patched (humanized) antibodies that are prepared, expressed, or created or isolated by recombinant means, such as antibodies expressed using a recombinant expression vector transfected into a host cell (described further in Section II, below), antibodies isolated from a recombinant, combinatorial human antibody library (described further in Section III, below), antibodies isolated from an animal (e.g., a mouse) that is transgenic for human immunoglobulin genes (see e.g., Taylor, L. D., et al (1992) *Nucl. Acid Res.* 20:6287-6295) or antibodies prepared, expressed, created or isolated by any other means that involves splicing of human immunoglobulin gene sequences to other DNA sequences.

An "isolated antibody", as used herein, is intended to refer to an antibody that is substantially free of other antibodies having different antigenic specificities (e.g., an isolated antibody that specifically binds human CD22 is substantially free of antibodies that specifically bind antigens other than human CD22). An isolated antibody that specifically binds human CD22 may, however, have cross-reactivity to other antigens, such as CD22 from other species. Moreover, an isolated antibody may be substantially free of other cellular material and/or chemicals.

A "biologically active antibody" is an antibody that exerts biological responses manifested either as peripheral B cell population suppression or reduction in vivo, or disrupt ligand binding of the target molecule in cis, or elicit tumor regression in human, or modulate immune responses in diseased conditions such as immunological disorder, or induce apoptosis in human lymphoma cell lines, or induce internalization in human lymphoma cell lines, or elicit antibody-dependent cellular cytotoxicity (ADCC) against human lymphoma cell lines, or elicit complement mediated cell cytotoxicity (CMC) or antibody dependent cell cytotoxicity (ADCC) against a surrogate target cell expressing surface binding moieties against the biologically active antibody. These indicators of biological activities can be assessed by one or more of several standard in vitro or in vivo known in the art. Preferably, the biologically active antibody specific for human CD22 is assessed by elicitation of CMC or ADCC against the surrogate target cells in vitro.

The term "SM03" refers to a chimeric antibody against human CD22 (hCD22) (for example, such as the antibody described in Leung et al. Chinese Pat. No. ZL03123054.7, incorporated in its entirety herein by reference).

The term "SM06" refers to a framework-patched or humanized version of chimeric antibody SM03 reengineered to reduce its potential immunogenicity and exhibiting affinity and specificity against human CD22 comparable to that of SM03 (Liang et al. (2006) Chinese *J New Drug* 15(21): 1832-1836). The construction of the framework-patched SM06 and its uses are described in Chinese Patent No. ZL 011 44894.6, U.S. Pat. Nos. 7,321,026 B2 & 7,338,659 B2, incorporated in its entirety herein by reference.

The term "surface plasmon resonance", as used herein refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, NJ). For further descriptions, see Johnsson, U., et al. (1993) Ann. Biol. Clin. 51:19-26; Johnsson, B., et al. (1995) *J. Mol. Recognit.* 8:125-131; and Johnnson, B., et al. (1991) *Anal. Biochem.* 198:268-277.

The term "Kd", as used herein, is intended to refer to the equilibrium dissociation constant of a particular antibody-antigen interaction. It can be defined as the ratio of the products of concentrations of free antibody and free antigen over the concentrations of antibody-antigen complex, i.e. [Antigen]×[Antibody]/[antigen-antibody].

The term "kd", as used herein, is intended to refer to the dissociation rate constant of a particular antibody-antigen interaction, used to describe the stability of the antibody-antigen complex, i.e., the fraction of complexes that dissociates per second.

The term "Ka", as used herein, is intended to refer to the equilibrium association constant of a particular antibody-antigen interaction. It is the reciprocal of the equilibrium dissociation constant, i.e. =1/Kd.

The term "ka", as used herein, is intended to refer to the association rate constant, which describes the rate of antibody-antigen complex formation, i.e. the number of complexes formed per second in a one molar solution of antibody and antigen.

The term "$EC_{50}$", as used herein, is intended to refer to the concentration of an antibody that gives half-maximal response.

The term "$IC_{50}$", as used herein, is intended to refer to the concentration of an antibody where the response or binding is reduced by half.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nuclei acids encoding antibodies or antibody portions (e.g., VH, VL, CDR3) that bind human CD22, is intended to refer to nucleic acid molecule in which the nucleotide sequences encoding the antibody or antibody portion are free of other nucleotide sequences encoding antibodies or antibody portions that bind antigens other than human CD22, which other sequences may naturally flank the nuclei acid in human genomic DNA. Thus, for example, an isolated nucleic acid of the invention encoding a VH region of an anti-CD22 antibody contains no other sequences encoding other VH regions that bind antigens other than human CD22.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors' (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer no only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Various aspects of the invention are described in further detail in the following subsections.

I. Antibodies that Disrupt Binding of Siglecs in Cis

This invention provides an approach of using antibodies specific for Siglecs to disrupt Siglecs' binding to their ligands in cis, freeing up the ligand binding site of Siglecs for ligation to ligands on other immune cells in trans, so that the Siglecs can exert their inhibitory function upon physical association with the B-cell receptor (BCR) and restore immune tolerance against the antigen of the BCR. Specifically, one of the Siglecs used as an example in this invention is human CD22. This invention further provides methods of using cell lines that express non-internalizing CD22 extracellular domain for the evaluation of anti-CD22 antibodies that are disruptive of CD22 binding in cis without affecting its binding in trans. The method includes the use of these cell lines for binding to a synthetic ligand FITC or biotin-conjugated polyacrylamide substituted with a2-6-sialyllactose (6'PAA-FITC and 6'PAA-B) (GlycoTech, Rockville, MD) in trans in the absence and presence of the anti-CD22 antibodies. The extent of trans-binding enhancement by the anti-CD22 antibodies is evaluated by comparing the fluorescence intensity of the probe before and after the binding by the anti-CD22 antibodies in flow cytometry analyses. Similar approaches can be used for the evaluation of other antibodies of other Siglecs.

II. Chimeric and Framework-Patched (Humanized) Antibodies that Bind Human CD22

This invention provides methods of treating disorders in which the administration of an anti-Siglec antibody is beneficial. In some embodiments, that anti-Siglec antibody is an anti-CD22 antibody. These methods include administration of isolated human antibodies, or antigen-binding portions thereof, that bind to a specific conformational epitope that efficiently disrupt CD22 binding in cis, either with CD22, or with neighboring molecular expressing the CD22 ligand. In some embodiments, these methods include a biweekly, intravenous administration of isolated human antibodies, or antigen-binding portions thereof. Specifically, the anti-CD22 antibody binds to the domain 2 of human CD22 with high affinity, and the anti-CD22 antibody can be a chimeric, framework-patched, CDR-grafted and/or fully human antibody. In some embodiments, the chimeric, framework-patched, CDR-grafted, and/or fully human antibodies in addition to binding to human CD22, binds to an anti-idiotype antibody against the antigen binding site (ABS) of SM03 and SM06 with an $EC_{50}$ in the range of 79.9±27.6 ng/ml or less (see Leung, S. O., et al. (2015) *MAbs*7(1):66-76; Zhao, Q., et al. (2014) *PLOS ONE* 9(5): e96697, and as described in U.S. Pat. No. 9,371,396B2, Chinese Pat. No. ZL201210286457.4, which are incorporated by reference herein) and is able to induce CMC activity against a recombinant engineered surrogate cell line expression surface bound anti-idiotype binding fragments (Fab fusion) (see e.g., Leung, S. O., et al. (2015) *MAbs*7(1):66-76, and as described in U.S. Pat. No. 9,371,396B2, Chinese Pat. No. ZL201210286457.4, which are incorporated by reference herein). The most preferred recombinant anti-CD22 antibody is referred to herein as SM03 (the amino acid sequence of the SM03 VL region is shown in SEQ ID NO: 001; the amino acid sequence of the SM03 VH region is shown in SEQ ID NO: 005) and SM06 (the amino acid sequence of the SM06 VL region is shown in SEQ ID NO: 009; the amino acid sequence of the SM06 VH region is shown in SEQ ID NO: 010). The properties of SM03 have been described in Yang et al. (2006) (*Chinese J New Drug* 15(3):186-192) and Chinese Pat. No. ZL 031 23054.7, which are incorporated by reference herein; and the properties of SM06 have been described in Leung et al. (2006) (*Chinese J New Drug* 15(21):1832-1836, and U.S. Pat. Nos. 7,321,026 B2 and 7,338,659 B2, which are incorporated by reference herein).

In one aspect, the invention pertains to treating disorders in which the administration of an anti-CD22 antibody is beneficial. These treatments include the biweekly, intravenous administration of SM03 or SM06 antibodies and antibody portions, SM03- or SM06-related antibodies and antibody portions, and other chimeric, humanized and human antibodies and antibody portions with equivalent properties to SM03, such as high affinity binding to exogenous CD22 with relatively low dissociation kinetics against a specific epitope within the domain 2 of the antigen with high effector Fc function, as revealed by the anti-CD22 antibody's ability to induce CMC and/or ADCC against a surrogate target cell with surface expression of an anti-idiotype antibody for SM03.

In some embodiments, the equivalent properties to SM03 further comprise the ability to effectively disrupt CD22 homo-multimeric binding or CD22 binding to neighboring glycoproteins in cis, ability to induce internalization of the antibody-CD22 complexes.

In one embodiment, the invention provides treatment with an isolated chimeric and/or framework-patched (humanized) antibody, or an antigen-binding portion thereof, that dissociates from exogenous human CD22 with a Kd of $1.22 \times 10^{-9}$ M or less, a kd of 0.0137 RU s$^{-1}$ or less, Ka in the range of $0.82 \times 10^9$ M$^{-1}$ or more, and ka in the range of $1.13 \times 10^!$ RU S$^{-1}$ or higher both determined by surface plasmon resonance, or competes with radiolabelled I$^{125}$-SM03 binding to native CD22 on Ramos cell, a human Burkitt's lymphoma cell line, with IC$_{50}$ in the range of $1.02 \pm 0.007$ μg/ml or less, and/or binds to an antigen-binding site specific anti-idiotype antibody (see U.S. Pat. No. 9,371,396 B2, Chinese Patent No. ZL201210286457.4, which are incorporated by reference herein) with an EC$_{50}$ in the range of $79.9 \pm 27.6$ ng/ml or less, and induces CMC activities against a surrogate cell line expressing surface LRID binding moieties with an EC$_{50}$ in the range of $150.9 \pm 20.7$ ng/ml or less (see U.S. Pat. No. 9,371,396 B2, Chinese Patent No. ZL201210286457.4, which are incorporated by reference herein). More preferably, the isolated chimeric and/or framework-patched (humanized) antibody, or antigen-binding portion thereof, dissociates from exogenous human CD22 with a kd of 0.0685 RU s-1 or less, or even more preferably, with a kd of 0.0137 RU s-1 or less. More preferably, the isolated chimeric and/or framework-patched (humanized) antibody, or antigen-binding portion thereof, competes with radiolabeled I$^{125}$-labeled SM03 for binding to human CD22 on Ramos cell, a human Burkitt's lymphoma cell line, in a competitive binding assay with an EC$_{50}$ of 5.01 μg/ml or less, even more preferably with an EC$_{50}$ of 1.02 μg/ml or less. More preferably, the isolated chimeric and/or framework-patched (humanized) antibody, or antigen-binding portion thereof, binds specifically to an anti-idiotypic antibody against the antigen-binding-site (ABS) of SM03 and SM06, with an EC$_{50}$ of 0.3995 μg/ml or less, or even more preferably, with an EC$_{50}$ of 0.0799 μg/ml. More preferably, the isolated chimeric and/or framework-patched (humanized) antibody, or antigen-binding portion thereof, induces CMC killing against a surrogate target cell engineered to express on its surface binding portion of the anti-idiotype antibody, with an EC$_{50}$ of 0.7545 μg/ml or less, or even more preferably, with an EC$_{50}$ of 0.1509 μg/ml or less. In a preferred embodiment, the antibody is an isolated chimeric and/or framework-patched (humanized) recombinant antibody, or an antigen-binding portion thereof.

An antibody targeting the same antigen but at a different epitope and with different affinity will have different biological responses [e.g. type I anti-CD20 antibodies such as Rituximab and Ofatumumab could induce ADCC, strong CMC and weak non-apoptotic programmed cell death, while type 11 anti-CD20 antibodies such as Obinutuzumab and Tositumomab could induce ADCC, weak CMC and strong non-apoptotic programmed cell death] (Bears et al. (2010) *Semin Hematol* 47:107-114).

Accordingly, in another aspect, the invention provides methods of treating disorders in which the administration of an anti-CD22 antibody is beneficial by intravenous administration of anti-CD22. Some embodiments provides methods of treating disorders in which the administration of an anti-CD22 antibody is beneficial by intravenous administration of anti-CD22 antibodies that disrupt the cis-ligand binding of these CD22 on B cells, for example, an antibody that targets domain 2 of the human CD22 antigen, specifically at the discontinuous conformational epitope encompassing the sequence $_{161}$CLLNFSCYGYPIQ$_{173}$ (SEQ ID NO: 016) and $_{198}$VFTRSELKFSPQWSHHGKIVTC$_{219}$ (SEQ ID NO: 017), and with affinity (Ka) in the range of $0.82 \times 10^9$ M$^{-1}$ and simultaneously binds to the anti-idiotype antibody against the anti-CD22 antibody with an EC$_{50}$ in the range of $79.9 \pm 27.6$ ng/ml.

Siglecs such as human CD22 functions as a negative regulator which mediates inhibition of B-cell antigen receptor-induced signaling. These Siglecs, specifically CD22, recognize endogenous sialic acids expressed on glycoproteins of various cellular surfaces. They bind to a2,6-linked sialic acids (2,6Sia), in cis on the same cell or in trans on other cells, with their N-terminal immunoglobulin-like domain. Only cells, mostly hematopoietic cells such as T cells, B cells, antigen presenting cells (APC) and liver cells, that constitutively express the ST6Gal I (Gal1b1-4GlcNAc-specific a2-6-sailytransferase) enzyme, can produce 2,6Sia ligands on the cell surface. In resting B cells, CD22 is a prominent cis ligand for itself, forming CD22 homo-oligomers. The moderately low affinity of CD22 to its 2,6Sia ligand, but high sialyation on cell surface proteins, causes a masking effect by self-ligands and allows limited availability to trans ligands.

The trans-ligand binding is a mechanistical recognition of the sialyated structure on target cells, leading to the ligation of CD22 and Siglec-10 to the BCR and ultimate suppression of an immune response (e.g., B cell inhibition) to this antigen.

The disruption of CD22 homo-oligomers, either by deletion of the ST6Gal I gene, or with a mutated CD22 ligand-binding domain (CD22 Arg130Glu) in mice, results in increased CD22-BCR association and enhanced Ca$^{2+}$ inhibition upon anti-IgM stimulation. This effect indicates a crucial cis-ligand binding function of CD22 in regulating the B-cell activation status. Disruption of cis-ligand binding for CD22 homo-oligomers is achieved by the antibodies described in the present invention, freeing up unoccupied CD22 ligand binding sites for ligand binding in trans, which induces B-cell signal inhibition when target cells co-express antigen and sialic acids.

Another embodiment provides a disruptive antibody for Siglecs having one or more of the following properties:
1. Binds to a domain close to the ligand binding site without interfering its ligand binding property when cis-binding is disrupted;
2. Binds to an epitope that will sterically hinder re-engagement of cis-ligand binding when disrupted;
3. Binds to the particular epitope with high affinity first to compete with cis-ligand binding (estimated to have a kd of ~0.1-0.3 mM), then to remain bound to the epitope and sterically hinder re-association of CD22 homo-oligomers via cis-binding.

In an example embodiment, the Siglec is CD22.

Another embodiment provides an antibody against Siglecs that can induce internalization. In some embodiments, the Siglec-specific antibody internalizes through the clathrin-coated pit in a recycling manner; that is, antibody bound to CD22 remains bound during the process, while the glycan ligand is released at the low pH of endosomes.

CD22 is a recycling receptor that can shuttle cargo between the cell surface and endosomal compartments of B cells. The resurfaced CD22 freed of cis-ligation can bind to the glycan ligand on other cells in trans, making B cell activation via BCR engagement with self-antigen more likely to be attenuated or modulated by the trans-ligated CD22. Antibodies binding to a different domain at different epitopes with certain affinity that do not effectively disrupt cis-ligand binding might have some but insufficient clinical effects and are therefore less desirable, as the extent of trans-binding may not be sufficient to elicit the intended immunomodulatory activity to result in a satisfactory clinical outcome.

Antibody heavy and light chain CDR3 domains play an important role in the binding specificity/affinity of an antibody for an antigen, especially when the antibody has to compete with Siglec (e.g. CD22) homo-oligomeric binding in cis, and continuously exert steric hindrance in preventing the re-engagement of the freed Siglec (e.g. CD22) in cis. Accordingly, in another aspect, the invention pertains to methods of treating disorders in which the administration of an anti-CD22 antibody is beneficial by intravenous administration of anti-CD22 antibodies that have the appropriate association/dissociation kinetics with human CD22 and that have light and heavy chain CDR3 domains that structurally are identical to or related to those of SM03. Accordingly a consensus motif for the SM03 VL CDR3 comprising the amino acid sequence: Q-Q-G-N-T-L-P-W-T (SEQ ID NO:004) can be modified by substituting one or more of the amino acid(s) to adjust the antibody affinity without changing its binding specificity, or alternatively be replaced by the VL CDR3 of an irrelevant human antibody that exhibits sufficient similarities to the SM03 VL CDR3 using criteria as described in Chinese Pat. No. ZL200880024788.2, which is incorporated herewith by reference. Similarly, a consensus motif for the SM03 VH CDR3 comprising the amino acid sequence: H-S-G-Y-G-S-S-Y-G-V-L-F-A-Y (SEQ ID NO: 004) can be modified by substituting one or more of the amino acid(s) to adjust the antibody affinity without changing its binding specificity, or alternatively be replaced by the VH CDR3 of an irrelevant human antibody that exhibits sufficient similarities to the SM03 VH CDR3 using criteria as described in Chinese Pat. No. ZL200880024788.2, which is incorporated herewith by reference. The skilled artisan will appreciate that, substitution of other amino acids within the CDR3 domains may be possible while still retaining the epitope specificity of the antibody, in particular substitutions with conservative amino acids. Similarly, it is possible to replace the CDR3 with the CDR3 from a human or primate antibody that (1) is identical in the number of residues and exhibits 50% or higher sequence homology to the SM03 CDR3, (2) contains at least one, preferably more, aromatic residue(s) that is (are) identical or conservatively similar to the residue(s) at corresponding position(s) in the SM03 CDR3, (3) contains at least one, preferably more, charged residue(s) that is (are) identical or conservatively similar to the residue(s) at corresponding position(s) in the SM03 CDR3, (4) contains at least one, preferably more, amino acid residue(s) that is/are identical or conservatively similar to the residue(s) at corresponding position(s) in the SM03 CDR3 at positions that are known to be important for maintaining the binding site structure/contacts of the anti-CD22 antibody as determined by crystal structure and/or computer database analysis (see Chinese Pat. No. ZL200880024788.2, which is incorporated herewith by reference). A "conservative amino acid substitution" as used herein, is one in which one amino acid residue is replaced with another amino acid residue having a similar side chain. Amino acid or residue that is "conservatively similar" as used herein refers to non-identical amino acid residue having similar side chains. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Preferably, no more than one to five conservative amino acid substitutions are made with the SM03 VL and/or VH CDR3 domains, or VL and/or VH CDR3 from irrelevant primate or human antibodies containing no more than one to five conservatively similar residues are used to replace the VL and/or VH CDR3 of SM03 or SM06. More preferably, no more than one to three conservative amino acid substitutions are made within the SM03 VL and/or VH CDR3 domains, or VL and/or VH CDR3 from irrelevant primate or human antibodies containing no more than one to three conservatively similar residues is used to replace the VL and/or VH CDR3 of SM03 or SM06.

Accordingly, in another embodiment, the invention provides methods of treating disorders in which the administration of an anti-CD22 antibody is beneficial by the biweekly, intravenous administration of an isolated chimeric and/or framework-patched (humanized) antibody, or antigen-binding portion thereof. The antibody or antigen-binding portion thereof preferably contains one or more of the following characteristics:

a) Binds to the domain 2 of human CD22, specifically, interacts with at least one of the two domain 2 sequence $_{161}$CLLNFSCYGYPIQ$_{173}$ (SEQ ID NO: 016) or $_{198}$VFTRSELKFSPQWSHHGKIVTC$_{219}$ (SEQ ID NO: 017), or preferably both of the discontinuous sequences $_{161}$CLLNFSCYGYPIQ$_{173}$ (SEQ ID NO: 016) & $_{198}$VFTRSELKFSPQWSHHGKIVTC$_{219}$ (SEQ ID NO: 017) in a conformational manner;

b) Dissociates from human CD22 with a kd of 0.0137 RU s$^{-1}$ or less, determined by surface plasmon resonance;

c) Induces internalization upon binding to surface human CD22;

d) Competes with radiolabelled I$^{125}$-SM03 binding to native CD22 on Ramos cell, a human Burkitt's lymphoma cell line, with IC$_{50}$ in the range of 1.02±0.007 µg/ml;

e) Binds to an anti-idiotype antibody specific for the anti-CD22 antibody (see U.S. Pat. No. 9,371,396 B2) with an EC$_{50}$ in the range of 79.9±2.76 ng/ml;

f) Induces CMC activities against a surrogate target cell expressing surface binding moieties of the anti-idiotype antibody specific for the anti-CD22 antibody with an EC$_{50}$ in the range of 0.1509±20.7 µg/ml (see U.S. Pat. No. 9,371,396 B2, incorporated herewith by reference);

g) Has a light chain CDR3 domain comprising the amino acid sequence of SEQ ID NO: 004, or modified from SEQ ID NO: 004;

h) Has a heavy chain CDR3 domain comprising the amino acid sequence of SEQ ID NO: 008, or modified from SEQ ID NO: 008.

More preferably, the antibody, or antigen-binding portion thereof, dissociates from human CD22 with a kd of 0.0685 RU s$^{-1}$ or less. Even more preferably, the antibody, or antigen binding portion thereof, dissociates from human CD22 with a kd of 0.0137 RU s$^{-1}$ or less.

In yet another embodiment, the invention provides methods of treating disorders in which the administration of an anti-CD22 antibody is beneficial by the biweekly, intravenous administration of an isolated chimeric and/or framework-patched (humanized) antibody, or an antigen-binding portion thereof. The antibody or antigen-binding portion thereof preferably contains a light chain variable region (LCVR) having a CDR3 domain comprising the amino acid sequence of SEQ ID NO: 004, or modified from SEQ ID NO: 004, and with a heavy chain variable region (HCVR) having a CDR3 domain comprising the amino acid sequence of SEQ ID NO: 008, or modified from SEQ ID NO: 008. Preferably, the LCVR further has a CDR2 domain comprising the amino acid sequence of SEQ ID NO: 003 and the HCVR further has a CDR2 domain comprising the amino acid sequence of SEQ ID NO: 007. Even more preferably, the LCVR further has CDR1 domain comprising the amino acid sequence of SEQ ID NO: 002 and the HCVR has a CDR1 domain comprising the amino acid sequence of SEQ ID NO: 006. The framework regions for VL preferably are from the VK10 murine germline family, and most preferably from the SM03 framework sequences shown in FIG. 4A of Chinese Pat. No. ZL03123054.7. The framework regions for VH preferably are from the VH5 murine germline family, and most preferably from the SM03 VH framework sequences shown in FIG. 4B in Chinese Pat. No ZL03123054.7. Yet more preferably, the framework one (FR1) regions for VL preferably are from the VκID human germline family, the framework two (FR2) regions for VL preferably are from the Vκ1human germline family, the framework three (FR3) regions for VL preferably are from the Vid human germline family, and the framework four (FR4) regions for VL preferably are from the VκJ1 human germline family, and most preferably from the SM06 framework sequences shown in FIG. 3B of U.S. Pat. No. 7,321,026 B2. The framework one (FR1) regions for VH preferably are from the $V_H3$ human germline family, the framework two (FR2) regions for VH preferably are from the $V_H3$ human germline family, the framework three (FR3) regions for VH preferably are from the $V_H3$ human germline family, and the framework four (FR4) regions for VH preferably are from the $V_HJ5$ human germline family, and most preferably from the SM06 framework sequences shown in FIG. 3A of U.S. Pat. No. 7,321,026 B2

In still another embodiment, the invention provides methods of treating disorders in which the administration of an anti-CD22 antibody is beneficial by the biweekly, intravenous administration of an isolated chimeric and/or framework-patched (humanized) antibody, or antigen-binding portion thereof. The antibody or antigen-binding portion thereof preferably contains a light chain variable region (LCVR) comprising the amino acid sequence of SEQ ID NO: 001 (i.e., the SM03 VL) and a heavy chain variable region (HVCR) comprising the amino acid sequence of SEQ ID NO: 005 (i.e., the SM03 VH). In certain embodiments, the antibody comprises a heavy chain constant region, such as an IgG1, IgG2, IgG3, IgG4, IgA, IgE, IgM or IgD constant region or any of the above constant region with the glycosylation site and/or the glycoforms at the glycosylation site modified. Preferably, the antibody comprises a kappa light chain constant region. Alternatively, the antibody portion can be, for example, a Fab fragment or a single chain Fv fragment.

An antibody or antibody portion of the invention can be derivatized or linked to another functional molecule (e.g., another peptide or protein). Accordingly, the antibodies and antibody portions of the invention are intended to include derivatized and otherwise modified forms of the human anti-CD22 antibodies described herein, including immunoadhesion molecules. For example, an antibody or antibody portion of the invention can be functionally linked (by chemical coupling, genetic fusion, noncovalent association or introduction of an artificial amino acid/functional group suitable for site-specific conjugation) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-huydroxysuccinimide ester) or homobifunctional (e.g., disuccinimidyle suberate). Such linkers are available from Thermo Scientific, Waltham, MA.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

III. Useful Cytotoxic Agents with which an Antibody or Antibody Portion of the Invention May be Derivatized for Conjugation Include Chemotherapeutic Agents Such as Alkynes Exemplary chemotherapeutic agents include calicheamicin, maytansinoids, and auristantins and the like. An antibody may also be derivatized with cytotoxic toxins, such as Diphtheria toxins, *Pseudomonas* exotoxin, A chain of Ricin, gelonin, pokeweed antiviral protein, dodecandron and the like. The derivatized antibody conjugated with chemotherapeutic agents or with cytotoxic toxins can be used as therapeutic agents for the treatment of autoimmune disease or cancers involving expression of human CD22 antigens.

IV. Expression of Antibodies

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniais (eds), *Molecular Cloning: A Laboratory Manual*, Second Edition, Cold Spring Harbor, N.Y., (1989), Ausubel, F. M. et al. (eds.) Current Protocols in Molecular Biology, Greene Publishing Assoviates, (1989) and in U.S. Pat. No. 4,816,397 by Boss et al.

To express SM03, SM06 or a SM03/SM06-related antibody, DNA fragments encoding the light and heavy chain variable regions are first obtained. These DNAs can be obtained by amplification and modification of hybridomas for the murine antibody light and heavy chain variable sequences using the polymerase chain reaction (PCR), or by oligosynthesis based on the encoded amino acid sequence of design light and heavy chain variable sequences using standard methods known to those skilled in the art. The encoding DNA sequences can be further optimized to facilitate mammalian expression of the resultant antibody.

Once the VH and VL fragments for the murine antibody are obtained, these sequences can be mutated to encode the framework-patched version of SM03 (i.e. SM06), the method of which was described in Chinese Pat. No. ZL 011 ZL 031 23054.7 and U.S. Pat. No. 7,321,026 B2 & 7,338, 659 B2 incorporated in its entirety herein by reference.

Once DNA fragments encoding SM03 or SM06, or SM03/SM06-related VH and VL segments are obtained (by amplification and mutagenesis of the original murine VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art. (see e.g., Kabat, E. A., et al (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, Ig4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al. (1990) Nature 348:552-554).

To express the antibodies, or antibody portions of the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the SM03, SM06 or SM03/SM06-related light or heavy chain sequences, the expression vector may already carry antibody constant regions sequences. For example, one approach to converting the SM03 or SM06 or SM03/SM06-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology: Methods in enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from immunoglobulin heavy chain (IgH) enhancer (Gillies et al. (1983) Cell 33:717-728) metallothioneine (MT), cytomegalovirus (CMV)(such as the CMV promoter/enhancer), Simian Virus 40 (SV40)(such as the SV40 promoter/enhancer), adenovirus, (e.g., the adenovirus major late promoter (AdMLP)) and polyoma.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced. For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification), Glutamate Synthase (GS) gene and the neo gene (for G418 selection).

For expression of the light and heavy chains, the expression vector encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, lipofection, protoplast fusion and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include SP2/0 myeloma cells, NS0 myeloma cells, COS cells, and Chinese Hamster Ovary (CHO cells) (including dfhr-CHO cells, described in Urlaub and Chasin, (1980) *Proc. Natl. Acad. Sci. USA* 77:4216-4200, used with a DHFR selectable marker, e.g., as described in R. J. Kaufman and P. A. Sharp (1982) *J Mol. Biol.* 159:601-621). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It will be understood that variations of the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to CD22. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than CD22 by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into SP2/0 cells by electroporation. In yet another preferred system for recombinant expression of an antibody, or antigen-binding portion thereof, of the invention, a recombinant expression vector encoding both the antibody heavy chain and the antibody light chain is introduced into CHO cells by standard techniques such as lipofection.

Within the recombinant expression vector, the antibody heavy and light chain genes are each operatively linked to murine or human Immunoglobulin heavy chain (IgH), CMV enhancer, metallothioneine or AdMLP promoter regulatory elements to drive high levels of transcription of the genes. The recombinant expression vector also carries a DHFR gene, which allows for selection of SP2/0 cells that have been transfected with the vector using methotrexate selection/amplification. Alternatively, the recombinant expression vector containing the antibody heavy and light chain genes operatively linked to murine or human IgH, CMV enhancer/AdMLP/metallothioneine promoter regulatory elements and a DHFR gene can be used to transfect SP2/0 or CHO cells that are dhfr⁻. SP2/0 or CHO cells transfected with the vector can be selected and the level of gene expression in the vector amplified by increasing the levels of methotrexate in the culture. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

V. Selection of Recombinant Human Antibodies

Recombinant human antibodies of the invention in addition to SM03, SM06 or an antigen binding portion thereof, or SM03-related antibodies that bind to the specific human CD22 discontinuous conformation epitope in domain 2 that disrupt human CD22 homomultimeric binding in cis as disclosed herein can be isolated by screening of a recombinant combinatorial antibody library, preferably a scFv phage display library, prepared using human VL and VH cDNAs prepared from mRNA derived from human lymphocytes. In another embodiment, the recombinant human antibodies bind to the anti-idiotype antibody (LRID). Methodologies for preparing and screening such libraries are known in the art. In addition to commercially available kits for generating phage display libraries (e.g., the GE Healthcare Life Sciences Recombinant Antibody Phage System (RAPS); and the New England Biolab Ph.DTM Phage Display Library Kit, catalog no. E81005), examples of methods and reagents particularly amenable for use in generating and screening antibody display libraries can be found in, for example, Fuchs et al. (1991) *Biotechnology* 9:1369-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3579-3580; Garrard et al. (1991) *Biotechnology* 9:1373-1377; Hoogenboom et al. (1991) *Nuc Acid Res* 19:4133-4137; and Barbas et al. (1991) *PNAS* 88:7978-7982.

In a preferred embodiment, to isolate murine, recombinant or human antibodies with high affinity and a low off rate constant for human CD22, a parent murine or chimeric anti-CD22 antibody having high affinity and a low off rate constant for human CD22 (e.g., the hybridoma for murine anti-CD22 antibody deposited in ATCC with accession number: 7621) is first used to select human heavy and light chain sequences having similar binding activity toward human CD22, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., Nature (1990) 348:552-554; and Griffiths et al., (1993) EMBO J 12:725-734. The scFv antibody libraries preferably are screened using recombinant human CD22 (2-4 domains), and/or an anti-idiotype antibody specific for the antigen binding site (ABS) of the anti-CD22 antibody (e.g. LRID as described in U.S. Pat. No. 9,371, 396B) as the antigen.

Once initial human VL and VH segments are selected, "mix and match" experiments, in which different pairs of the initially selected VL and VH segments are screened for human CD22 binding, are performed to select preferred VL/VH pair combinations. Additionally, to further improve the affinity and/or lower the off rate constant for human CD22 (or recombinant CD22 (2-4) domains) binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to human CD22, preferably to the recombinant protein containing domains 2-4 of CD22, and/or binding to an anti-idiotype antibody of the anti-CD22 antibody (e.g. LRID); and sequences that exhibit high affinity and a low off rate for human CD22, preferably recombinant CD22 (2-4) domain, and/or an anti-idiotype antibody for CD22 (e.g. LRID) binding can be selected.

Following screening and isolation of an anti-human CD22 antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to a nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cell, as described in further detail in Section II above.

VI. Pharmaceutical Compositions and Pharmaceutical Administration

The antibodies and antibody-portions of the invention can be incorporated into pharmaceutical compositions suitable for administration to a subject for the methods described herein, e.g., two or three cycles (or multiple cycles) of biweekly, intravenous dosing. Typically, the pharmaceutical composition comprises an antibody (or antibody portion) of the invention and/or methotrexate and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible and are suitable for administration to a subject for the methods described herein. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular injection. In a particularly preferred embodiment, the antibody is administered by subcutaneous injection (e.g., multiple cycles of biweekly, subcutaneous injection).

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation and vacuum drying and freeze-drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection. As will be appreciated by those skilled in the art, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyethylene glycol (PEG), polyanhydrides, polyglycolic acid, collagen, polyorthoesteers, and polylactic acid. Many methods for the preparation of such formulations are patented or generally known to those skilled in the art. See, e.g., Sustained and Controlled Release Drug Delivery Systems, J. R. Robinson ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents. For example, an anti-CD22 antibody or antibody portion of the invention may be coformulated and/or coadministered with methotrexate, one or more additional antibodies that bind other targets (e.g., antibodies that bind soluble factors such as TNFα, TNFα receptors, other cytokines or that bind cell surface molecules), one or more soluble factors and cytokines, receptors and/or one or more chemical agents that inhibit B cell activities and/or the production of other effector molecules (such as IL1β, IL6, IL12, IL13, IL17A, IL20, IL22, IL23, TNFα) eliciting autoimmune symptoms. Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies. The use of the antibodies, or antibody portions, or the invention in combination with other therapeutic agents is discussed further below.

Non-limiting examples of therapeutic agents for rheumatoid arthritis with which an antibody, or antibody portion, of the invention can be combined include the following: non-steroidal anti-inflammatory drugs(s) (NSAIDs); cytokine suppressive anti-inflammatory drug(s) (CSAIDs); CDP-571/BAY-10-3356 (humanized anti-TNFα antibody; Celltech/Bayer); cA2 (chimeric anti-TNFα antibody; Centocor); 75 D2E7 (fully human anti-TNFα antibody; CAT/Abbott); CNT0148 (fully human anti-TNFα antibody; Centocor/Janssen); AIN457 (fully human anti-IL17A antibody; Novartis); CAM3001 (fully human anti-GMCSF Receptor antibody; CAT/Medimmune); Tocilizumab (humanized anti-IL6 receptor antibody; Chugai/Hoffman-LaRoche); 75kdTNFR-IgG (75 kD TNF receptor-IgG fusion protein; Immunex; see e.g., Arthritis & Rheumatism (1994) Vol. 37, 5295; J. Invest. Med. (1996) Vol. 44, 235A); 55 kdTNFR-IgG (55 kD TNF receptor-IgG fusion protein; Hoffmann-LaRoche): IDEC-CE9.1/SB 210396 (non-depleting primatized anti-CD4 antibody; IDEC/SmithKline; see e.g., Arthritis & Rheumatism (1995) Vol. 38, S185); DAB 486-IL-2 and/or DAB 389-IL-2 (IL-2 fusion proteins; Seragen; see e.g., Arthritis & Rheumatism (1993) Vol. 36, 1223); Anti-Tac (humanized anti-IL-2Ra; Protein Design Labs/Roche); IL-3 (anti-inflammatory cytokine; DNAS/Schering); IL-10 (SCH 52000; recombinant IL-10, anti-inflammatory cytokine; DNAX/Schering); IL-4; IL-10 and/or IL-4 agonists (e.g., agonist antibodies); IL-1 RA (IL-1 receptor antagonist; Synergen/Amgen); TNF-bp/s-TNFR (soluble TNF binding protein; see e.g., Arthritis & Rheumatism (1996) Vol. 39, No. 9 (supplement), 5284; Amer. J. Physiol. Heart and Circulatory Physiology (1995) Vol. 268, pp. 37-42); R973401 (phosphodiesterase Type IV inhibitor; see e.g., Arthritis & Rheumatism (1996) Vol. 39, No. 9 (supplement), S82); (methotrexate; thalidomide (see e.g., Arthritis & Rheumatism (1996) Vol. 39, No. 9 (supplement), 5282) and thalidomide-related drugs (e.g., Celgen); leflunomide (anti-inflammatory and cytokine inhibitor; see e.g., Arthritis & Rheumatism (1996) Vol. 39, No. 9 (supplement), 5131; Inflammation Research (1996) Vol. 39, No. 9 (supplement), 5131; Inflammation Research (1996) Vol. 45, pp. 103-107); tranexamic acid (inhibitor of plasminogen activation; see e.g., Arthritis & Rheumatism (1996) Vol. 39, No. 9 (supplement), S284); Janus kinase (JAK1, JAK2, JAK3, TYK2) inhibitors (see e.g., Banerjee et al. (2017) Drugs 77:521-545); T-614 (cytokine inhibitor; see e.g., Arthritis & Rheumatism (1996) Vol. 39, No. 9 (supplement), S282); prostaglandin E1 (see e.g., Arthritis & Rheumatism (1996) Vol. 39, No. 9 (supplement), S282); Tenidap (non-steroidal anti-inflammatory drug; see e.g., Arthritis & Rheumatism (1996) Vol. 39, No. 9 (supplement), S280); Naproxen (non-steroidal anti-inflammatory drug; see e.g., Neuro Report (1996) Vol. 7, pp. 1209-1213); Meloxicam (non-steroidal anti-inflammatory drug); Ibuprofen (non-steroidal anti-inflammatory drug); Indomethacin (non-steroidal anti-inflammatory drug); Sulfasalazine (see e.g., Arthritis & Rheumatism (1996) Vol. 39, No. 9 (supplement), S281); Azathioprine (see e.g., Arthritis & Rheumatism (1996) Vol. 39, No. 9 (supplement), S281); ICE inhibitor (inhibitor of the enzyme interleukin-1β converting enzyme); zap-70 and/or 1 ck inhibitor (inhibitor of the tyrosine kinase zap-70 or 1 ck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL 12 antibodies; interleukin-11 (see e.g., Arthritis & Rheumatism (1996) Vol. 39, No. 9 (supplement), S296); interleukin-13 (see e.g., Arthritis & Rheumatism (1996) Vol. 39, No. 9 (supplement), S308); interleukin-17 inhibitors (see e.g., Arthritis & Rheumatism (1996) Vol. 39, No. 9 (supplement), S120); gold; penicillamine; chloroquine; hydroxychloroquine; chlorambucil; cyclophosphamide, cyclosporine; total lymphoid irradiation; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysuphate; minocycline; anti-IL2R antibodies; marine and botanical lipids (fish and plant seed fatty acids; see e.g., DeLuca et al. (1995) Rheum. Dis. Clin. North Am. 21:759-777); auranofin; phenylbutazone;

meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); and azaribine.

Non-limiting examples of therapeutic agents for inflammatory bowel disease with which an antibody, or antibody portion, of the invention can be combined include the following: budenoside; epidermal growth factor; corticosteroids; cyclosporine, sulfasalazine; aminosalicycates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinylimidazole compounds; CDP-571/BAY-10-3356 (humanized anti-TNFα antibody; Celltech/Bayer); cA2 (chimeric anti-TNFα antibody; Centocor); 75 kdTNFR-IgG (75 dD TNF receptor-IgG fusion protein; Immunex; see e.g., Arthritis & Rheumatism (1994) Vol. 37, S295; J. Invest. Med. (1996) Vol. 44, 235A); 55 kdTNFR-IgG (55 kD TNF receptor-IgG fusion protein; Hoffmann-LaRoche): interleukin-10 (SCH 52000; Schering Plough); IL-4; IL-10 and/or IL-4-agonists (e.g., agonist antibodies); interleukin-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slowrelease mesalazine; methotrexate; antagonists of Platelet Activating Factor (PAF); ciprofloxacin; and lignocaine.

Nonlimiting examples of therapeutic agents for multiple sclerosis with which an antibody, or antibody portion, of the invention can be combined include the following: corticosteroids; prednisolone; methylprednisolone; azathioprine; cyclophosphamide; cyclosporine; methotrexate; 4-aminopyridine; tizanidine; interferon-β1a (Avonex™; Biogen); interferon-β1b (Betseron™; Chiron/Berlex); Copolymer 1 (Cop-1; Copaxone™; Teva Pharmaceutical Industries, Inc.); hyperbaric oxygen; intravenous immunoglobulin; clabribine; CDP-571/BAY-10-3356 (humanized anti-TNFα antibody; Celltech/Bayer); cA2 (chimeric anti-TNFα antibody; Centocor); 75 kdTNFR-IgG (75 dD TNF receptor-IgG fusion protein; Immunex; see e.g., Arthritis & Rheumatism (1994) Vol. 37, 5295; J. Invest. Med. (1996) Vol. 44, 235A); 55 kdTNFR-IgG (55 kD TNF receptor-IgG fusion protein; Hoffmann-LaRoche); IL-10; IL-4; and IL-10 and/or IL-4 agonists (e.g., agonist antibodies).

Nonlimiting examples of therapeutic agents for Sjogren's syndrome with which an antibody, or antibody portion, of the invention can be combined include the following: cytokine suppressive anti-inflammatory drug(s) (CSAIDs); CDP-571/BAY-10-3356 (humanized anti-TNFα antibody; Celltech/Bayer); cA2 (chimeric anti-TNFα antibody; Centocor); 75 D2E7 (fully human anti-TNFα antibody; CAT/Abbott); CAM3001 (fully human anti-GMCSF Receptor antibody; CAT/Medimmune); CNT0148 (fully human anti-TNFα antibody; Centocor/Janssen); AIN457 (fully human anti-IL17A antibody; Novartis); Tocilizumab (humanized anti-IL6 receptor antibody; Chugai/Hoffman-LaRoche); 75kdTNFR-IgG (75 kD TNF receptor-IgG fusion protein; Immunex; see e.g., Arthritis & Rheumatism (1994) Vol. 37, 5295; J. Invest. Med. (1996) Vol. 44, 235A); 55 kdTNFR-IgG (55 kD TNF receptor-IgG fusion protein; Hoffmann-LaRoche): IDEC-CE9.1/SB 210396 (non-depleting primatized anti-CD4 antibody; IDEC/SmithKline; see e.g., Arthritis & Rheumatism (1995) Vol. 38, S185); DAB 486-IL-2 and/or DAB 389-IL-2 (IL-2 fusion proteins; Seragen; see e.g., Arthritis & Rheumatism (1993) Vol. 36, 1223); Anti-Tac (humanized anti-IL-2Ra; Protein Design Labs/Roche); IL-3 (anti-inflammatory cytokine; DNAS/Schering); IL-10 (SCH 52000; recombinant IL-10, anti-inflammatory cytokine; DNAX/Schering); IL-4; IL-10 and/or IL-4 agonists (e.g., agonist antibodies); IL-1 RA (IL-1 receptor antagonist; Synergen/Amgen); TNF-bp/s-TNFR (soluble TNF binding protein; see e.g., Arthritis & Rheumatism (1996) Vol. 39, No. 9 (supplement), 5284; Amer. J. Physiol. Heart and Circulatory Physiology (1995) Vol. 268, pp. 37-42); R973401 (phosphodiesterase Type IV inhibitor; see e.g., Arthritis & Rheumatism (1996) Vol. 39, No. 9 (supplement), S82); (methotrexate; thalidomide (see e.g., Arthritis & Rheumatism (1996) Vol. 39, No. 9 (supplement), 5282) and thalidomide-related drugs (e.g., Celgen); leflunomide (anti-inflammatory and cytokine inhibitor; see e.g., Arthritis & Rheumatism (1996) Vol. 39, No. 9 (supplement), 5131; Inflammation Research (1996) Vol. 39, No. 9 (supplement), 5131; Inflammation Research (1996) Vol. 45, pp. 103-107); tranexamic acid (inhibitor of plasminogen activation; see e.g., Arthritis & Rheumatism (1996) Vol. 39, No. 9 (supplement), S284); Janus kinase (JAK1, JAK2, JAK3, TYK2) inhibitors (see e.g., Banerjee et al. (2017) Drugs 77:521-545); T-614 (cytokine inhibitor; see e.g., Arthritis & Rheumatism (1996) Vol. 39, No. 9 (supplement), S282); prostaglandin E1 (see e.g., Arthritis & Rheumatism (1996) Vol. 39, No. 9 (supplement), S282); Tenidap (non-steroidal antiinflammatory drug; see e.g., Arthritis & Rheumatism (1996) Vol. 39, No. 9 (supplement), S280); Naproxen (non-steroidal anti-inflammatory drug; see e.g., Neuro Report (1996) Vol. 7, pp. 1209-1213); Meloxicam (non-steroidal anti-inflammatory drug); Ibuprofen (non-steroidal anti-inflammatory drug); Indomethacin (non-steroidal anti-inflammatory drug); Sulfasalazine (see e.g., Arthritis & Rheumatism (1996) Vol. 39, No. 9 (supplement), S281); Azathioprine (see e.g., Arthritis & Rheumatism (1996) Vol. 39, No. 9 (supplement), S281); ICE inhibitor (inhibitor of the enzyme interleukin-1β converting enzyme); zap-70 and/or 1 ck inhibitor (inhibitor of the tyrosine kinase zap-70 or 1 ck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL 12 antibodies; interleukin-11 (see e.g., Arthritis & Rheumatism (1996) Vol. 39, No. 9 (supplement), S296); interleukin-13 (see e.g., Arthritis & Rheumatism (1996) Vol. 39, No. 9 (supplement), S308); interleukin-17 inhibitors (see e.g., Arthritis & Rheumatism (1996) Vol. 39, No. 9 (supplement), S120); gold; penicillamine; chloroquine; hydroxychloroquine; chlorambucil; cyclophosphamide, cyclosporine; total lymphoid irradiation; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysuphate; minocycline; anti-IL2R antibodies; marine and botanical lipids (fish and plant seed fatty acids; see e.g., DeLuca et al. (1995) Rheum. Dis. Clin. North Am. 21:759-777); auranofin; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); and azaribine.

Non-limiting examples of therapeutic agents for systemic lupus erythematosus (SLE) with which an antibody, or antibody portion, of the invention can be combined include the following: corticosteroids; prednisolone; methylprednisolone; azathioprine; cyclophosphamide; cyclosporine; methotrexate; 4-aminopyridine; tizanidine; interferon-β1a (Avonex™; Biogen); interferon-β1b (Betseron™; Chiron/Berlex); Copolymer 1 (Cop-1; Copaxone™; Teva Pharmaceutical Industries, Inc.); hyperbaric oxygen; intravenous immunoglobulin; clabribine; CDP-571/BAY-10-3356 (humanized anti-TN Fa antibody; Celltech/Bayer); cA2 (chimeric anti-TNFα antibody; Centocor); 75 D2E7 (fully human anti-TNFα antibody; CAT/Abbott); CNT0148 (fully human anti-TNFα antibody; Centocor/Janssen); CAM3001 (fully human anti-GMCSF Receptor antibody; CAT/Medimmune); AIN457 (fully human anti-IL17A antibody; Novartis); 75 kdTNFR-IgG (75 dD TNF receptor-IgG fusion protein; Immunex; see e.g., Arthritis & Rheumatism (1994) Vol. 37, 5295; J. Invest. Med. (1996) Vol. 44, 235A); 55 kdTNFR-IgG (55 kD TNF receptor-IgG fusion protein; Hoffmann-LaRoche); IL-10; IL-4; and IL-10 and/or IL-4 agonists (e.g., agonist antibodies);); IL-1 RA (IL-1 receptor antagonist; Synergen/Amgen); TNF-bp/s-TNFR (soluble TNF binding protein; see e.g., Arthritis & Rheumatism (1996) Vol. 39, No. 9 (supplement), 5284; Amer. J. Physiol. Heart and Circulatory Physiology (1995) Vol. 268, pp. 37-42); R973401 (phosphodiesterase Type IV inhibitor; see e.g., Arthritis & Rheumatism (1996) Vol. 39, No. 9 (supplement), S82); (methotrexate; thalidomide (see e.g., Arthritis & Rheumatism (1996) Vol. 39, No. 9 (supplement), S282) and thalidomide-related drugs (e.g., Celgen); leflunomide (anti-inflammatory and cytokine inhibitor; see e.g., Arthritis & Rheumatism (1996) Vol. 39, No. 9 (supplement), S131; Inflammation Research (1996) Vol. 39, No. 9 (supplement), S131; Inflammation Research (1996) Vol. 45, pp. 103-107); tranexamic acid (inhibitor of plasminogen activation; see e.g., Arthritis & Rheumatism (1996) Vol. 39, No. 9 (supplement), S284); Janus kinase (JAK1, JAK2, JAK3, TYK2) inhibitors (see e.g., Banerjee et al. (2017) Drugs 77:521-545); T-614 (cytokine inhibitor; see e.g., Arthritis & Rheumatism (1996) Vol. 39, No. 9 (supplement), S282); prostaglandin E1 (see e.g., Arthritis & Rheumatism (1996) Vol. 39, No. 9 (supplement), S282); Tenidap (non-steroidal anti-inflammatory drug; see e.g., Arthritis & Rheumatism (1996) Vol. 39, No. 9 (supplement), S280); Naproxen (non-steroidal anti-inflammatory drug; see e.g., Neuro Report (1996) Vol. 7, pp. 1209-1213); Meloxicam (non-steroidal anti-inflammatory drug); Ibuprofen (non-steroidal anti-inflammatory drug); Indomethacin (non-steroidal anti-inflammatory drug); Sulfasalazine (see e.g., Arthritis & Rheumatism (1996) Vol. 39, No. 9 (supplement), S281); Azathioprine (see e.g., Arthritis & Rheumatism (1996) Vol. 39, No. 9 (supplement), S281); ICE inhibitor (inhibitor of the enzyme interleukin-1β converting enzyme); zap-70 and/or 1 ck inhibitor (inhibitor of the tyrosine kinase zap-70 or 1 ck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL 12 antibodies; interleukin-11 (see e.g., Arthritis & Rheumatism (1996) Vol. 39, No. 9 (supplement), S296); interleukin-13 (see e.g., Arthritis & Rheumatism (1996) Vol. 39, No. 9 (supplement), S308); interleukin-17 inhibitors (see e.g., Arthritis & Rheumatism (1996) Vol. 39, No. 9 (supplement), S120); gold; penicillamine; chloroquine; hydroxychloroquine; chlorambucil; cyclophosphamide, cyclosporine; total lymphoid irradiation; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysuphate; minocycline; anti-IL2R antibodies; marine and botanical lipids (fish and plant seed fatty acids; see e.g., DeLuca et al. (1995) Rheum. Dis. Clin. North Am. 21:759-777); auranofin; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); and azaribine.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

For illustrative purposes, for example, non-limiting range for a therapeutically or prophylactically effective amount of an antibody or antibody portion of the invention is 100-1000 mg, more preferably 400-800 mg and most preferably about 600 mg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set

VII. Utilities of the Antibodies of the Invention

The anti-CD22 antibodies, or portions thereof, of the present invention have the ability to bind to human CD22, specifically against a recombinant protein containing domain 2-4 of human CD22, more specifically, against domain 2, and even more specifically, the discontinuous conformational epitope containing the sequences $_{161}$CLLNFSCYGYPIQ$_{173}$ (SEQ ID NO: 016) & $_{198}$VFTRSELKFSPQWSHHGKIVTC$_{219}$ (SEQ ID NO: 017); and the ability to bind to an anti-idiotype antibody against the anti-CD22 antibody, specifically, the LRID antibody. Accordingly, the anti-CD22 antibodies, or portions thereof, of the invention can be used to detect human CD22 positive cells or soluble human CD22 containing the aforementioned conformational epitope (e.g., in a biological sample containing infiltrating lymphocytes), or the anti-idiotype antibody, or cell lines expressing portions of the anti-idiotype antibody on the cell surface, using a conventional immunoassay, such as a flow cytometry analysis, a radioimmunoassay (RIA), an enzyme linked immunosorbent assay (ELISA), or tissue immunohistochemistry.

The invention provides a method for detecting human CD22 positive cells or soluble human CD22, or the anti-idiotype antibody against the anti-CD22 antibody, or cell lines expressing portions of the anti-idiotype antibody on the cell surface, in a biological sample comprising contacting a biological sample with an antibody, or antibody portion, of the invention and detecting either the antibody (or antibody portion) bound to human CD22 positive cells or soluble human CD22, or the anti-idiotype antibody against the anti-CD22 antibody, or cell lines expressing portions of the anti-idiotype antibody on the cell surface, or unbound antibody (or antibody portion), to hereby detect human CD22 positive cells or soluble human CD22 or anti-idiotype antibody against the anti-CD22 antibody or cell lines expressing portions of the anti-idiotype antibody on the cell surface in the sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I $^{35}$S or $^{3}$H.

Alternative to labeling the antibody, human CD22 positive cells or soluble human CD22 or anti-idotype antibody against the anti-CD22 antibody or cell lines expressing portion of the anti-idiotype antibody on the cell surface can be assayed in biological fluids by a competitive immunoassay utilizing recombinant human CD22 or recombinant human CD22 domains 2-4 as standards or recombinant domains containing the discontinuous conformational epitope encompassing the sequences $_{161}$CLLNFSCYGYPIQ$_{173}$ & $_{198}$VFTRSELKFSPQWSHHGKIVTC$_{219}$ or anti-idiotype antibody against the anti-CD22 antibody or cell lines expressing portions of the anti-idiotype antibody on the cell surface which are labeled with a detectable substance and an unlabeled anti-CD22 antibody. In this assay, the biological sample, the labeled standards, which can be human CD22 or sequence fragments containing the discontinuous conformational epitope (containing $_{161}$CLLNFSCYGYPIQ$_{173}$ & $_{198}$VFTRSELKFSPQWSHHGKIVTC$_{219}$), or the anti-idiotype antibody against the anti-CD22 antibody, and the anti-CD22 antibody are combined and the amount of labeled standard bound to the unlabeled antibody is determined. The amount of human CD22 or anti-idiotype antibody against the anti-CD22 antibody in the biological sample is inversely proportional to the amount of labeled standard bound to the anti-CD22 antibody.

Although anti-human CD22 antibodies do not cross react with non-primate CD22, the antibodies and antibody portions of the invention can be used in human subjects or in other mammalian (e.g. primates) subjects other than therapeutic purposes.

In a preferred embodiment, the invention provides methods of treating disorders in which the administration of an anti-CD22 antibody is beneficial, comprising intravenously administering to the subject in biweekly cycles an antibody or antibody portion of the invention such that the disorder is treated. In a particularly preferred embodiment, the antibody is administered intravenously on a biweekly schedule in multiple cycles. In another particularly preferred embodiment, the antibody is administered intravenously before, during or after administration of methotrexate. Preferably, the subject is a human subject. Alternatively, the subject can be a mammal expressing a CD22 with which an antibody of the invention crossreacts. Still further the subject can be a mammal into which has been introduced human CD22 (e.g., by administration of human CD22 or by expression of a human CD22 transgene) or an anti-idiotype antibody against the anti-CD22 antibody (e.g., by administration of an anti-idiotype antibody against the anti-CD22 antibody, or by expression of an anti-idiotype antibody transgene). An antibody of the invention can be administered to a human subject for therapeutic purposes (discussed further below). Moreover, an antibody of the invention can be administered to a non-human mammal expressing a cross-reacting CD22 or a surrogate antigen (e.g., in a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which the administration of an anti-CD22 antibody is beneficial" is intended to include diseases and other disorders in which the overexpression of CD22 in a particular cell type or in a group of cells in a subject suffering from the disorder, or the modulation of activities of cells expressing CD22 in a subject suffering from the disorder via interactions with the antibodies and antibody portions of the invention, has been shown to be or is suspected of being either responsible for the pathophysiology of the disorder or a factor that contributes to a worsening (overexpression of CD22 positive cells) or an improvement (modulation of CD22 positive cells) of the disorder, or where it has been shown that another anti-CD22 antibody or a biologically active portion thereof has been successfully used to treat the disease. Accordingly, a disorder in which CD22 positive cell overactivity, or cells overexpressing CD22 is detrimental is a disorder in which modulation of CD22 positive cell activities is expected to alleviate the symptoms and/or progression of the disorder.

Such disorders may be evidenced, for example, by an increase of CD22 positive cell population in the biological fluid of a subject suffering from the disorder (e.g., an increase in the population of CD22 positive cells in circulation, synovial fluid, lesions etc. of the subject), which can be detected, for example, using an anti-CD22 antibody as described above. There are examples of disorders in which CD22 positive cell overactivity is detrimental.

The use of the antibodies and antibody portions of the invention in the treatment of specific disorders is discussed further below:

A. Autoimmune Diseases

B cells have been implicated in playing a role in the pathophysiology of a variety of autoimmune diseases. For example, B cells are present in inflamed synovial tissue in rheumatoid arthritis (RA) patients. In RA patients, B cells produce autoantibodies that activate phagocytes and complement. B cell also present autoantigens and provide costimulatory signals to autoreactive T cells and produce cytokines that further activate B cell, T cells and other inflammatory cells. B cells may also serve as antigen presenting cells for T cells and provide co-stimulatory signal for T cell activation. Chimeric and humanized murine anti-CD22 antibodies have undergone clinical testing for treatment of rheumatoid arthritis and other autoimmune diseases and the results are disclosed herein (see Examples 4 & 5).

The chimeric and/or framework-patched (humanized) antibodies, and antibody portions of the invention can be used to treat autoimmune diseases, in particular those associated with inflammation, including rheumatoid arthritis, rheumatoid spondylitis, osteoarthritis and gouty arthritis, allergy, multiple sclerosis, autoimmune diabetes, autoimmune uveitis, nephrotic syndrome, sjögren's diseases, systemic lupus erythematosus (SLE), etc. Typically, the antibody, or antibody portion, is administered systemically, although for certain disorders, local administration of the antibody or antibody portion at a site of inflammation may be beneficial.

B. Transplantation

Immunosuppressive strategies in solid organ transplantation have mostly focused on depleting T cells or inhibiting their function. However, there has been increasing interest in the role played by B cells, plasma cells and their associated antibody, in the immune response to an allograft, initially driven by the need to reexplore the feasibility of antibody-incompatible transplantation.

According to another embodiment, the antibodies, and antibody portions, of the invention, can be used to inhibit transplant rejection, including rejections of allografts and xenografts and to inhibit graft versus host disease (GHVD). According to another embodiment, the antibodies are used to treat acute cellular rejection or acute and chronic antibody-mediated rejection.

Although the antibody or antibody portion may be used alone, more preferably it is used in combination with one or more other agents that inhibit the immune response against the allograft or inhibit GVHD. For example, in one embodiment, an antibody or antibody portion of the invention is used in combination with OKT3 to inhibit OKT3-induced reactions. In another embodiment, an antibody or antibody portion of the invention is used in combination with one or more antibodies directed at other targets involved in regulation immune responses, such as the cell surface molecules CD25 (interleukin-2 receptor-α), CD11a (LFA-1), CD54 (ICAM-1), CD4, CD45, CD28/CTLA4, CD80 (B7-1) and/or CD86 (B7-2). In yet another embodiment, an antibody or antibody portion of the invention is used in combination with one or more general immunosuppressive agents, such as cyclosporine A or FK506.

C. Malignancy

Another embodiment provides antibodies, and antibody portions, for treatment of malignancies related to overexpression of the CD22 antigen. Malignancies related to overexpression of the CD22 antigen include, but are not limited to, B cell lymphoma, such as acute lymphoblastic leukemia, chronic lymphocytic leukemia, non-Hodgkin's lymphoma, follicular lymphoma, diffuse large B-cell lymphoma, mantle cell lymphoma. The antibody, or antibody portion, may be administered systemically or locally to the tumor site.

This invention is further illustrated by the following examples which should not be construed as limiting. The contents of all references, patents and published patent applications cited throughout this application are hereby incorporated by reference.

Example 1

Kinetic Analysis of Binding of Anti-CD22 Antibodies to CD22 and Surrogate Antigens/Anti-Idiotype Antibodies Affinity of anti-CD22 antibodies against human CD22 was performed using BIAcore (GE Healthcare Life Sciences, Piscataway, NJ) according to standard procedures. Briefly, human recombinant CD22 (20 µg/ml, PeproTech, Rocky Hill, NJ) was immobilized on carboxymethylated dextran-coated CM5 sensor chip. The chip surface was firstly activated with N-ethyl-N'-(3-diethylaminopropyl) carbodiimide hydrochloride (EDC) and N-hydroxysuccinimide (NHS). Different concentrations of anti-CD22 antibodies, and in this case, SM03 (1.0625-34 nmol/ml) in phosphate buffer saline (PBS) were injected at a flow rate of 20 µL/min for 3 min. The residual carboxyl groups were subsequently blocked by 1M ethanolamine (pH 8.5). The dissociation was studied by washing with running buffer for 3 min. The chip surface was then regenerated by injection with 50 mM glycine-Cl for 60 s. Kinetic parameters including ka (association rate constant) and kd (dissociation rate constant) were estimated using the BIA evaluation software. The specific binding curves were normalized by subtracting the control curve.

FIG. 1 shows the kinetic analysis of the anti-CD22 antibody SM03 to immobilized recombinant human CD22 antigen. The overlay plot shows sensorgrams of 6 different concentrations of the anti-CD22 antibody (SM03) binding to the human CD22 antigen. Binding response is shown in response unit (RU). Results of different concentrations of SM03 (top to bottom: lowest concentration to highest concentration) binding to CD22 were shown (FIG. 1). The affinity parameters obtained were: ka=$1.13\times10^7$ RU/s; kd=0.0137 RU/s; Kd=$1.22\times10^{-9}$ M; Ka=$0.82\times10^9$ $M^{-1}$.

Preliminary epitope mapping analyses indicated that the epitope for the anti-CD22 antibodies SM03 and SM06 resided in the extracellular domain 2-4 of the human CD22 antigen (SEQ ID: 011). A recombinant human CD22 encompassing these domains (CD22d2-4) was therefore constructed and expressed as inclusion bodies in bacteria following standard procedures in molecular biology and bacterial expression. The refolded inclusion bodies were used as the source of natural antigen and the process of which was previously described (Zhang et al. 2010. Quantification of anti-CD22 monoclonal antibody concentration by enzyme-immunoassay. Chinese J New Drugs 2010; 19:253-7). As an alternative source of surrogate antigen for evaluating the activities of the anti-CD22 antibodies, an anti-idiotype antibody (LRID) that binds to the antigen-binding-site (ABS) of SM03 and SM06 were developed using Phage-display library (Zhao et al., 2014. Generation of anti-idiotype scFv for pharmacokinetic measurement in lymphoma patients treated with chimera anti-CD22 antibody SM03. PLOS ONE 9(5): e96697). The antibody was also described in Chinese Pat. No. ZL201210286457.4 and U.S. Pat. No. 9,371,396 B2 (which are incorporated in its entirety herein by reference.). Briefly, the single-chain Fvs (scFVs) specific for the antigen binding site of SM03 and SM06 were obtained from a Phage-display library from mice immunized with SM03 using techniques known to those skilled in the art. The scFv selected were re-engineered as a murine IgG antibody (LRID) using standard techniques in molecular biology. The LRID murine antibody was used as a surrogate antigen for CD22. For direct binding studies against the recombinant CD22 and the surrogate antigen, increasing concentrations of SM03 or SM06 were added into the wells of ELISA plates coated with 5-10 μg/ml of either human CD22d2-4 or LRID, and the extent of binding of these antibodies were revealed at $OD_{450}$ with HRP-conjugated goat anti-human Fc-specific antibodies (Jackson ImmunoResearch, West Grove, PA) after the addition of TMB substrates (Life Technologies, Carlsbad, CA) and stop solution ($H_2SO_4$). FIG. 2 shows the ELISA binding studies of anti-CD22 antibodies (SM03 and SM06) against (A) domain 2-4 of recombinant human CD22 antigen (CD22d2-4) (SEQ ID 011), and (B) an anti-idiotype antibody (LRID) specific for the antigen-binding-site (ABS) of SM03. The typical dose response curves for SM03 and SM06 binding to CD22d2-4 or LRID are shown in FIG. 2. Their respective $EC_{50}$ are summarized in TABLE 1.

TABLE 1

EC50 of Anti-CD22 Antibodies Against CD22 domains 2-4 (CD22d2-4) and Anti-idiotype Antibody for SM03 (LRID)

| $EC_{50}$ (μg/ml) | SM03 | SM06 |
| --- | --- | --- |
| CD22d2-4 | 0.100 ± 0.093 | 0.140 ± 0.102 |
| LRID | 0.080 ± 0.028 | 0.065 ± 0.028 |

Example 2

Figure 3B:
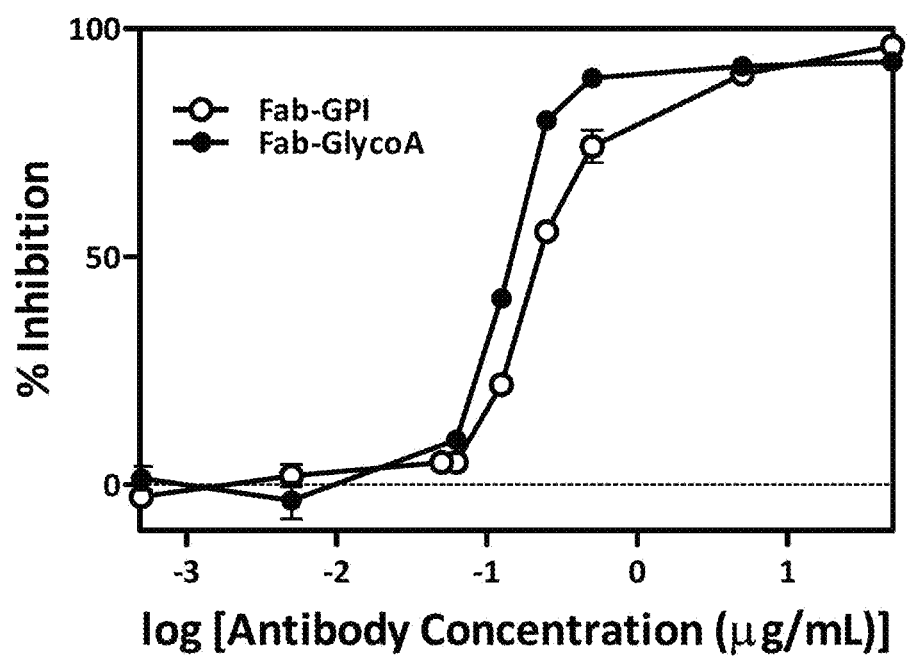
FIG. 3(B) is a dose response curve showing SM03-induced CMC killing effect against the Fab-GlycoA and Fab-GPI surrogate target cell according to an example embodiment.

Functional Activities of Anti-CD22 Antibodies Against Surrogate Target Cell Lines Expressing on the Cell Surface with a Binding Moiety Specific for the Anti-CD22 Antibodies FIG. 3 shows the murine myeloma SP2/0 cells transfected with expression vector encoding the Fab fragment of the anti-idiotype antibody against SM03 (LRID Fab) fused either to the transmembrane portion of Glycophorin A (Fab-GlycoA) or the glycophosphatidylinosito (GPI) signal sequence from decay accelerating factor (DAF) protein demonstrated high level of surface expression of LRID Fab (FIG. 3A) and these cells can be used as the surrogate target cells for the induction of CMC inhibition by the anti-CD22 antibodies SM03 and SM06. Exemplary SM03-induced CMC killing against the Fab-GlycoA and Fab-GPI surrogate target cell is shown (FIG. 3B). SP2/0 murine myeloma cells that express endogenous 10 were transfected with vectors containing sequences encoding LRID Fab fused to either the transmembrane portion of glycophorin A or the glycophosphatidylinositol (GPI) signal sequence from decay accelerating factor (DAF) protein. Cell lines that expressed on their surfaces with LRID Fab (SM03 and SM06 binding moiety) were used as the surrogate target cells for evaluating the functional activities of the anti-CD22 antibodies, SM03 and SM06. The construction of the cell lines and their uses were previously described (Leung et al. (2015) MAbs7(1):66-76; also in Chinese Pat. No. ZL201210286457.4 and U.S. Pat. No. 9,371,396 B2, incorporated in its entirety herein by reference.) Cells transfected with LRID Fab'-glycophorin A (Fab-GlycoA) or LRID Fab'-DAF (Fab-GPI) fusion protein constructs were shown to exhibit strong surface expression, manifested as dose-dependent binding of SM03 in flow cytometry studies (FIG. 3A).

Figure 4A:
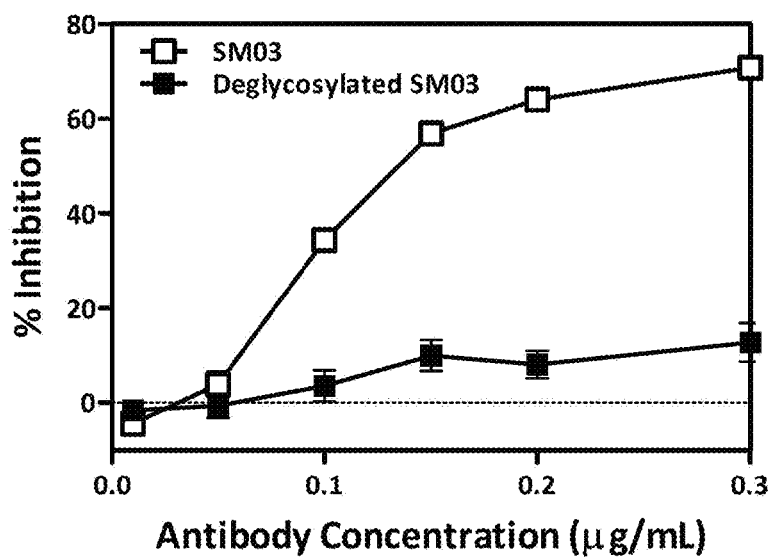
FIG. 4(A) is a dose response curve showing SM03 deglycosylated by PNGase treatment was demonstrated to have lost the biological function in inducing CMC activities according to an example embodiment.
Figure 4B:
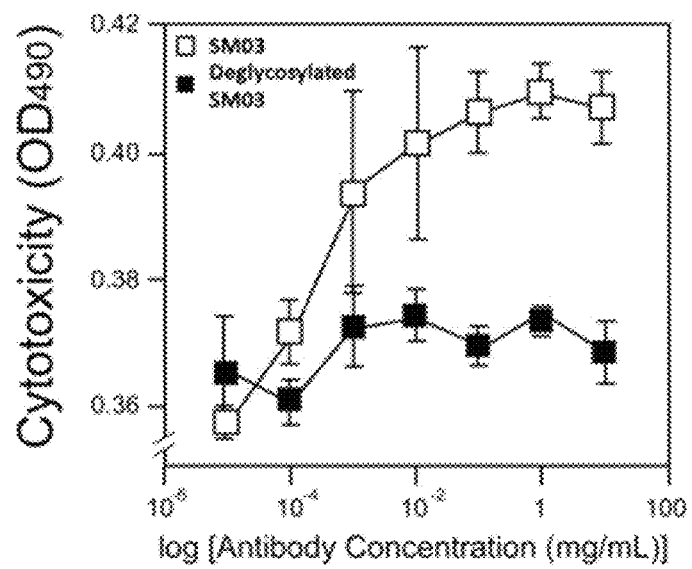
FIG. 4(B) is a dose response curve showing ADCC activities against the surrogate target cell Fab-GPI according to an example embodiment.

The anti-CD22 antibodies could induce CMC killing against either Fab-GlycoA and Fab-GPI cells (FIG. 3B); both SM03 and SM06 exhibited similar CMC killing (data not shown). The surrogate target cells can be used to assess the Fc functionality of the anti-CD22 antibodies. FIGS. 4(A) and 4(B) show SM03 deglycosylated by PNGase treatment was demonstrated to have lost the biological function in inducing (4A) CMC activities, and (4B) ADCC activities against the surrogate target cell Fab-GPI. When the anti-CD22 antibody (SM03) was deglycosylated, the deglycosylated antibody failed to induce CMC (FIG. 4A) or ADCC (FIG. 4B) against these cells, indicating that either Fab-GlycoA or Fab-GPI cells could be used as the surrogate target cells for evaluating the Fc effector functions of the anti-CD22 antibodies. Significant dose-dependent CMC activities with maximum killing at over 90% were observed, with $EC_{50}$ determined to be at 0.13 and 0.22 mg/ml, respectively (FIG. 3B).

Example 3

Specific Binding Epitope Mapping for Anti-CD22 Antibodies

Figure 5A:
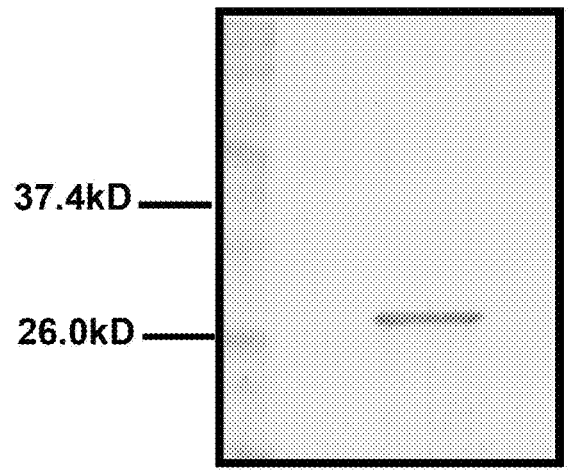
FIG. 5(A) is a reducing SDS-PAGE showing the size of the recombinant protein CD22d2-4 according to an example embodiment.
Figure 5B:
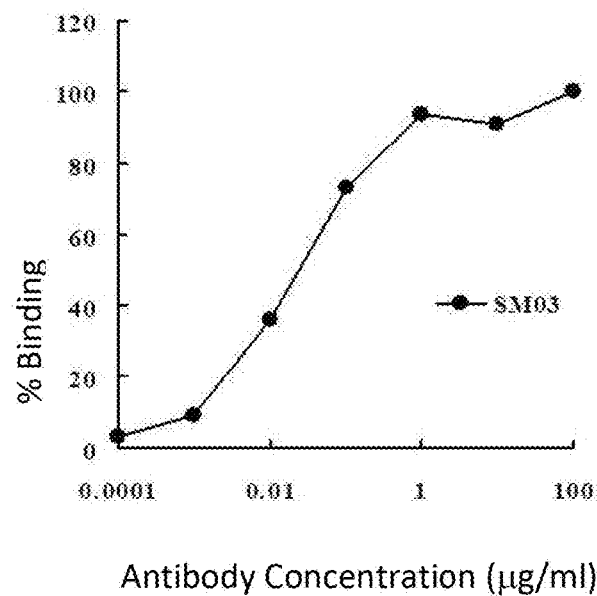
FIG. 5(B) is a dose response curve showing CD22d2-4 showed dose-response binding to the anti-CD22 antibody SM03 according to an example embodiment.

Preliminary epitope mapping was done by expressing different combinations of extracellular domains encompassing the human CD22 sequence in bacteria and the refolded recombinant proteins were tested for binding to SM03 in an ELISA assay. Only the refolded and purified human CD22 encompassing domain 2-4 (CD22d2-4)(SEQ ID 011) showed binding. The recombinant protein CD22d2-4 was analyzed by reducing SDS-PAGE (FIG. 5A), and ELISA plate coated with CD22d2-4 showed dose-response binding to the anti-CD22 antibody SM03 (FIG. 5B), indicating that the epitope resides within the domain 2-4 region of the human CD22 protein. There are 6 extracellular domains for human CD22 antigen that are expressed on the surface of matured B cells. Preliminary mapping studies by expressing different extracellular portions of human CD22 indicated that SM03 binds to the extracellular portion of human CD22 at regions encompassing domains 2-4 (CD22d2-4)(FIG. 5). Briefly, the DNA sequence encoding different domain regions of human CD22 were cloned into a pET bacterial expression vector preceded with a pelB sequence (as described in Ward et al. (1989) Nature 341:544-546). The expression vectors were used to transform bacterial host cell BL21(DE3)pLysS (Promega, Madison, WI) using standard techniques in molecular biology: expression of the transfected genes were induced by the addition of 1 mM of isopropyle β-D-thiogalactoside (IPTG). After incubating at 37° C. for 4 hours with orbital shaking at 250 rpm, the bacteria were pelleted by centrifugation at 6,000 rpm for 15 minutes. Cells were lysed in lysis buffer (50 mM Tris-HCl, pH 8 containing 0.1 M NaCl, 5 mM EDTA, 0.1% $NaN_3$, 0.5% TritonX-100, 100 μM PMSF and 1 mM DTT) with the aid of a glass homogenizer. After French press treatment, 2.5 mM $MgCl_2$ was added to chelate the EDTA, and 0.1 mg/ml Lysozyme and 0.01 mg/ml DNase were added and the mixture was incubated at room temperature for 20 minutes. Inclusion body was pelleted by centrifugation at 6,000 rpm for 15 minutes and washed three times. The pelleted inclusion bodies were dissolved in 6 M guanidine hydrochloride. The CD22d2-4 was engineered with a His tag, refolding and purification of the protein were done using a metal chelate affinity chromatography loaded with Ni Sepharose 6 Fast Flow resin (GE Healthcare, Chicago, IL) according to the manufactures' specification. The refolded CD22d2-4 was analyzed under SDS-PAGE (FIG. 5A) and was shown to exhibit dose response binding to SM03 (FIG. 5B).

Detailed epitope mapping was then performed within the domain 2-4 of human CD22 (SEQ ID NO: 011) using Pepscan technologies (Pepscan, Netherland). Initially, the linear epitope was being mapped. Briefly, to reconstruct linear epitopes of human CD22, a library of peptide based epitope mimics was synthesized using solid-phase Fmoc synthesis. An amino functionalized polypropylene support was obtained by grafting with a proprietary hydrophilic polymer formulation (Pepscan, Netherland), followed by reaction with t-butyloxycarbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer, Waltham, MA). Binding of the anti-CD22 antibodies (e.g. SM03 and SM06) to the library of overlapping synthetic peptide on the solid support could be quantified with an automated ELISA-type read-out. Briefly, the peptide arrays were incubated with the anti-CD22 antibodies such as SM03 or SM06 solution (overnight at 4° C.). After washing, the peptide arrays were incubated with a 1/1000 dilution of goat anti-human peroxidase (HRP) conjugate (Southern Biotech, Birmingham, AL) for one hour at 25° C. After washing, the peroxidase substrate 2.2'-azino-di-3-ethylbenzthiazoline sulfonate (ABTS) and 20 µg/ml of 3% $H_2O_2$ were added. After one hour, the color development was measured. The color development was quantified with a charge coupled device (CCD)—camera and an image processing system. The data were analyzed using box-and-whisker plot (Tukey 1977), linear intensity profiles, and heat map (a graphical representation of data where the values taken by a variable in a two-dimensional map were represented as colors for data visualization). Under different stringency conditions, screening of the anti-CD22 antibody (SM03 or SM06) did not yield detectable binding (Data not shown). The results suggested that either the anti-CD22 antibody did not bind to the human CD22 domains 2-4, or that the anti-CD22 antibody would only bind to a discontinuous and conformational epitope.

CLIPS Technology (Pepscan, Netherland) was then employed for the elucidation of the possible conformational or discontinuous epitopes on human CD22 that were recognized by the anti-CD22 antibody (SM03 or SM06). CLIPS technology structurally fixed peptides into defined 3D structures. The CLIPS reaction takes place between bromo groups of the CLIPS scaffold and thiol sidechains of cysteines introduced into a range of peptide structures mimicking of conformational and discontinuous binding sites. CLIPS peptide libraries could mimic secondary structure elements, such as loops, α-helixes and β-strands. Peptides based on the human CD22 sequence (SEQ ID NO: 011) were synthesized on a minicard and chemically converted into spatially defined CLIPS constructs (Pepscan, Netherland). Binding of the anti-CD22 antibodies on these conformational libraries was quantified using an automated ELISA-type read-out. Only constructs containing the right amino acid sequence in the correct conformation could best bind the anti-CD22 antibodies. The CLIPS library contained up to 10,000 overlapping peptide constructs representing both parts of the discontinuous epitope in the correct conformation; constructs presenting the incomplete epitope would bind the anti-CD22 antibodies with lower affinity, whereas constructs not containing the epitope would not bind at all.

Synthesis of structural mimics was done using Pepscan's Chemically Linked Peptides on Scaffold (CLIPS) technology (Pepscan, Netherland), structuring peptides into single loops, double-loops, triple loops, sheet-like folds, helix-like folds and combinations thereof. CLIPS templates were coupled to cysteine residues. The side-chains of multiple cysteines in the peptides were coupled to one or two CLIPS templates. For example, a 0.5 mM solution of the P2 CLIPS (2,6-bis(bromomethyl)pyridine) was dissolved in ammonium bicarbonate (20 mM, pH 7.8)/acetonitrile (1:3(v/v)). This solution was added onto the peptide arrays. The CLIPS template would bind to side-chains of two cysteines as present in the solid-phase bound peptides of the peptide-arrays (455 wells plate with 3 µl wells). The peptide arrays were gently shaken in the solution for 30 to 60 minutes while completely covered in solution. Finally, the peptide arrays were washed extensively with excess $H_2O$ and sonicated in disrupt-buffer containing 1% SDS/0.1% 2,2'-(Ethylenedioxy)diethanethiol in PBS (pH 7.2) at 70° C. for 30 minutes, followed by sonication in $H_2O$ for another 45 minutes.

Figure 6A:
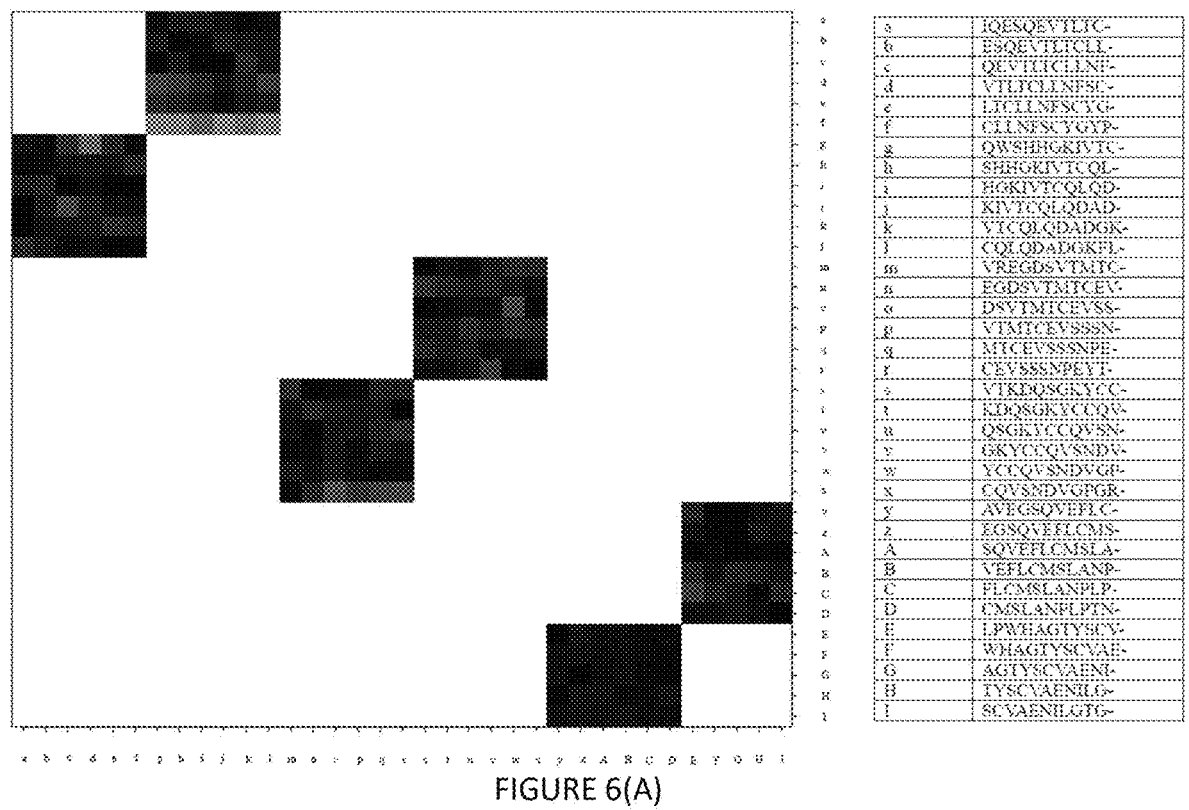
FIG. 6(A) is an intensity profile recorded for the anti-CD22 antibody SM03 under stringency conditions with disulfide bridge mimics according to an example embodiment.
Figure 6B:
FIG. 6(B) is a schematic representation of the human CD22 domains 2-4. Peptide stretch $_{161}$CLLNFSCYGYPIQ$_{173}$ is highlighted in red and peptide stretch $_{198}$VFTRSELKFSPQWSHHGKIVTC$_{219}$ is highlighted in blue.

FIG. 6(B) shows rendering of the discontinuous epitope identified using coordinate file SVKJ. Peptide stretch 161CLLNFSCYGYPIQ173 is highlighted in red and peptide stretch 198VFTRSELKFSPQWSHHGKIVTC219 is highlighted in blue. Binding of the anti-CD22 antibodies (SM03 and SM06) to the CLIPS library was quantified with an automated ELISA-type read-out using methods as previously described. The CLIP technology from Pepscan (Netherland) was used to locate the exact CD22 epitope within domains 2-4 for the anti-CD22 antibodies. The antibodies (SM03 and SM06) were found to bind to a discontinuous conformational epitope within the domain 2 of the human CD22 antigen containing the sequence $_{161}$CLLNFSCYGYPIQ$_{173}$ and $_{198}$VFTRSELKFSPQWSHHGKIVTC$_{219}$. Illustrated in (FIG. 6A) is an intensity profile recorded for the anti-CD22 antibody SM03 under stringency conditions with disulfide bridge mimics. High signals were plotted in red and background signal were plotted in black. Each square represents a certain combination of two peptide sequences containing a pair of Cys forming a disulfide bridge as per UniProt. White spaces indicate Cys pairs that do not form a disulfide bridge in a native state of human CD22; Intensity profiles recorded with combinatorial epitope mimics—discontinuous and disulfide bridge mimics—suggested that the anti-CD22 antibodies (SM03 or SM06) recognizes a discontinuous epitope composed of peptide stretches $_{161}$CLLNFSCYGYPIQ$_{173}$ an $_{198}$VFTRSELKFSPQWSHHGKIVTC$_{219}$ (FIG. 6A). A schematic representation of the human CD22 domains 2-4 with the peptide stretch $_{161}$CLLNFSCYGYPIQ$_{173}$ highlighted in red and peptide stretch $_{198}$VFTRSELKFSPQWSHHG-KIVTC$_{219}$ highlighted in blue is shown in FIG. 6B.

Example 4A

Disruptive Binding of Anti-CD22 Antibody

The human CD22 extracellular domains (domain 1 to 7: CD22d1-7) is genetically fused with a glycophorin A transmembrane and cytoplasmic region (CD22d1-7Glyco) (SEQ ID NO: 14) and/or glycophosphatidylinositol signal sequence isolated from decay accelerating factor (DAF) protein (CD22d1-7GPI) (SEQ ID NO: 15). The method of fusing the domains and sequences are performed as previously described (Leung et al. 2015. Surrogate target cells expressing surface anti-idiotype antibody for the clinical evaluation of an internalizing CD22-specific antibody. mAbs 7:66-76). The cDNA encoding the fusion protein is gene-synthesized (GeneScript, Piscataway, NJ) and cloned into an amplifiable expression vector using methods as previously described (Leung et al. 2015. mAbs 7:66-76).

The expression vector can be used to transfect a variety of mammalian host cell lines, including, without limitation, Chinese hamster ovary (CHO) cells, murine myeloma SP2/0 or NSO, baby hamster kidney (BHK) cells, human embryonic kidney 293 (HEK 293) cells, African green monkey kidney COS cell line, etc. Specifically, SP2/0 cells and DG44 CHO cells (suspension type) are transfected with the expression vector by electroporation following standard procedure. Clones surviving methotrexate (MTX) selection are tested for surface expression of human CD22 by cell-based ELISA followed by confirmatory flow cytometry, using SM03 as the probe. Briefly, 50 mL of SM03 at 10 mg/ml are added to $1 \times 10^6$ of transfected cells (washed 3× with PBS). The mixture is incubated for 1 h at 4° C., and washed 3× with PBS. 50 mL of HRP-conjugated goat anti-human Fc-specific antibody (Jackson ImmunoResearch) at a dilution of 1:1000 are added into the cells, and are incubated for 1 h at 4° C. Cells are washed once with PBS, and the presence of surface expression of human CD22 are revealed by the addition of 50 mL of TMB Solution (Invitrogen). After incubation at RT for 10 min, the reaction is stopped by the addition of 50 mL of 0.18 M $H_2SO_4$. Cells are mixed and centrifuged, and supernatant collected for evaluation at $OD_{450}$ nm with an ELISA-plate reader (Sunrise).

Cell clones that demonstrate the highest level of ELISA reading are expanded for further analyzed using flow cytometry studies: SM03 is used as the primary antibody, and FITC conjugated goat anti-human Fc-specific antibody as the detecting (secondary) antibody. Briefly, $5 \times 10^5$ of the transfected cells are incubated with 1 mg of SM03 in a final volume of 100 mL of PBD supplemented with 1% FCS and 0.01% (w/v) sodium azide (PBS-FA). The mixtures are incubated for 30 minutes at 4° C. and washed three times with PBS to remove unbound antibodies. The binding levels of SM03 to the transfected cells are assessed by the addition of a 20× diluted FITC-labeled, goat anti-human IgG1, Fc fragment-specific antibodies (Jackson ImmunoResearch) in a final volume of 100 mL in PBS-FA, and incubating for 30 minutes at 4° C. The mixture was washed three times with PBS and fluorescene intensities are measured by FACSCAN analysis (Becton Dickinson). Cell clones that demonstrate the highest level of fluorescent intensity are expanded for further tests.

Example 4B

Establishment of a Cell-Based Bioassay for the Identification of Anti-CD22 with Optimal Biological Activity and for the Evaluation of the Bioactivities of these Antibodies Both CHO and COS cells express low levels, if any, of ST6GalI (Galb1-4GlcNAc-specific a2-6-sialytransferase), and transfected CD22 in CHO cells was demonstrated to lack the a2-6-linked sialic acid (Sia) residues needed for the formation of CD22-CD22 cis-ligand binding. The surface CD22 in CHO cells expressing CD22d1-7 fusion to the transmembrane and cytoplasmic portion of glycophorin A (CD22d1-7Glyco) (CHO-CD22) do not bind to their ligands in cis and do not get internalized (as CD22d1-7 lacks the cytoplasmic portion required for the initiation of endocytosis). In other words, the ligand-binding sites of CHO expressed CD22d1-7 are free to bind to exogenous ligands, Whereas ST6GalI in the CD22d1-7Glyco or CD22d1-7-GPI transfected SP2/0 cells (SP2/0-CD22) will allow 2,6Sia formation and homomultimeric binding of CD22d1-7 in cis, making limited availability of free ligand binding sites.

Biotin-conjugated polyacrylamide substituted with a2-6-sailyllactose (6'PPA-B or known as the "Probe") is obtained from GlycoTech (Rockville, MD) and used as the exogenous probe for evaluating changes in available CD22 ligand binding sites in CHO-CD22 and SP2/0-CD22 for ligation in trans. The Probes are commercially available synthetic conjugate of biotinylated polyacrylamide substituted with multiple copies of Siaa2-6Galb1-4Glcb1 (6'PAA-B). Briefly, cells ($0.2-1 \times 10^6$) washed three times with ice-cold PBS containing 0.02% sodium azide and 1% BSA (staining buffer) are incubated on ice for 1 h in 100 mL of the same buffer either in the presence or absence of 0.1 mg of different anti-CD22 antibodies and containing 1-1.5 mg 6'PAA-B probe. After washing once with 0.5 ml of the staining buffer, cells are incubated with PE-conjugated streptavidin for 30 min to detect binding of the biotinylated probe on the cell surface.

Figures 7A, 7B:
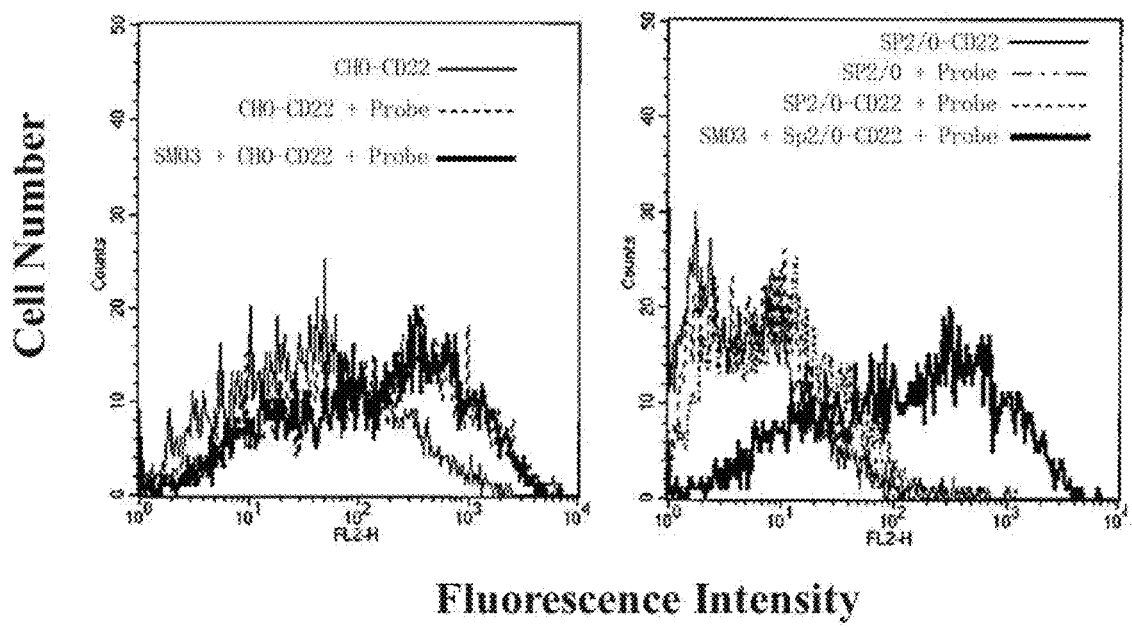
FIG. 7(A) shows a flow cytometry study of CHO cell expressing the extracellular domain of human CD22 fused to the transmembrane and cytoplasmic portion of glycophorin A (CHO-CD22), wherein the extent of binding to the probe is not affected in the presence of SM03 according to an example embodiment.
FIG. 7(B) shows a flow cytometry study of SP2/0 cell expressing the extracellular domains of human CD22 fused to the transmembrane and cytoplasmic portion of glycophorin A, wherein incubation of SP2/0-CD22 with SM03 effectively disrupt human CD22 binding in cis and allows ligation of the freed CD22 ligand binding site to bind to the 6'PAA-B Probe in trans (SM03+SP2/0-CD22+Probe) according to an example embodiment.
Figure 8A:
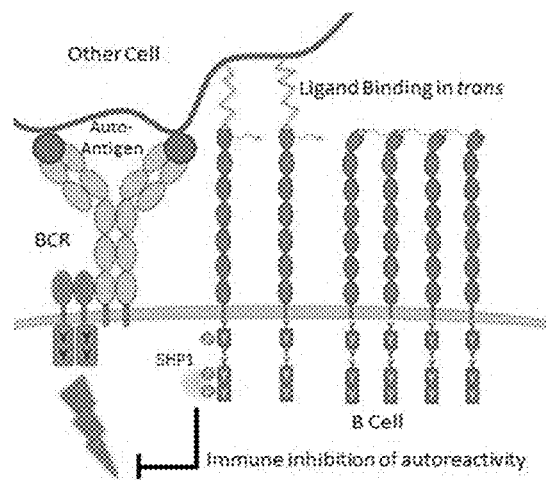
FIG. 8(A) is a schematic diagram showing that human CD22 binds to the 2,6Sia in trans immune activation arising from BCR engagement to the autoantigen will be negatively regulated, leading to tolerance to the autoantigen according to an example embodiment.
Figure 8B:
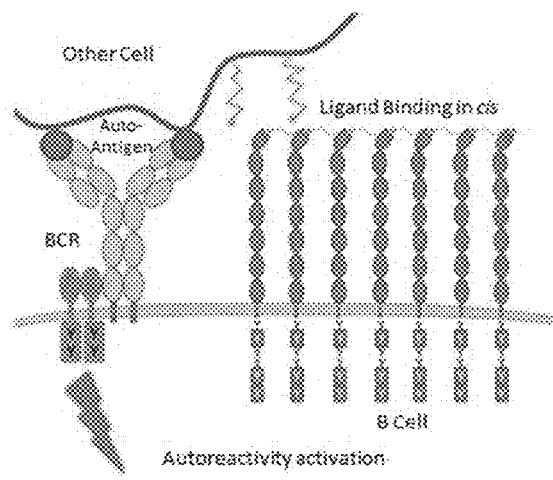
FIG. 8(B) is a schematic diagram showing that human CD22 binds to the 2,6Sia in cis, immune stimulation via BCR engagement to the autoantigen will not be regulated, leading the autoimmunity against the autoantigen according to an example embodiment.
Figure 8C:
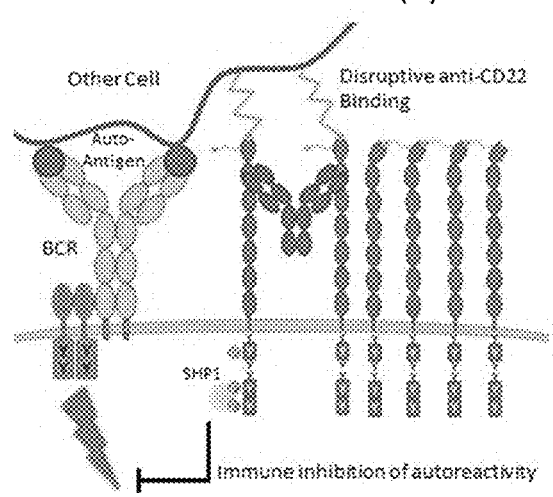
FIG. 8(C) is a schematic diagram showing that anti-CD22 antibody binds to the proper epitope at the proper domain of human CD22 close enough to the N-terminal domain with sufficiently high affinity, human CD22 antigen will be sterically separated, disrupting the cis-binding configuration; the freed human CD22 binding site will be made available to bind to the 2,6Sia ligand on the other cell in trans, mitigating the immune reaction toward the autoantigen recognized by the BCR according to an example embodiment.
Figure 8D:
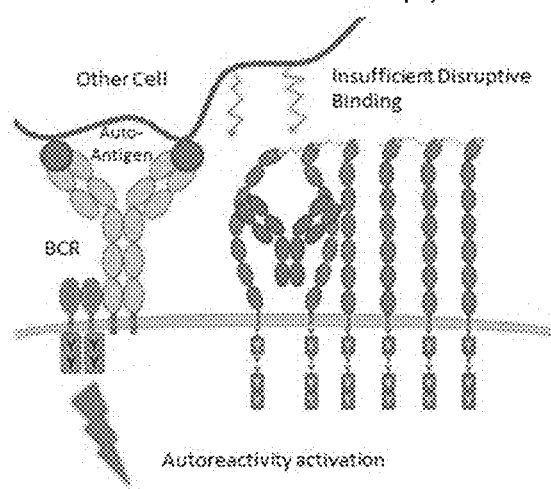
FIG. 8(D) is a schematic diagram showing that anti-CD22 binds to the human CD22 domain farther away from the N-terminal domain, or at an ineffective epitope, or with insufficient affinity, the human CD22 cis-ligation will be insufficiently disrupted, making the particular anti-CD22 less efficacious in modulating autoimmunity according to an example embodiment.
Figure 9A:
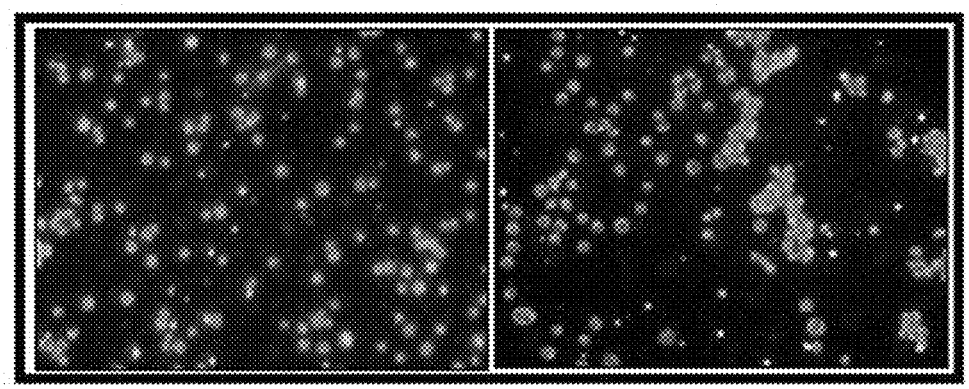
FIG. 9(A) shows confocal fluorescence microscope images of SM03 bound to the surface CD22 of Daudi (LEFT) and Raji (RIGHT) lymphoma cell lines, respectively, according to an example embodiment.
Figure 9B:
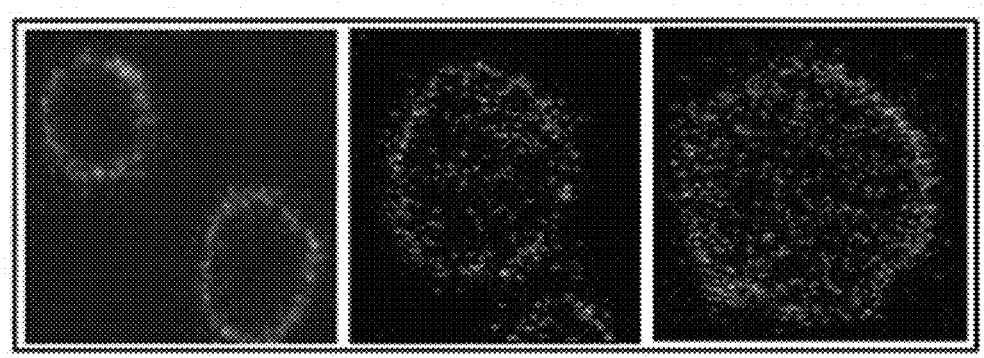
FIG. 9(B) shows confocal fluorescence microscope images of SM03 bound Raji cells incubated at 37° C. for 0 (LEFT), 10 (MIDDLE) and 20 minutes (RIGHT), respectively according to an example embodiment.
Figure 10:
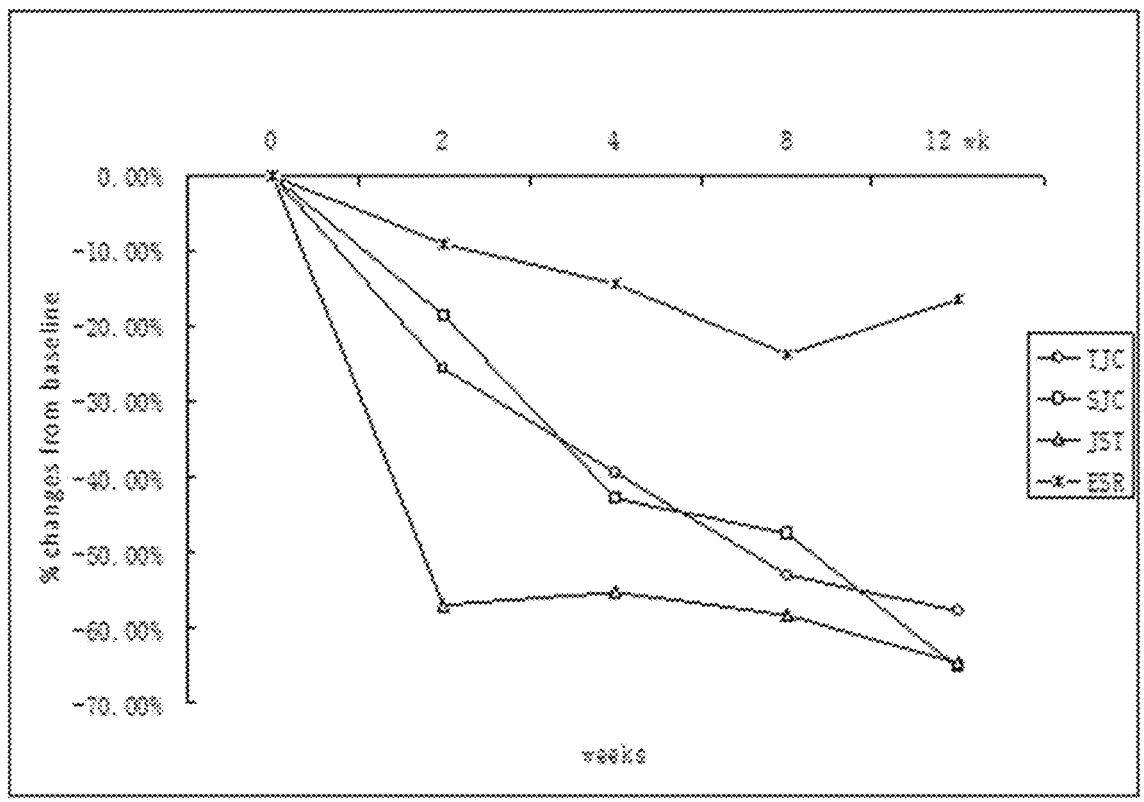
FIG. 10 depicts the time courses of tender joint count (TJC), swollen joint count (SJC), joint stiffness time (JST), and erythrocyte sedimentation rate (ESR) over twelve weeks for patients suffering from RA after two bi-weekly intravenous dosing, on day 0 and 15, with the antibody SM03 according to an example embodiment.

CHO cell expressing the extracellular domain of human CD22 fused to the transmembrane and cytoplasmic portion of glycophorin A (CHO-CD22) will not have 2,6Sia glycan structure due to the lack of the enzyme ST6Gal I in CHO. In a flow cytometry study, while 6'PAA-B does not show any binding to untransfected CHO, the probe efficiently binds to CHO cells expressing surface CD22 (CHO-CD22) (FIG. 7A) and such binding is unaffected by the presence of SM03, indicating the anti-CD22 antibody does not block the ligand-binding site of CD22. FIG. 7A shows that the extracellular domain of human CD22 on CHO binds to a probe with multiple 2,6Sia structure (biotin-conjugated polyacrylamide substituted with a2-6-sialyllactose) (6'PAA-B)(CHO-CD22+Probe), the extent of binding to the probe is not affected in the presence of 1 mg/ml of SM03 (SM03+CHO-CD22+Probe). However, binding of 6'PAA-B probe to the murine SP2/0 cells expressing surface CD22 (SP2/0-CD22) is only marginally better than binding of the probe to untransfected SP2/0; when SP2/0-CD22 is pretreated with 1 mg/ml of SM03, significantly increased binding to the treated CD22-SP2/0 is observed (FIG. 7B), indicating the binding of SM03 at the discontinuous epitope composed of peptide stretches $_{161}$CLLNFSCYGYPIQ$_{173}$ an $_{198}$VFTRSELKFSPQWSHHGKIVTC$_{219}$ located at domain 2 of CD22 efficiently breaks apart cis-ligated homomultimeric structure of CD22 and make available free ligand binding sites of CD22 for trans-binding. FIG. 7B shows that the extracellular domains of human CD22 fused to the transmembrane and cytoplasmic portion of glycophorin A expressed on SP2/0 cell (SP2/0-CD22) contain the 2,6Sia glycan and are mostly ligated as homomultimers in cis, and do not significantly bind to the 6'PAA-B Probe (SP2/0-CD22+Probe). Incubation of SP2/0-CD22 with 1 mg/ml of SM03 effectively disrupt human CD22 binding in cis and allows ligation of the freed CD22 ligand binding site to bind to the 6'PAA-B Probe in trans (SM03+SP2/0-CD22+Probe). FIG. 8 illustrates a schematic representation of the different scenarios of CD22 interactions with its ligands in cis and in trans in the presence and absence of different anti-CD22 antibodies. FIG. 8A shows that human CD22 binds to the 2,6Sia in trans immune activation arising from BCR engagement to the autoantigen will be negatively regulated, leading to tolerance to the autoantigen. FIG. 8B shows that human CD22 binds to the 2,6Sia in cis, immune stimulation via BCR engagement to the autoantigen will not be regulated, leading the autoimmunity against the autoantigen. FIG. 8C shows that anti-CD22 antibody binds to the proper epitope at the proper domain of human CD22 close enough to the N-terminal domain with sufficiently high affinity, human CD22 antigen will be sterically separated, disrupting the cis-binding configuration; the freed human CD22 binding site will be made available to bind to the 2,6Sia ligand on the other cell in trans, mitigating the immune reaction toward the autoantigen recognized by the BCR. FIG. 8D shows that anti-CD22 binds to the human CD22 domain farther away from the N-terminal domain, or at an ineffective epitope, or with insufficient affinity, the human CD22 cis-ligation will be insufficiently disrupted, making the particular anti-CD22 less efficacious in modulating autoimmunity.

Example 5

Binding of SM03 onto CD22 in Burkitt's Lymphoma Cells Induces Internalization Human CD22 antigens are highly expressed on the surface of human Burkitt's lymphoma cell lines Daud and Raji, as revealed by phase contrast fluorescence miscroscope after the incubation of $5\times10^6$/ml with SM03 at a final concentration of 1 mg/ml on ice (FIG. 9A). The distribution of bound SM03 on Raji cells was monitored employing confocal fluorescence microscopy with a slight modification according to the method of Pirker (Pirker et al. 1987. Characterization of immunotoxin active against ovarian cancer cell line. *J. Clin. Invest.* 76:1261-1267). Briefly, 100 ml of Raji cells at a concentration of $5\times10^6$/ml in RPMI 1640 (Invitrogen, Gaithersburg, MD) were mixed with 100 ml of SM03 at a concentration of 40 mg/ml and incubated at 37° C. for 0 min, 10 min and 20 min, respectively. Cells were washed three times with PBS containing 1% FBS and fixed with 3.7% formaldehyde at 4° C. for 15 min. SM03 distribution on and within (internalization) Raji cells was revealed by FITC conjugated goat anti-human Fc specific antibody under a confocal microscope (FIG. 9B). The surface bound SM03 was shown to internalize to the intracellular compartments of the lymphoma cell line, as revealed by confocal fluorescence microscopes (FIG. 9B). At 10 min, over 50% of the surface bound SM03 were internalized, and by 20 min, the internalized SM03 appeared to recycle to the cell surface, as surface intensity had increased compared to that at the 10 min time point (FIG. 9B).

Example 6

Treatment with an Anti-CD22 Antibody

SM03 Efficacy Following Intravenous Administration

In this open label study, eight patients with active RA were treated with two injections of 600 mg per dose (roughly equivalent to 360 mg/$m^2$) of SM03 on day 0 and day 15, in addition to their on-going treatment with (methotrexate) MTX. Patients participating in this study had a mean duration of disease of 5.8 years with a disease activity score (DAS28) of 5.78, reflecting considerable disease activity.

Four of the eight patients treated with SM03 achieved a DAS28-based EULAR response and ACR20 over twelve weeks, with the earliest response onset on the $4^{th}$ week; one of them achieved ACR70 (Table 2 below).

TABLE 2

Percentage of ACR responders following Two injections of SM03 (600 mg) during an Open-label Phase I study

| ACR | Week 4 | Week 8 | Week 12 |
|---|---|---|---|
| ACR20 | 2 (25%) | 3 (37.5%) | 4 (50%) |
| ACR50 | 0 | 0 | 1 (12.5%) |
| ACR70 | 0 | 0 | 1 (12.5%) |

Two of the responders began to observe ACR improvement on day 28, and the remaining responders did not achieve ACR responses until Day 56 and Day 84, respectively. Unlike other TNFα-targeting antibodies, which could demonstrate ACR responses in as early as the first week after antibody administration, indicating that anti-CD22 responses against RA might be slow-acting.

In agreement with the ACR scores, DAS28 scores for enrolled patients trended lower with time, albeit slowly, with the DAS28 score achieving its lowest value (down by a value of approximately 0.6) on DAY 84 post SM03 administration. Four of the eight patients achieved DAS EULAR responses on day 84, of which one was considered good EULAR response. Regarding the average baseline value for high activity RA patients of over 5.1, the change in DAS28 score observed did not reflect responses to the SM03 treatment.

If a reduction of DAS28 score of individual patients by over 0.6-1.2 was being considered as reflecting "moderate responses", two patients treated with SM03 could be considered as having achieved moderate responses. Although two other patients achieved DAS28 reduction by over 1.2, one on Day28 and the other on Day 56, the score bounced back upon subsequent follow-up visits. Regardless, the results indicated that two i.v. dosing of 600 mg of SM03 were effective for treating RA with a good safety and tolerability profile.

Example 7

Total Body Dose of an Intravenously Administered Anti-CD22 Antibody

Bi-Weekly, Intravenous Administration of SM03 in Two Cycles

The clinical effects, safety, immunogenicity, and tolerance of RA patients with insufficient response to MTX following biweekly intravenously (i.v.) injections of placebo or SM03 at two cumulative dose levels in two cycles, each with two or three injections in conjunction with continued MTX treatment was investigated.

A placebo-controlled, double-blind, randomized, multi-center study in patients with RA, who had insufficient response or tolerability to MTX was performed. During the course of the trial, patients were continued on a stable dose of MTX with dose ranges specified in the inclusion criteria described below.

The study consisted of two portions: 1) a "wash-out period" of four weeks prior to the administration of the first dose medication, during which time DMARDs (except for MTX) were withdrawn; and 2) a "placebo controlled period" during which time patients were randomized to one of three cohorts of fifty-two patients to receive placebo, 2×600 mg SM03 in two cycles, or 3×600 mg SM03, given every other week, in two cycles with the first cycle starting at week 0 and the second cycle at week 12.

Patients were serially examined in weeks zero (before SM03 administration), two, four, eight, twelve, sixteen and twenty-four of the study with the joint examinations being performed by a blinded physician (investigator).

This study enrolled one hundred and fifty-six patients with RA. The study population was representative of the moderate to severe RA population in Northern, West Southern, and Eastern part of China: approximately 86% female, and predominantly over the age of forty-four. The population was selected using predetermined inclusion and exclusion criteria, known to those of skill in the art e.g., a patient must have received a diagnosis of RA as defined by the 1987-revised American College of Rheumatology (ACR) criteria (set forth in Appendix A: Arnett F. C., et al. (1988) The American Rheumatism Association 1987 revised criteria for the classification of rheumatoid arthritis. Arthritis Rheum. 31:314-324).

Results

Figure 11A:
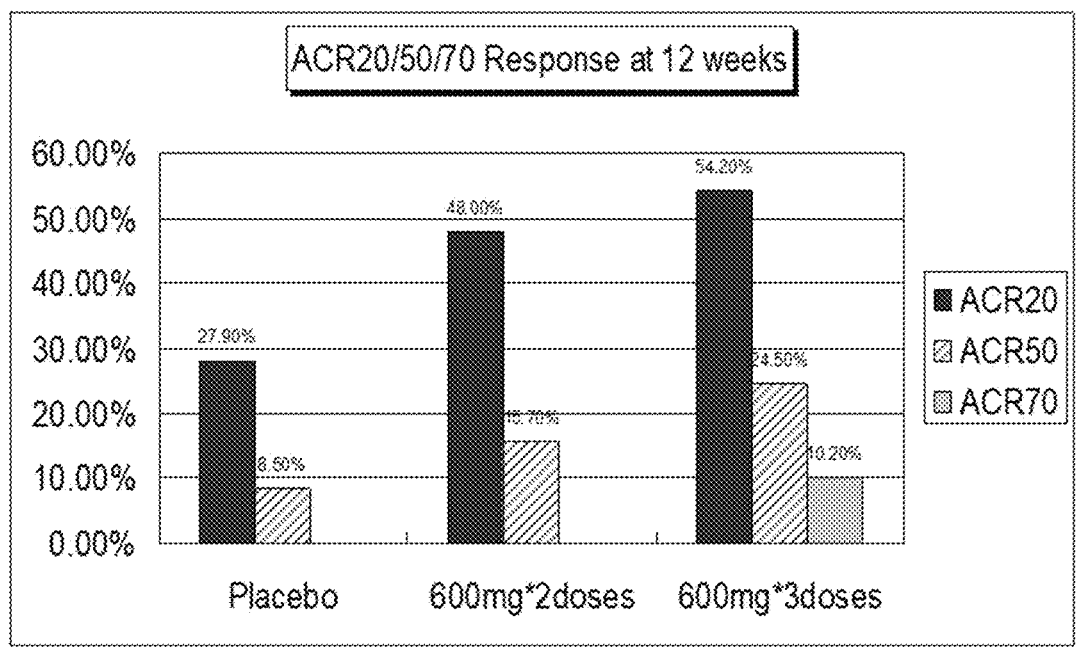
FIG. 11(A) depicts ACR20, ACR50, and ACR70 responses for patients suffering from RA after two cycles of intravenous dosing with the antibody SM03 and methotrexate either with two biweekly or three biweekly dosing per cycle at twelve weeks according to an example embodiment.
Figure 11B:
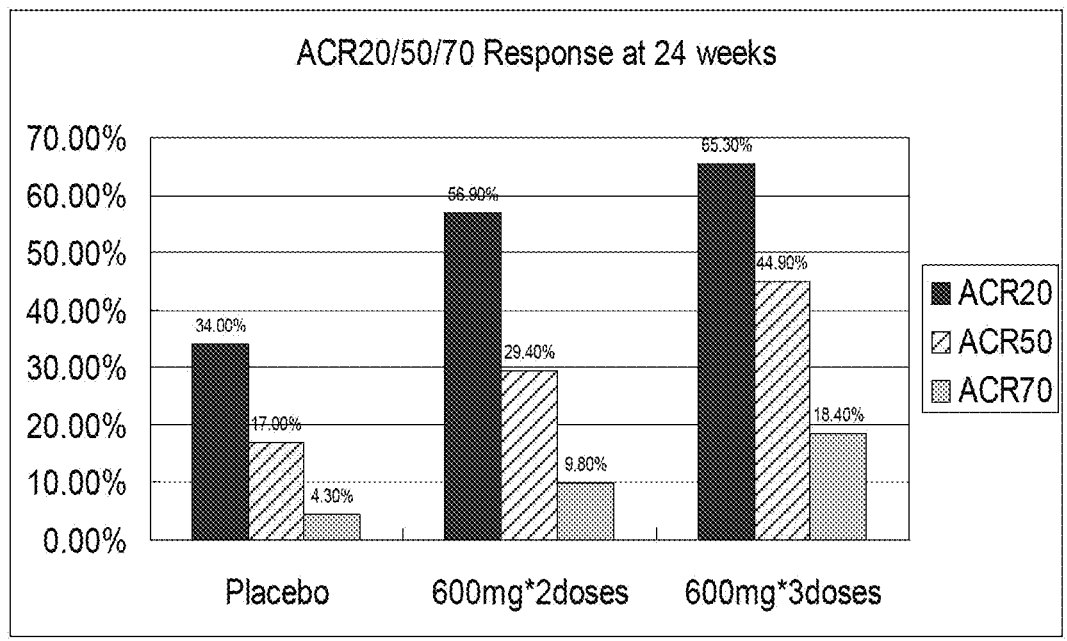
FIG. 11(B) depicts ACR20, ACR50, and ACR70 responses for patients suffering from RA after two cycles of intravenous dosing with the antibody SM03 and methotrexate either with two biweekly or three biweekly dosing per cycle at twenty-four weeks according to an example embodiment.
Figure 12A:
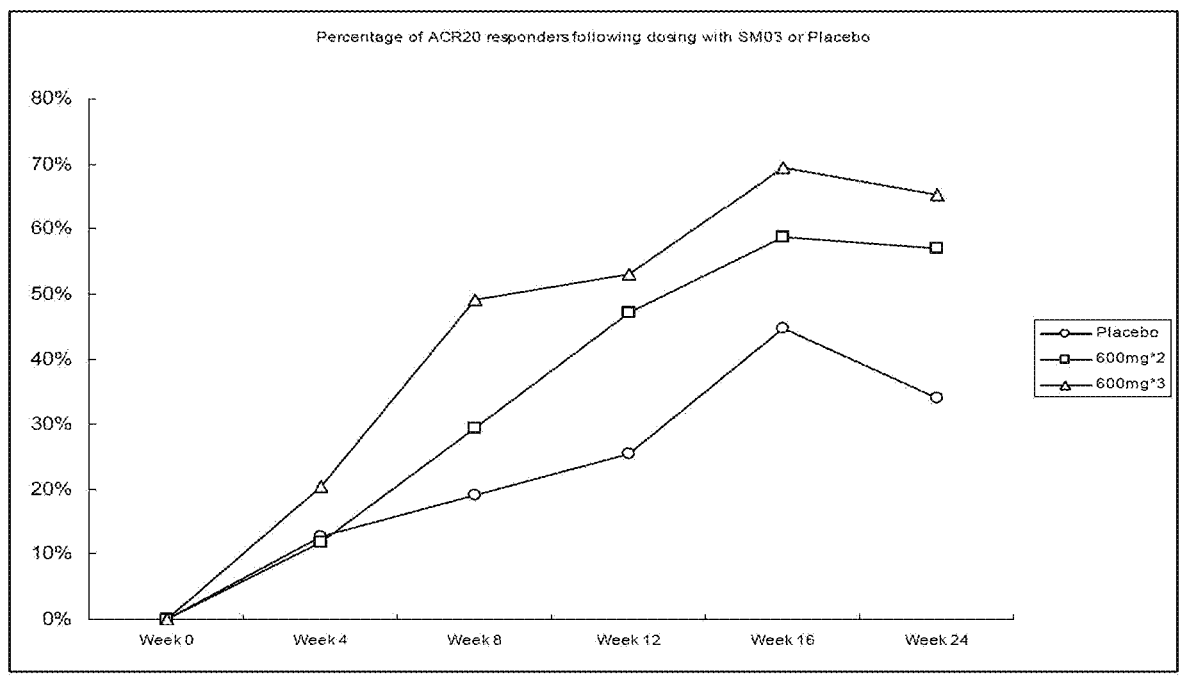
FIG. 12(A) is a graphical representation on the percentage of ACR20 responders over 24 weeks after intravenous dosing with the antibody SM03 or placebo in patients suffering from RA according to an example embodiment.
Figure 12B:
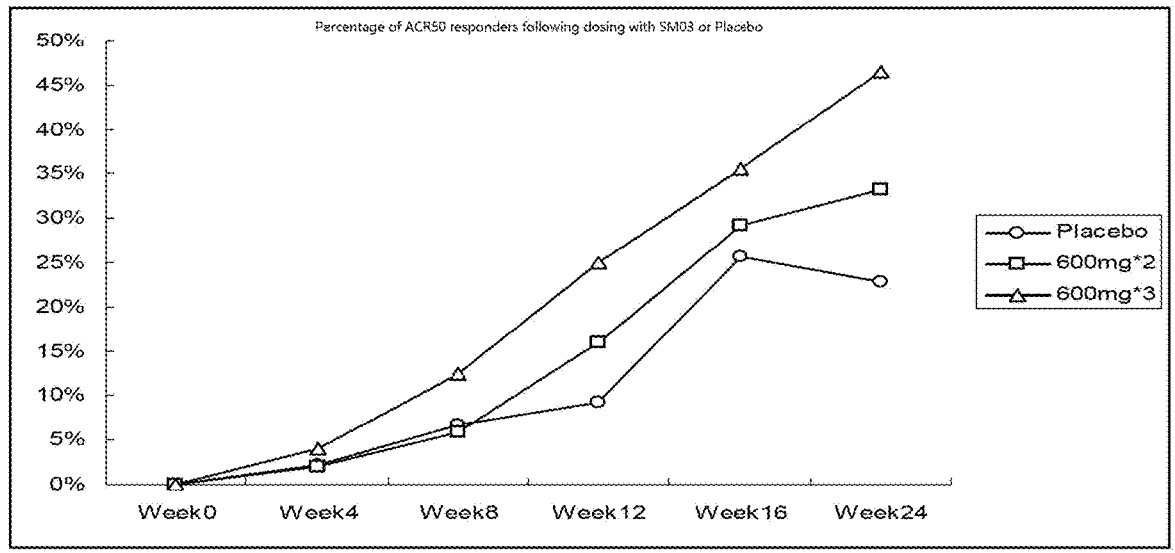
FIG. 12(B) is a graphical representation on the percentage of ACR50 responders over 24 weeks after intravenous dosing with the antibody SM03 or placebo in patients suffering from RA according to an example embodiment.
Figure 12C:
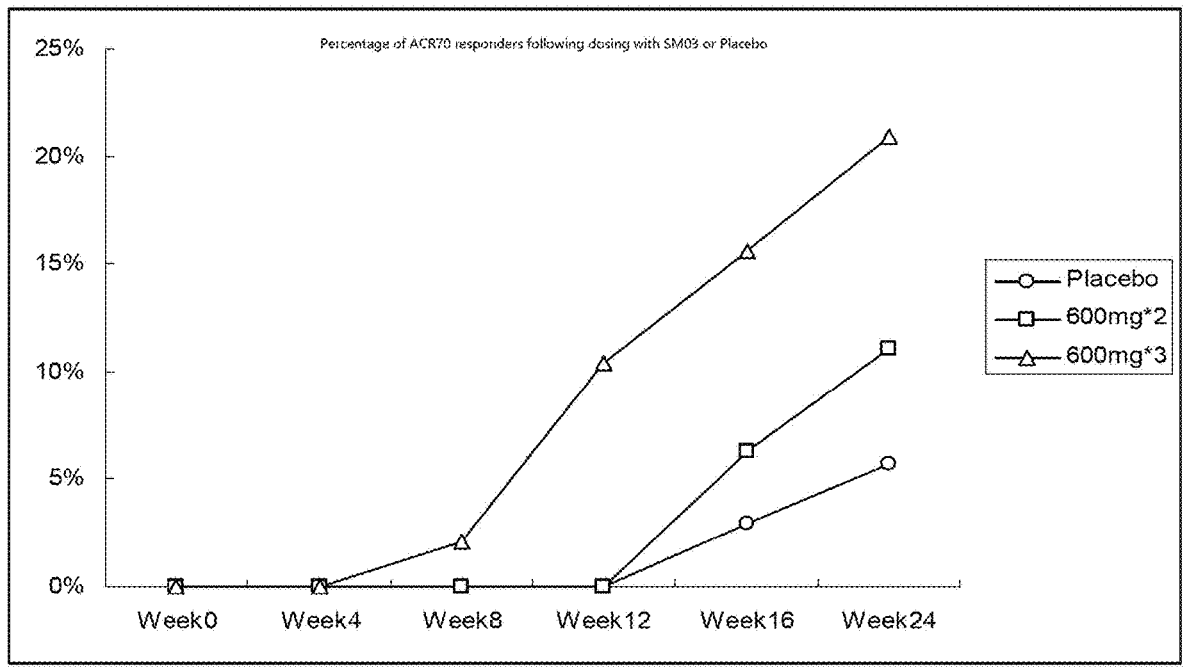
FIG. 12(C) is a graphical representation on the percentage of ACR70 responders over 24 weeks after intravenous dosing with the antibody SM03 or placebo in patients suffering from RA according to an example embodiment.
Figure 13A:
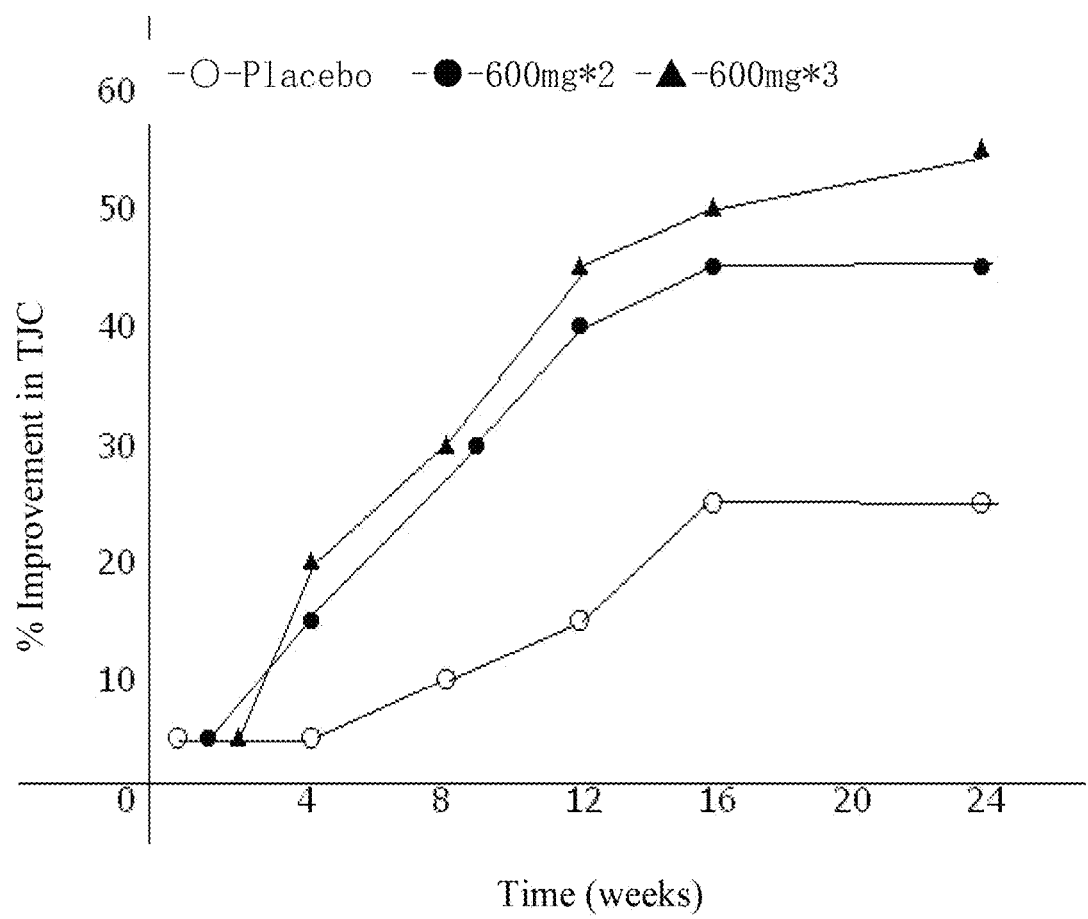
FIG. 13(A) depicts time courses of tender joint count over twenty-four weeks for patients suffering from RA after two cycles of two or three biweekly intravenous dosing with SM03 and methotrexate at twenty-four week according to an example embodiment.
Figure 13B:
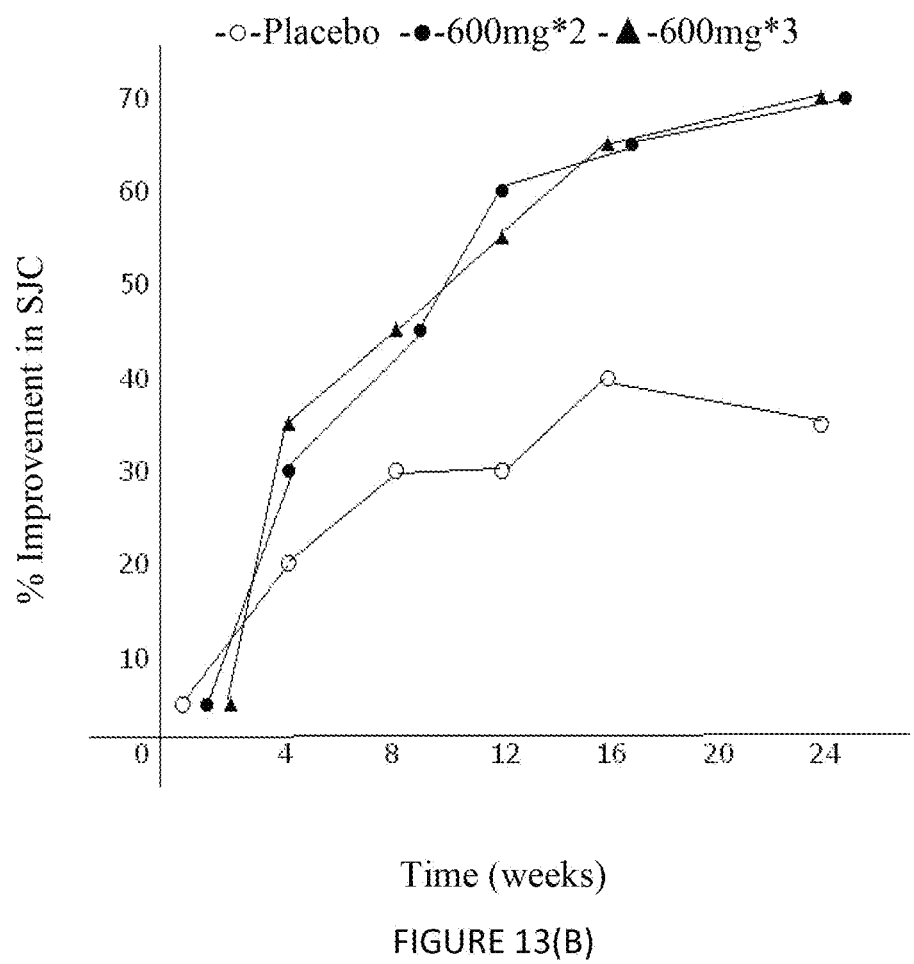
FIG. 13 (B) depicts time courses of and swollen joint count over twenty-four weeks for patients suffering from RA after two cycles of two or three biweekly intravenous dosing with SM03 and methotrexate at twenty-four week according to an example embodiment.
Figure 14:
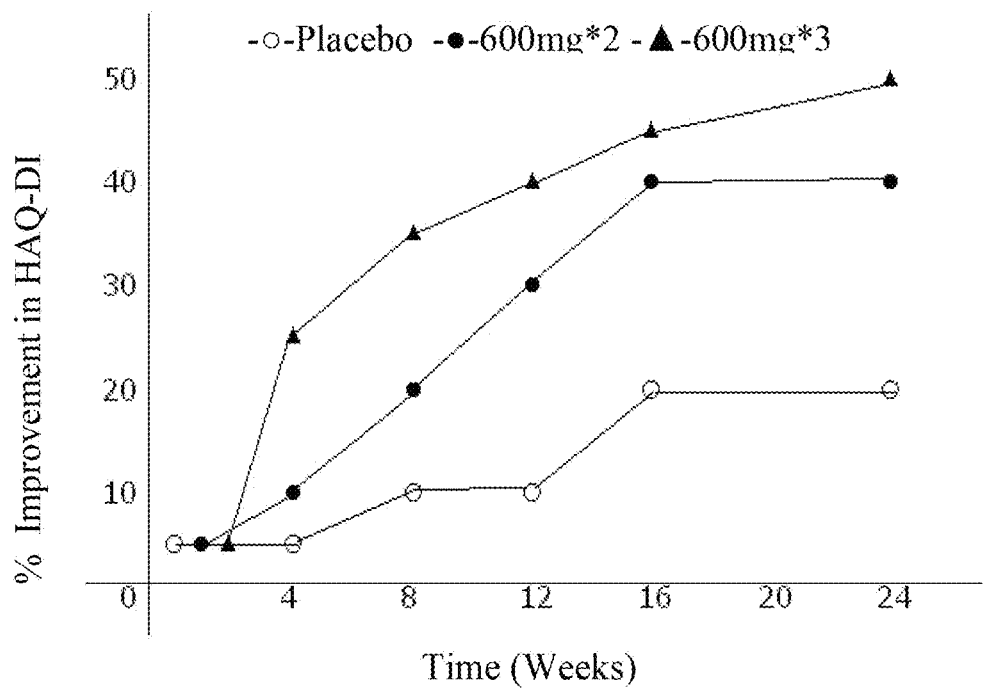
FIG. 14 depicts time course of a Health Assessment Questionnaire Disability Index (HAQ-DI) from patients suffering from RA after two cycles of either two or three biweekly intravenous dosing with SM03 and methotrexate at twenty-four weeks according to an example embodiment.

FIGS. 8-11 indicate that intravenous, biweekly SM03 treatment in two cycles, either with two biweekly administration or three biweekly administration, when combined with methotrexate, was significantly better than placebo in reducing the signs and symptoms of RA at twenty-four weeks (FIG. 11(B)). Interestingly, all dosing regimens of SM03 were significantly more effective than placebo given following the same dosing schedules of the treatment groups, when assessed with ACR20 responses, even at week 12 (FIG. 11(A)). Furthermore, treatment cycle with three biweekly administration of 600 mg of SM03 had better efficacy than treatment cycle with two biweekly administration of 600 mg of SM03, when assessed with different efficacy variables such as tender and swollen joint counts (FIGS. 13(A) and 13(B)) or Health Assessment Questionnaire Disability Index (HAQ-DI) (FIG. 14).

Specifically, at week 24, approximately 57% of patients treated with 2×600 mg of SM03, and 65% of patients treated with 3×600 mg of SM03 achieved ACR20, whereas only 34% of placebo achieved ACR20; furthermore, roughly 30% and 45% of patients treated with 2×600 mg and 3×600 mg SM03, respectively, achieved ACR50 (versus 17% of patients in the placebo group with ACR50 response); and roughly 10% and 18.4% of patients treated with 2×600 mg and 3×600 mg SM03, respectively, achieved ACR70 (versus 4% of patients in the placebo group with ACR70 response).

Example 8

Safety Profile of Anti-CD22 Antibody

TABLE 3 safety profile: SM03 vs Rituximab vs Infliximab

| Adverse Event (AE) | Rituximab* (N = 492) | Infliximab** (N = 301) | SM03 (N = 103) |
|---|---|---|---|
| Any AE | 467 (94.9%) | 183 (60.8%) | 45 (43.7%) |
| Treatment related AE | 187 (38.0%) | 108 (35.8%) | 13 (12.6%) |
| Any serious AE (SAE) | 145 (29.5%) | 21 (7.0%) | 1 (0.9%) |
| Death | 11 (2.2%) | 2 (0.7%) | — |
| AE leading to withdrawn | 33 (6.7%) | 30 (10%) | 2 (1.9%) |
| Any infusion related reaction | 158 (32.1%) | 31 (10%) | 1 (0.9%) |
| Any infection | 405 (82.3%) | 136 (45.3%) | 13 (12.6) |
| Serious | 63 (12.8%) | Tuberculosis (8.3%) | — |
| Any malignancy | 21 (4.3%) | 3 (1%) | — |
| serious | 11 (2.2%) | — | |

*Rituximab Clinical Summary Report, Protocol Number: WA17045, Jan. 8, 2012
**Remsima Assessment Report. Pivotal Phase III Study CT-13 3.1.EMA/CHMP/589317/2013

Table 3 shows the safety data on SM03 for the trial conducted in Example 7, specifically on the incidences of adverse events for serious infection, compared to other anti-TNFα antibodies and anti-CD20 antibodies.

It shows that SM03 has significantly lower adverse events than Rituximab or Infliximab, because the conversion from cis- to trans-configuration facilitated by SM03 binding does not interfere with the normal immunoregulatory functions of B cells against infectious agents such as bacteria and viruses (since they do not have the needed 2,6 sialic acid ligand for binding to CD22, even at trans-configuration). Anti-CD20 antibodies, by contrast, suppress immunoreactivities against autologous cell by the complete ablation of circulating B cells. This will lead to the loss of B cell immunoregulatory functions, and is probably the main reason why treatment with the anti-CD20 Rituximab resulted in high incidences of adverse events, specifically on opportunistic infections (Table 3).

Similarly, neutralization of TNFα also eliminates the normal anti-infectious functions of TNFα as evident by the high incidence of adverse events, particularly serious infections in patients treated with the anti-TNFα antibody Infliximab (Table 3).

EQUIVALENTS

Those skilled in the art will recognize, or be able to ascertain using more than routine experimentation, many equivalents to the specific embodiments of the invention described herein. Such equivalents are intended to be encompassed by the following claims.

All patents, patent applications, and publications cited herein are incorporated by reference in their entirety.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made herein without departing from the spirit and scope of the invention. Thus, the invention is defined not by the above description, but by the following claims and their equivalents.

This application incorporates by reference a Sequence Listing with this application as an ASCII text file entitled "022A002US01_ST25" created on Oct. 15, 2019 and having a size of 24,808 bytes.

What is claimed:

1. A fusion protein comprising human CD22 domain 2 and (a) the transmembrane and cytoplasmic portion of glycophorin A or (b) the glycophosphatidylinositol signal sequence isolated from decay accelerating factor (DAF) protein.

2. The fusion protein of claim 1 comprising human CD22 domain 1 to 7.

3. The fusion protein of claim 1 having an amino acid sequence having at least 95% sequence identity to SEQ ID NO: 14.

4. The fusion protein of claim 3 having the amino acid sequence of SEQ ID NO: 14.

5. The fusion protein of claim 1 having an amino acid sequence having at least 95% sequence identity to SEQ ID NO: 15.

6. The fusion protein of claim 5 having the amino acid sequence of SEQ ID NO: 15.

7. An engineered mammalian cell line comprising the fusion protein of claim 1 and a ST6GAL I enzyme.

8. The mammalian cell line of claim 7 wherein the fusion protein comprises human CD22 domain 1 to 7.

9. The mammalian cell line of claim 7 wherein the fusion protein has an amino acid sequence having at least 95% sequence identity to SEQ ID NO: 14.

10. The mammalian cell line of claim 9 wherein the fusion protein has the amino acid sequence of SEQ ID NO: 14.

11. The mammalian cell line of claim 7 wherein the fusion protein has an amino acid sequence having at least 95% sequence identity to SEQ ID NO: 15.

12. The mammalian cell line of claim 11 wherein the fusion protein has the amino acid sequence of SEQ ID NO: 15.

* * * * *